(12) United States Patent
Ledneczki et al.

(10) Patent No.: US 12,194,050 B2
(45) Date of Patent: Jan. 14, 2025

(54) THIADIAZINE DERIVATIVES

(71) Applicant: RICHTER GEDEON NYRT., Budapest (HU)

(72) Inventors: István Ledneczki, Bölcske (HU); János Éles, Budapest (HU); Pál Tapolcsányi, Budapest (HU); Erszébet Jablonkai, Budapest (HU); Eszter Gábor, Tura (HU); András Visegrádi, Budapest (HU); Zsolt Némethy, Göd (HU); György István Lévay, Budakeszi (HU); József Levente Petro, Százhalombatta (HU); György Selényi, Dunakeszi (HU)

(73) Assignee: RICHTER GEDEON NYRT., Budapest (HU)

( * ) Notice: Subject to any disclaimer, the term of this patent is extended or adjusted under 35 U.S.C. 154(b) by 306 days.

(21) Appl. No.: 17/259,975

(22) PCT Filed: Jul. 12, 2019

(86) PCT No.: PCT/IB2019/055949
§ 371 (c)(1),
(2) Date: Jan. 13, 2021

(87) PCT Pub. No.: WO2020/012423
PCT Pub. Date: Jan. 16, 2020

(65) Prior Publication Data
US 2021/0267993 A1    Sep. 2, 2021

(30) Foreign Application Priority Data

Jul. 13, 2018    (HU) .................................. P1800249

(51) Int. Cl.
| | | |
|---|---|---|
| *A61K 31/549* | (2006.01) | |
| *A61K 31/198* | (2006.01) | |
| *A61K 45/06* | (2006.01) | |
| *A61P 25/28* | (2006.01) | |
| *C07D 285/16* | (2006.01) | |
| *C07D 417/12* | (2006.01) | |
| *C07D 417/14* | (2006.01) | |
| *C07D 471/04* | (2006.01) | |

(52) U.S. Cl.
CPC .......... *A61K 31/549* (2013.01); *A61K 31/198* (2013.01); *A61K 45/06* (2013.01); *A61P 25/28* (2018.01); *C07D 285/16* (2013.01); *C07D 417/12* (2013.01); *C07D 417/14* (2013.01); *C07D 471/04* (2013.01)

(58) Field of Classification Search
CPC .... A61K 31/549; A61K 31/198; A61K 45/06; A61P 25/28; C07D 285/16; C07D 417/12; C07D 417/14; C07D 471/04
See application file for complete search history.

(56) References Cited

U.S. PATENT DOCUMENTS

| | | |
|---|---|---|
| 2010/0298314 A1 | 11/2010 | Reddy et al. |
| 2012/0208796 A1 | 8/2012 | Ratcliffe et al. |
| 2013/0310419 A1 | 11/2013 | Sinha et al. |
| 2021/0330650 A1 | 10/2021 | Eles et al. |

FOREIGN PATENT DOCUMENTS

| | | |
|---|---|---|
| CA | 3055194 A1 | 9/2018 |
| CN | 102666540 A | 9/2012 |
| CN | 103443092 A | 12/2013 |
| CN | 105051024 A | 11/2015 |
| EP | 1782811 A1 | 5/2007 |
| JP | 2020511436 A | 4/2020 |
| WO | WO-2007031440 A2 | 3/2007 |
| WO | WO-2007054601 A1 | 5/2007 |
| WO | WO-2009043780 A1 | 4/2009 |
| WO | WO-2009043784 A1 | 4/2009 |
| WO | WO-2009100294 A2 | 8/2009 |
| WO | WO-2009115547 A1 | 9/2009 |
| WO | WO-2009127609 A1 | 10/2009 |

(Continued)

OTHER PUBLICATIONS

Database Registry [online], Chemical Abstracts Service, Columbus, Ohio, US, XP002793754, Retrieved From STN, Database Accession No. 1944825-80-2 (Jul. 4, 2016).

(Continued)

*Primary Examiner* — Samantha L Shterengarts
*Assistant Examiner* — Jed A Kucharczk
(74) *Attorney, Agent, or Firm* — Sterne, Kessler, Goldstein & Fox P.L.L.C.

(57) ABSTRACT

The invention relates to thiadiazine derivatives, or pharmaceutically acceptable salts, biologically active metabolites, pro-drugs, racemates, enantiomers, diastereomers, solvates and hydrates thereof, as well as to pharmaceutical compositions containing them and to their use as modulators of α7 nicotinic acetylcholine receptor activity in a mammalian subject Formula (I):

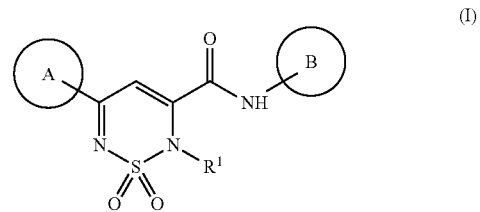

(I)

15 Claims, 4 Drawing Sheets

(56) References Cited

FOREIGN PATENT DOCUMENTS

| WO | WO-2009127678 | A1 | 10/2009 | | |
|---|---|---|---|---|---|
| WO | WO-2009127679 | A1 | 10/2009 | | |
| WO | WO-2009135944 | A1 | 11/2009 | | |
| WO | WO-2009155017 | A2 | 12/2009 | | |
| WO | WO-2011079804 | A1 | 7/2011 | | |
| WO | WO-2012042915 | A1 | 4/2012 | | |
| WO | WO-2014141091 | A1 | 9/2014 | | |
| WO | WO-2017165256 | A1 | 9/2017 | | |
| WO | WO-2018085171 | A1 | 5/2018 | | |
| WO | WO-2018112204 | A1 | 6/2018 | | |
| WO | WO-2018160878 | A1 * | 9/2018 | ........... | A61K 31/549 |
| WO | WO-2020012422 | A1 | 1/2020 | | |

OTHER PUBLICATIONS

Database Registry [online], Chemical Abstracts Service, Columbus, Ohio, US, XP002793753, Retrieved From STN, Database Accession No. 1947149-33-8 (Jul. 7, 2016).
Database Registry [online], Chemical Abstracts Service, Columbus, Ohio, US, XP002793752, Retrieved From STN, Database Accession No. 1953198-57-6 (Jul. 15, 2016).
Database Registry [online], Chemical Abstracts Service, Columbus, Ohio, US, XP002793751, Retrieved From STN, Database Accession No. 2224106-02-7 (May 20, 2018).
International Search Report and Written Opinion for International Application No. PCT/IB2019/055948, European Patent Office, Rijswijk, Netherlands, dated Oct. 24, 2019, 12 pages.
PubChem, "3-Chloro-1-methylprrolo[2,3-b]pyridine-5-yl)methanamine," pubchem.ncbi.nlm.nih.gov, PubChem CID: 126539609, created Apr. 22, 2017, XP002793755, accessed at URL:https://pubchem.ncbi.nlm.nih.gov/compound/126539609 on Sep. 2, 2021, 8 pages.
Alsharari, S.D., et al., "Functional Role of Alpha7 Nicotinic Receptor in Chronic Neuropathic and Inflammatory Pain: Studies in Transgenic Mice," Biochemical Pharmacology 86(8):1201-1207, Elsevier Science, England (Oct. 2013).
Ancin, I., et al., "CHRNA7 haplotypes are associated with impaired attention in euthymic bipolar disorder," Journal of Affective Disorders 133(1-2):340-345, Elsevier/North-Holland Biomedical Press, Netherlands (Sep. 2011).
Bali, Z.K., et al., "Alpha7 Nicotinic Acetylcholine Receptors Play a Predominant Role in the Cholinergic Potentiation of N-Methyl-D-Aspartate Evoked Firing Responses of Hippocampal CA1 Pyramidal Cells," Frontiers in Cellular Neuroscience 11:271, Frontiers Research Foundation, Switzerland (Sep. 2017).
Bencherif, M., et al., "Alpha7 Nicotinic Receptors as Novel Therapeutic Targets for Inflammation-based Diseases," CMLS 68(6):931-949, Springer, Switzerland (Mar. 2011).
Bertrand, D., "Neuronal Nicotinic Acetylcholine Receptors and Epilepsy," Epilepsy Currents 2(6):191-193, SAGE Publications, United States (Nov. 2002).
Bray, C., et al., "Mice Deficient in Chrna7, a Subunit of the Nicotinic Acetylcholine Receptor, Produce Sperm With Impaired Motility," Biology of Reproduction 73(4):807-814, Society for the Study of Reproduction, United States (Oct. 2005).
Buchfuhrer, M.J., "Strategies for the Treatment of Restless Legs Syndrome," Neurotherapeutics 9(4):776-790, Springer, United States (Oct. 2012).
Canning, B.J. and Liu, Q., "Nicotinic Receptor Subtypes as Targets for Antitussive Therapy Preclinical Studies Performed in Guinea Pigs," American Journal of Respiratory and Critical Care Medicine 195:A4498 (2017).
Capo-Velez, C.M., et al., "The Alpha7-nicotinic Receptor Contributes to Gp120-induced Neurotoxicity: Implications in HIV-associated Neurocognitive Disorders," Scientific Reports 8(1):1829, Nature Publishing Group, England (Jan. 2018).
Carson, R., et al., "Genetic Variation in the alpha 7 Nicotinic Acetylcholine Receptor is Associated With Delusional Symptoms in Alzheimer's Disease," Neuromolecular Medicine 10(4):377-384, Humana Press, United States (2008).
Castro, N.G. and Albuquerque, E.X., "Brief-lifetime, Fast-inactivating Ion Channels Account for the Alpha-bungarotoxin-sensitive Nicotinic Response in Hippocampal Neurons," Neuroscience Letters 164(1-2):137-140, Elsevier Scientific Publishers, Ireland (Dec. 1993).
Chen, J.K., et al., "Downregulation of Alpha7 Nicotinic Acetylcholine Receptor in Two-kidney One-clip Hypertensive Rats," BMC Cardiovascular Disorders 12:38, BioMed Central, England (Jun. 2012).
Clifford, P.M., et al., "Alpha7 Nicotinic Acetylcholine Receptor Expression by Vascular Smooth Muscle Cells Facilitates the Deposition of Abeta Peptides and Promotes Cerebrovascular Amyloid Angiopathy," Brain Research 1234:158-171, Amsterdam Elsevier/North-Holland Biomedical Press, Netherlands (Oct. 2008).
Cocores, J.A., "Transdermal Nicotine in Adult ADHD With Depression and Anxiety," Primary Care Companion to the Journal of Clinical Psychiatry 10(3):253-254, Physicians Postgraduate Press, United States (2008).
Couturier, S., et al., "A Neuronal Nicotinic Acetylcholine Receptor Subunit (Alpha 7) is Developmentally Regulated and Forms a Homo-oligomeric Channel Blocked by Alpha-BTX," Neuron 5(6):847-856, Cell Press, United States (Dec. 1990).
Crouser, E., "Nicotine Treatment for Pulmonary Sarcoidosis: A Clinical Trial Pilot Study," Ohio State University, ClinicalTrials.gov Identifier: NCT02265874.
Cuesto, G., et al., "Molecular Bases of Anorexia Nervosa, Bulimia Nervosa and Binge Eating Disorder: Shedding Light on the Darkness," Journal of Neurogenetics 31(4):266-287, Informa Healthcare, England (Dec. 2017).
De Fiebre, N.C. and De Fiebre, M.C., "Alpha 7 Nicotinic Acetylcholine Receptor-mediated Protection Against Ethanol-induced Neurotoxicity," Alcohol 31(3):149-153, Elsevier Science, United States (Nov. 2003).
Delbono, O., et al., "Activation of the Recombinant Human Alpha 7 Nicotinic Acetylcholine Receptor Significantly Raises Intracellular Free Calcium," The Journal of Pharmacology and Experimental Therapeutics 280(1):428-438, American Society for Pharmacology and Experimental Therapeutics, United States (Jan. 1997).
Deutsch, S., et al., "Progressive Worsening of Adaptive Functions in Down Syndrome May be Mediated by the Complexing of Soluble Abeta Peptides With the Alpha 7 Nicotinic Acetylcholine Receptor: Therapeutic Implications," Clinical Neuropharmacology 26(5):277-283, Lippincott Williams & Wilkins, United States (Sep.-Oct. 2003).
Deutsch, S.I., et al., "Cholinergic Abnormalities in Autism: Is There a Rationale for Selective Nicotinic Agonist Interventions?," Clinical Neuropharmacology 33(3):114-120, Lippincott Williams & Wilkins, United States (May 2010).
Deutsch, S.I., et al., "Targeting alpha-7 Nicotinic Neurotransmission in Schizophrenia: A Novel Agonist Strategy," Schizophrenia Research 148(1-3):138-144, Elsevier Science Publisher, Netherlands (Aug. 2013).
Diaper, A., et al., "Pharmacological Strategies for Detoxification," British Journal of Clinical Pharmacology 77(2):302-314, Wiley-Blackwell, England (Feb. 2014).
Di Bari, M., et al., "Cholinergic System and Neuroinflammation: Implication in Multiple Sclerosis," Central Nervous System Agents in Medicinal Chemistry 17(2):109-115, Bentham Science Publishers, United Arab Emirates (2017).
Ebben, M.R. and Krieger, A.C., "Narcolepsy With Cataplexy Masked by the Use of Nicotine," Journal of Clinical Sleep Medicine 8(2):195-196, American Academy of Sleep Medicine, United States (Apr. 2012).
Enioutina, E.Y., et al., "The Nicotinic Receptor Alpha7 Impacts the Mouse Lung Response to Lps Through Multiple Mechanisms," PloS One 10(3):e0121128, Public Library of Science, United States (Mar. 2015).
Fairley, A.S. and Mathis, K.W., "Cholinergic Agonists Reduce Blood Pressure in a Mouse Model of Systemic Lupus Erythematosus," Physiological Reports 5(7):e13213, Wiley Periodicals, Inc, United States (Apr. 2017).

(56) References Cited

OTHER PUBLICATIONS

Fehér, A., et al., "Association Between a Genetic Variant of the Alpha-7 Nicotinic Acetylcholine Receptor Subunit and Four Types of Dementia," Dementia and Geriatric Cognitive Disorders 28(1):56-62, Basel, Switzerland (2009).
Foucault-Fruchard, L., et al., "Alpha-7 Nicotinic Acetylcholine Receptor Agonist Treatment in a Rat Model of Huntington's Disease and Involvement of Heme Oxygenase-1," Neural Regeneration Research 13(4):737-741, Wolters Kluwer Health, Medknow, India (Apr. 2018).
Francis, M., et al., "Specific Activation of the Alpha 7 Nicotinic Acetylcholine Receptor by a Quaternary Analog of Cocaine," Molecular Pharmacology 60(1):71-79, American Society for Pharmacology and Experimental Therapeutics, United States (Jul. 2001).
Gotti, C. and Clementi, F., "Neuronal Nicotinic Receptors: From Structure to Pathology," Progress in neurobiology 74(6):363-396, Pergamon Press, England (Dec. 2004).
Gundisch, D. and Eibl, C., "Nicotinic Acetylcholine Receptor Ligands, a Patent Review (2006-2011)," Expert Opinion on Therapeutic Patents 21(12):1867-1896, Informa Healthcare, England (Dec. 2011).
Han, Z., et al., "Alpha-7 Nicotinic Acetylcholine Receptor Agonist Treatment Reduces Neuroinflammation, Oxidative Stress, and Brain Injury in Mice With Ischemic Stroke and Bone Fracture," Journal of Neurochemistry 131(4):498-508, Wiley on behalf of the International Society for Neurochemistry, England (Nov. 2014).
Hao, J., et al., "Attenuation of CNS Inflammatory Responses by Nicotine Involves A7 and Non-α7 Nicotinic Receptors," Experimental Neurology 227(1):110-119, Academic Press, United States (Jan. 2011).
Ikonomovic, M., et al., "Cortical Alpha7 Nicotinic Acetylcholine Receptor and Beta-amyloid Levels in Early Alzheimer Disease," Archives of Neurology 66(5):646-651, American Medical Assn, United States (May 2009).
International Search Report and Written Opinion for International Application No. PCT/IB2019/055949, European Patent Office, Netherlands, dated Sep. 9, 2019.
Janowsky, D.S., et al., "A Cholinergic-adrenergic Hypothesis of Mania and Depression," Lancet 2(7778):632-635, Elsevier, England (Sep. 1972).
Kamens, H.M., et al., "Evidence for Association Between Low Frequency Variants in CHRNA6/CHRNB3 and Antisocial Drug Dependence," Behavior Genetics 46(5):693-704, Kluwer Academic/Plenum Publishers, United States (Sep. 2016).
Kawamata, J., et al., "Enhancement of Nicotinic Receptors Alleviates Cytotoxicity in Neurological Disease Models," Therapeutic Advances in Chronic Disease 2(3):197-208, SAGE Publications, United States (May 2011).
Keszthelyi, D., et al., "Understanding the Role of Tryptophan and Serotonin Metabolism in Gastrointestinal Function," Neurogastroenterology and Motility 21(12):1239-1249, Blackwell Scientific Publications, England (Dec. 2009).
Krahn, L.E., et al., "Narcoleptic Patients' Perceptions of Nicotine," Journal of Clinical Sleep Medicine 5(4):390, American Academy of Sleep Medicine, United States (Aug. 2009).
Lakhan, S.E. and Kirchgessner, A., "Anti-inflammatory Effects of Nicotine in Obesity and Ulcerative Colitis," Journal of Translational Medicine 9:129, BioMed Central, England (Aug. 2011).
Le Novere, N. and Changeux, J.P., "Molecular Evolution of the Nicotinic Acetylcholine Receptor: An Example of Multigene Family in Excitable Cells," Journal of Molecular Evolution 40(2):155-172, Springer-Verlag, Germany (Feb. 1995).
Lee, S.E., "Choline, an Alpha7 Nicotinic Acetylcholine Receptor Agonist, Alleviates Hyperalgesia in a Rat Osteoarthritis Model," Neuroscience Letters 548:291-295, Elsevier Scientific Publishers, Ireland (Aug. 2013).
Lendvai, B., et al., "Alpha7 Nicotinic Acetylcholine Receptors and Their Role in Cognition," Brain Research Bulletin 93:86-96, Elsevier Science, United States (Apr. 2013).

Leonard, S. and Freedman, R., "Genetics of Chromosome 15q13-q14 in Schizophrenia," Biological Psychiatry 60(2):115-122, Elsevier, United States (Jul. 2006).
Leppik, I.E., "Classification of the Myoclonic Epilepsies," Epilepsia 44 Suppl 11:2-6, Blackwell Science, United States (2003).
Leslie, F., et al., "Nicotinic Receptors in Addiction Pathways," Molecular Pharmacology 83(4):753-758, American Society for Pharmacology and Experimental Therapeutics, United States (Apr. 2013).
Lewis, A.S., et al., "Alpha-7 Nicotinic Agonists for Cognitive Deficits in Neuropsychiatric Disorders: A Translational Meta-analysis of Rodent and Human Studies," Progress in Neuro-psychopharmacology & Biological Psychiatry 75:45-53, Pergamon Press, England (Apr. 2017).
Liu, Q., et al., "α7 Nicotinic Acetylcholine Receptor-mediated Anti-inflammatory Effect in a Chronic Migraine Rat Model via the Attenuation of Glial Cell Activation," Journal of Pain Research 11:1129-1140, Dove Medical Press, New Zealand (Jun. 2018).
Mai, X.K., et al., "Modulation of Inflammatory Responses in Heart Failure via Activation of alpha-7 Nicotinic Acetylcholine Receptor Agonist GTS-21," The Journal of Immunology 200(1 Supplement):108.11, The American Association of Immunologists, Inc., United States (May 2018).
Maouche, K., et al., "Contribution of A7 Nicotinic Receptor to Airway Epithelium Dysfunction Under Nicotine Exposure," Proceedings of the National Academy of Sciences of the United States of America 110(10):4099-4104, National Academy of Sciences, United States (Mar. 2013).
Marrero, M.B., et al., "An Alpha7 Nicotinic Acetylcholine Receptor-selective Agonist Reduces Weight Gain and Metabolic Changes in a Mouse Model of Diabetes," The Journal of Pharmacology and Experimental Therapeutics 332(1):173-180, American Society for Pharmacology and Experimental Therapeutics, United States (Jan. 2010).
Martin, L.F., et al., "Sensory Gating and alpha-7 Nicotinic Receptor Gene Allelic Variants in Schizoaffective Disorder, Bipolar Type," American Journal of Medical Genetics 144B(5):611-614, Wiley-Blackwell, United States (Jul. 2007).
Mazloom, R., et al., "The Role of A7 Nicotinic Acetylcholine Receptor in Modulation of Heart Rate Dynamics in Endotoxemic Rats," PloS one 8(12):e82251, Public Library of Science, United States (Dec. 2013).
McNamara, J.P., et al., "Sleep Disturbances Associated With Cigarette Smoking," Psychology, Health & Medicine 19(4):410-419, Routledge, England (2014).
Minami, S., et al., "Reducing Inflammation and Rescuing Ftd-related Behavioral Deficits in Progranulin-deficient Mice With A7 Nicotinic Acetylcholine Receptor Agonists," Biochemical Pharmacology 97(4):454-462, Elsevier Science, England (Oct. 2015).
Mineur, Y.S., et al., "Multiple Nicotinic Acetylcholine Receptor Subtypes in the Mouse Amygdala Regulate Affective Behaviors and Response to Social Stress," Neuropsychopharmacology 41(6):1579-1587, Nature Publishing Group, England (May 2016).
Parameswaran, N., et al., "Nicotine Treatment Reduces L-dopa-induced Dyskinesias in MPTP-treated Squirrel Monkeys," Society for Neuroscience Abstracts (2007).
Perry, E.K., et al., "Alteration in Nicotine Binding Sites in Parkinson's Disease, Lewy Body Dementia and Alzheimer's Disease: Possible Index of Early Neuropathology," Neuroscience 64(2):385-395, Elsevier Science, United States (Jan. 1995).
Philip, N.S., et al., "Nicotinic Acetylcholine Receptors and Depression: a Review of the Preclinical and Clinical Literature," Psychopharmacology 212(1):1-12, Springer-Verlag, Germany (Sep. 2010).
Picciotto, M.R., et al., "Mood and Anxiety Regulation by Nicotinic Acetylcholine Receptors: a Potential Pathway to Modulate Aggression and Related Behavioral States," Neuropharmacology 96(Pt B):235-243, Pergamon Press, England (Sep. 2015).
Pubill, D., et al., "Neuronal Nicotinic Receptors as New Targets for Amphetamine-Induced Oxidative Damage and Neurotoxicity," Pharmaceuticals 4(6):822-847, Basel, Switzerland (2011).
Purves, D., et al., "Neuroscience," 4th ed., pp. 122-126 (2008).
Putignano, S., et al., "Retrospective and Observational Study to Assess the Efficacy of Citicoline in Elderly Patients Suffering From

(56) References Cited

OTHER PUBLICATIONS

Stupor Related to Complex Geriatric Syndrome," Clinical Interventions in Aging 7:113-118, Dove Medical Press, New Zealand (2012).
Quik, M., et al., "Alpha7 nicotinic receptors as therapeutic targets for Parkinson's disease," Biochemical Pharmacology 97(4):399-407, Elsevier Science, England (Oct. 2015).
Rautio, J., et al., "Prodrugs: Design and Clinical Applications," Nature Reviews. Drug Discovery 7(3):255-270, Nature Publishing Group, England (Mar. 2008).
Ren, C., et al., "Activation of Central Alpha 7 Nicotinic Acetylcholine Receptor Reverses Suppressed Immune Function of T Lymphocytes and Protects Against Sepsis Lethality," International Journal of Biological Sciences 14(7):748-759, Ivyspring International, Australia (May 2018).
Rowe, A.R., et al., "Dementia Praecox Redux: A Systematic Review of the Nicotinic Receptor as a Target for Cognitive Symptoms of Schizophrenia," Journal of Psychopharmacology 29(2):197-211, Sage Publications, United States (Feb. 2015).
Salaga, M., et al., "Encenicline, an α7 Nicotinic Acetylcholine Receptor Partial Agonist, Reduces Immune Cell Infiltration in the Colon and Improves Experimental Colitis in Mice," The Journal of Pharmacology and Experimental Therapeutics 356(1):157-169, American Society for Pharmacology and Experimental Therapeutics, United States (Jan. 2016).
Santana, F.P.R., et al., "Alpha-7 Nicotinic Receptor Stimulation Reduces Airway Inflammation in a Murine Model of Asthma," European Respiratory Journal 48(suppl 60): PA5066, European Respiratory Society, Switzerland (Nov. 2016).
Sfera, A., et al., "Non-Neuronal Acetylcholine: The Missing Link Between Sepsis, Cancer, and Delirium?," Frontiers in Medicine 2:56, Frontiers Media, Switzerland (Aug. 2015).
Shan, Z.Y., et al., "Progressive Brain Changes in Patients With Chronic Fatigue Syndrome: a Longitudinal MRI Study," Journal of Magnetic Resonance Imaging44(5):1301-1311, Wiley-Liss, United States (Nov. 2016).
Shi, M., et al., "Identification of Redeye, a New Sleep-regulating Protein Whose Expression is Modulated by Sleep Amount," eLife 3:e01473, eLife Sciences Publications, England (2014).
Shin, S.S. and Dixon, E., "Targeting A7 Nicotinic Acetylcholine Receptors: a Future Potential for Neuroprotection From Traumatic Brain Injury," Neural Regeneration Research 10(10):1552-1554, Wolters Kluwer Health, Medknow, India (Oct. 2015).
Shytle, R.D., et al., "Neuronal Nicotinic Receptor Inhibition for Treating Mood Disorders: Preliminary Controlled Evidence With Mecamylamine," Depression and Anxiety 16(3):89-92, Wiley, United States (2002).
Si, M.L. and Lee, T.J.F., Alpha7-nicotinic Acetylcholine Receptors on Cerebral Perivascular Sympathetic Nerves Mediate Choline-induced Nitrergic Neurogenic Vasodilation, Circulation Research 91(1):62-69, Lippincott Williams & Wilkins, United States (Jul. 2002).
Solinas, M., et al., "Nicotinic Alpha 7 Receptors as a New Target for Treatment of Cannabis Abuse," The Journal of Neuroscience 27(21):5615-5620, Society for Neuroscience, United States (May 2007).
Somm, E., "Nicotinic Cholinergic Signaling in Adipose Tissue and Pancreatic Islets Biology: Revisited Function and Therapeutic Perspectives," Archivum Immunologiae Et Therapiae Experimentalis 62(2):87-101, Birkhauser, Switzerland (Apr. 2014).
Sun, R., et al., "Spinal Activation of Alpha7-nicotinic Acetylcholine Receptor Attenuates Posttraumatic Stress Disorder-related Chronic Pain via Suppression of Glial Activation," Neuroscience 344:243-254, Elsevier Science, United States (Mar. 2017).
Taslim, N., et al., "Role of Mouse Cerebellar Nicotinic Acetylcholine Receptor (Nachr) A(4)B(2)- and A(7) Subtypes in the Behavioral Cross-tolerance Between Nicotine and Ethanol-induced Ataxia," Behavioural Brain Research 217(2):282-292, Elsevier/North-Holland Biomedical Press, Netherlands (Mar. 2011).

Terry, A.V. and Gearhart, D.A., "Time Dependent Decreases in Central Alpha7 Nicotinic Acetylcholine Receptors Associated With Haloperidol and Risperidone Treatment in Rats," European Journal of Pharmacology 571(1):29-32, Elsevier Science, Netherlands (Sep. 2007).
Thomsen, M.S., et al., "Alpha(7) Nicotinic Acetylcholine Receptor Activation Prevents Behavioral and Molecular Changes Induced by Repeated Phencyclidine Treatment," Neuropharmacology 56(6-7):1001-1009, Pergamon Press, England (May-Jun. 2009).
Thomsen, M.S., et al., "Cognitive Improvement by Activation of alpha7 Nicotinic Acetylcholine Receptors: From Animal Models to Human Pathophysiology," Current Pharmaceutical Design 16(3):323-343, Bentham Science Publishers, United Arab Emirates (Jan. 2010).
Tizabi, Y., et al., "Effect of Nicotine on Quinpirole-induced Checking Behavior in Rats: Implications for Obsessive-compulsive Disorder," Biological Psychiatry 51(2):164-171, Elsevier, United States (Jan. 2002).
Van Maanen, M.A., et al., "The Alpha7 Nicotinic Acetylcholine Receptor on Fibroblast-like Synoviocytes and in Synovial Tissue From Rheumatoid Arthritis Patients: a Possible Role for a Key Neurotransmitter in Synovial Inflammation," Arthritis and Rheumatism 60(5):1272-1281, Wiley-Blackwell, United States (May 2009).
Warren, N.M., et al., "Cholinergic Systems in Progressive Supranuclear Palsy," Brain 128(Pt 2):239-249, Oxford University Press, England (Feb. 2005).
Westman, M., et al., "Cell Specific Synovial Expression of Nicotinic Alpha 7 Acetylcholine Receptor in Rheumatoid Arthritis and Psoriatic Arthritis," Scandinavian Journal of Immunology 70(2):136-140, Blackwell Scientific Publications, England (Aug. 2009).
Whitehouse, P.J., et al., "Alzheimer's Disease and Senile Dementia: Loss of Neurons in the Basal Forebrain," Science 215(4537):1237-1239, American Medical Assn, United States (Mar. 1982).
Wilens, T.E. and Decker, M.W., "Neuronal Nicotinic Receptor Agonists for the Treatment of Attention-deficit/hyperactivity Disorder: Focus on Cognition," Biochemical Pharmacology 74(8):1212-1223, Elsevier Science, England (Oct. 2007).
Yamamoto, T., et al., "Anti-allergic Role of Cholinergic Neuronal Pathway via A7 Nicotinic Ach Receptors on Mucosal Mast Cells in a Murine Food Allergy Model," PloS one 9(1):e85888, Public Library of Science, United States (Jan. 2014).
Zhang, W., et al., "Activation of Spinal Alpha-7 Nicotinic Acetylcholine Receptor Attenuates Remifentanil-induced Postoperative Hyperalgesia," International Journal of Clinical and Experimental Medicine 8(2):1871-1879, e-Century Pub. Corp., United States (Feb. 2015).
Zimmerman, C.N., et al., "Evaluation of AZD1446 as a Therapeutic in DYT1 Dystonia," Frontiers in Systems Neuroscience 11:43, Frontiers Research Foundation, Switzerland (Jun. 2017).
Zvolensky, M.J., et al., "Smoking and Panic Attacks, Panic Disorder, and Agoraphobia: a Review of the Empirical Literature," Clinical Psychology Review 25(6):761-789, Elsevier Science, United States (Sep. 2005).
Spence, K.W., and Lippitt, R., "An experimental test of the sign-gestalt theory of trial and error learning," J Exp Psychol 36(6):491-502, American Psychological Association, United States (1946).
Dember, W.N., and Fowler, H., "Spontaneous alternation after free and forced trials," Can J Psychol 13(3):151-154, Sage Publications, United States (Sep. 1959).
Lalonde, R., "The neurobiological basis of spontaneous alternation," Neurosci Biobehav Rev 26(1):91-104, Elsevier, United Kingdom (Jan. 2002).
Powell, C.M., and Miyakawa, T., "Schizophrenia-relevant behavioral testing in rodent models: a uniquely human disorder?," Biol Psychiatry 59(12):1198-1207, Elsevier USA, United States (Jun. 2006).
Jones, C.A., et al., "Animal models of schizophrenia," Br J Pharmacol 164(4):1162-1194, Wiley-Blackwell, United States (Oct. 2011).
Young, J.W., et al., "Using the MATRICS to guide development of a preclinical cognitive test battery for research in schizophrenia," Pharmacol Ther 122(2):150-202, Elsevier USA, United States (May 2009).

(56) References Cited

OTHER PUBLICATIONS

Yu, T., et al., "Cognitive and neural correlates of depression-like behaviour in socially defeated mice: an animal model of depression with cognitive dysfunction," Int J Neuropsychopharmacol 14(3):303-317, Oxford University Press, United Kingdom (Apr. 2011).
Database Registry [online], Chemical Abstracts Service, Columbus, Ohio, CAS Registry No. 902878-05-1, Entered STN Aug. 21, 2006, retrieved from STN CAS, 1 pg.
Database Registry [online], Chemical Abstracts Service, Columbus, Ohio, CAS Registry No. 902878-13-1, Entered STN Aug. 21, 2006, retrieved from STN CAS, 1 pg.
Database Registry [online], Chemical Abstracts Service, Columbus, Ohio, CAS Registry No. 902878-15-3, Entered STN Aug. 21, 2006, retrieved from STN CAS, 1 pg.
Database Registry [online], Chemical Abstracts Service, Columbus, Ohio, CAS Registry No. 902878-19-7, Entered STN Aug. 21, 2006, retrieved from STN CAS, 1 pg.
Database Registry [online], Chemical Abstracts Service, Columbus, Ohio, CAS Registry No. 902878-23-3, Entered STN Aug. 21, 2006, retrieved from STN CAS, 1 pg.
Database Registry [online], Chemical Abstracts Service, Columbus, Ohio, CAS Registry No. 902878-27-7, Entered STN Aug. 21, 2006, retrieved from STN CAS, 1 pg.
Database Registry [online], Chemical Abstracts Service, Columbus, Ohio, CAS Registry No. 902878-29-9, Entered STN Aug. 21, 2006, retrieved from STN CAS, 1 pg.
Database Registry [online], Chemical Abstracts Service, Columbus, Ohio, CAS Registry No. 902878-31-3, Entered STN Aug. 21, 2006, retrieved from STN CAS, 1 pg.
Database Registry [online], Chemical Abstracts Service, Columbus, Ohio, CAS Registry No. 902878-33-5, Entered STN Aug. 21, 2006, retrieved from STN CAS, 1 pg.
Database Registry [online], Chemical Abstracts Service, Columbus, Ohio, CAS Registry No. 1015883-88-1, Entered STN Apr. 20, 2008, retrieved from STN CAS, 1 pg.
Database Registry [online], Chemical Abstracts Service, Columbus, Ohio, CAS Registry No. 1381708-74-2, Entered STN Jul. 5, 2012, retrieved from STN CAS, 1 pg.
Database Registry [online], Chemical Abstracts Service, Columbus, Ohio, CAS Registry No. 1381561-03-0, Entered STN Jul. 5, 2012, retrieved from STN CAS, 1 pg.
Database Registry [online], Chemical Abstracts Service, Columbus, Ohio, CAS Registry No. 1381519-24-9, Entered STN Jul. 5, 2012, retrieved from STN CAS, 1 pg.
Database Registry [online], Chemical Abstracts Service, Columbus, Ohio, CAS Registry No. 1381449-51-9, Entered STN Jul. 4, 2012, retrieved from STN CAS, 1 pg.
Database Registry [online], Chemical Abstracts Service, Columbus, Ohio, CAS Registry No. 1381423-92-2, Entered STN Jul. 4, 2012, retrieved from STN CAS, 1 pg.
Database Registry [online], Chemical Abstracts Service, Columbus, Ohio, CAS Registry No. 1381388-23-3, Entered STN Jul. 4, 2012, retrieved from STN CAS, 1 pg.
Database Registry [online], Chemical Abstracts Service, Columbus, Ohio, CAS Registry No. 1381322-24-2, Entered STN Jul. 4, 2012, retrieved from STN CAS, 1 pg.
Database Registry [online], Chemical Abstracts Service, Columbus, Ohio, CAS Registry No. 1240163-09-0, Entered STN Sep. 7, 2010, retrieved from STN CAS, 1 pg.
Database Registry [online], Chemical Abstracts Service, Columbus, Ohio, CAS Registry No. 1240145-90-7, Entered STN Sep. 7, 2010, retrieved from STN CAS, 1 pg.
Database Registry [online], Chemical Abstracts Service, Columbus, Ohio, CAS Registry No. 1173753-05-3, Entered STN Aug. 10, 2009, retrieved from STN CAS, 1 pg.
Database Registry [online], Chemical Abstracts Service, Columbus, Ohio, CAS Registry No. 950437-84-0, Entered STN Oct. 12, 2007, retrieved from STN CAS, 1 pg.
Database Registry [online], Chemical Abstracts Service, Columbus, Ohio, CAS Registry No. 945129-49-7, Entered STN Aug. 21, 2007, retrieved from STN CAS, 1 pg.
Database Registry [online], Chemical Abstracts Service, Columbus, Ohio, CAS Registry No. 902879-56-5, Entered STN Aug. 21, 2006, retrieved from STN CAS, 1 pg.
Database Registry [online], Chemical Abstracts Service, Columbus, Ohio, CAS Registry No. 902878-84-6, Entered STN Aug. 21, 2006, retrieved from STN CAS, 1 pg.

\* cited by examiner

THIADIAZINE DERIVATIVES

FIELD OF THE INVENTION

The present invention relates to pharmacologically active thiadiazine compounds, or pharmaceutically acceptable salts, biologically active metabolites, pro-drugs, racemates, enantiomers, diastereomers, solvates and hydrates thereof, as well as to pharmaceutical compositions containing them and to their use as modulators of α7 nicotinic acetylcholine receptor activity in a mammalian subject.

BACKGROUND OF THE INVENTION

Acetylcholine (ACh) exerts its functions as a neurotransmitter in the mammalian central nervous system (CNS) by binding to cholinergic receptors. The mammalian CNS contains two predominant types of ACh receptors: muscarinic (mAChR) and nicotinic (nAChR) receptors, based on the agonist activities of muscarine and nicotine, respectively. Nicotinic acetylcholine receptors are ligand-gated ion channels made up of five subunits (Purves et al. *Neuroscience* 4$^{th}$ ed. (2008) 122-126). The subunits of the nicotinic receptors belong to a multigene family and have been divided into two groups based on their amino acid sequences; one containing alpha, and another containing beta subunits. Pentameric assemblies of different subunit combinations result in large number of receptor subtypes with various pharmacological properties. Assembly of the most broadly expressed subtypes include muscle-type (($\alpha 1$)$_2 \beta_1 \delta_\epsilon$), ganglion-type (($\alpha 3$)$_2$ ($\beta 4$)$_3$) and CNS-type ($(\alpha 4)_2 (\beta 2)_3$ or $(\alpha 7)_5$) nAChR subtypes (Le Novère N et al. *Journal of Molecular Evolution* 40 (1995) 155-172). α7 subunits have been shown to form functional receptors when expressed alone, and thus are presumed to form homooligomeric pentameric receptors.

Activation of the nAChR ion channel is primarily controlled by binding of ligands at conventional agonist binding sites, but is also regulated by either negative, or positive allosteric modulators (NAMs and PAMs). The allosteric transition state model of the nAChR involves at least a resting state, an activated state and a "desensitized" closed channel state, a process by which receptors become insensitive to the agonist. Different nAChR ligands can stabilize the conformational state of a receptor, to which they preferentially bind. For example, the agonists ACh and (−)-nicotine respectively stabilize the active and desensitized states. Changes of the activity of nicotinic receptors have been implicated in a number of diseases. Reductions in nicotinic receptors have been hypothesized to mediate cognitive deficits seen in diseases, such as Alzheimer's disease and schizophrenia. The effects of nicotine from tobacco are also mediated by nicotinic receptors, and since the effect of nicotine is to stabilize receptors in a desensitized state, an increased activity of nicotinic receptors may reduce the desire to smoke.

However, treatment with nicotinic receptor agonists, which act at the same site as ACh is problematic, because ACh not only activates, but also blocks receptor activity through processes, which include desensitization and uncompetitive blockade. Furthermore, prolonged activation appears to induce a long-lasting inactivation. Therefore, agonists of ACh can be expected to lose effectiveness upon chronic administration.

While the α7 nAChR is characterized by its fast activation kinetics and high permeability to Ca$^{2+}$ compared to other subtypes (Delbono et al. *J. Pharmacol. Exp. Ther.* 280 (1997) 428-438), it also exhibits rapid desensitization following exposure to agonists at the orthosteric site (Castro et al. *Neurosci. Lett.* 164 (1993) 137-140; Couturier et al. *Neuron* S (1990) 847-856). In spite that development of a variety of α7-selective agonists and partial agonists has been carried out in the recent years, their clinical efficacy proved to be suboptimal, due to this receptor blockade (desensitisation) following the agonist activation. This problem may be overcome by treatment with PAMs, enhancing α7 nAChR activation mediated by the endogenous agonist. The positive modulation of α7 nAChRs has been shown to have cognitive benefits in various preclinical models (Thomsen et al. *Curr Pharm Des* 16 (2010) 323-343; Lendvai et al. *Brain Res Bull* 93 (2013) 86-96).

The compounds of the present invention may be useful for the treatment of diseases and conditions mediated by, or associated to the positive allosteric modulation of the α7 nAChR, including, but not limited to psychotic disorders, for example schizophrenia (Deutsch S I et al. *Schizophr Res* 148 (2013) 138-144), schizophreniform disorder (Rowe A R et al. *J Psychopharmacol* 29 (2015) 197-211), schizoaffective disorder (Martin L F et al. *Am J Med Genet B Neuropsychiatr Genet* 144B (2007) 611-614), delusional disorder (Carson R et al. *Neuromolecular Med* 10 (2008) 377-384), brief psychotic disorder, psychotic disorder due to a general medical condition, substance-induced psychotic disorder, or psychotic disorder not otherwise specified, cognitive impairment including, for example the treatment of impairment of cognitive functions, as well as cognitive impairment as a result of stroke, Alzheimer's disease (Lewis A S et al. *Prog Neuropsychopharmacol Biol Psychiatry* 75 (2017) 45-53), Huntington's disease (Foucault-Fruchard L et al. *Neural Regen Res* 13 (2018) 737-741), Pick disease (Fehér A et al. *Dement Geriatr Cogn Disord* 28 (2009) 56-62), HIV associated dementia (Capó-Vélez C M et al. *Sci Rep* 8 (2018) 1829), frontotemporal dementia (Minami S S et al. *Biochem Pharmacol* 97 (2015) 454-462), Lewy body dementia (Perry E K et al. *Neuroscience* 64 (1995) 385-395), vascular dementia (Putignano S et al. *Clin Interv Aging* 7 (2012) 113-118), cerebrovascular disease (Si M L and Lee T J F *Circ Res* 91 (2002) 62-69) or other dementia states, and dementia associated to other degenerative disorders (amyotrophic lateral sclerosis (Kawamata et al. *Ther Adv Chronic Dis* 2 (2011) 197-208), etc.), other acute or sub-acute conditions that may cause cognitive decline such as delirium (Sfera A et al. *Front Med* 2 (2015) 56), traumatic brain injury (Shin S S et al. *Neural Regen Res* 10 (2015) 1552-1554), senile dementia (Whitehouse P J et et al. *Science* 215 (1982) 1237-1239), mild cognitive impairment (Ikonomovic M D et al. *Arch Neurol* 66 (2009) 646-651), Down's syndrome (Deutsch S I et al. *Clin Neuropharmacol* 26 (2003) 277-283), depression and cognitive deficit related to other diseases and dyskinetic disorders (Parameswaran N et al. *Soc Neurosci Abstr* (2007)), such as Parkinson's disease (Quik M et al. *Biochem Pharmacol* 97 (2015) 399-407), as well as neuroleptic-induced parkinsonism, or tardive dyskinesias (Terry A V and Gearhart D A *Eur J Pharmacol* 571 (2007) 29-32), depression and mood disorders, including depressive disorders and episodes (Philip N S et al. *Psychopharmacology* 212 (2010) 1-12), bipolar disorders (Leonard S and Freedman R. *Biol Psychiatry* 60 (2006) 115-122), cyclothymic disorder (Ancin I et al. *J Affect Disord* 133 (2011) 340-345), and bipolar disorder not otherwise specified, other mood disorders (Shytle R D et al. *Depression and Anxiety* 16 (2002) 89-92), substance-induced mood disorder, and mood disorder not otherwise specified, anxiety disorders (Picciotto M R et al. *Neuropharmacology* 96 (2015) 235-243), panic disorder and panic attacks (Zvolensky M J et al.

Clin Psychol Rev 25 (2005) 761-789), obsessive compulsive disorder (Tizabi Y et al. *Biol Psychiatry* 51 (2002) 164-171), posttraumatic stress disorder (Sun R et al. *Neuroscience* 344 (2017) 243-254), acute stress disorder (Mineur Y S et al. *Neuropsychopharmacology* 41 (2015) 1579-1587), generalized anxiety disorder (Cocores J A *Prim Care Companion J Clin Psychiatry* 10 (2008) 253-254), anxiety disorder due to a general medical condition, substance-induced anxiety disorder, phobias, and anxiety disorder not otherwise specified, substance related disorders for example substance use or substance-induced disorders, e.g., alcohol- (de Fiebre N C and de Fiebre C M *Alcohol* 31 (2003) 149-153; Diaper A M et al. *Br J Clin Pharmacol* 77 (2014) 302-314) nicotine- (Leslie F M et al. *Mol Pharmacol* 83 (2013) 753-758), amphetamine- (Pubill D et al. *Pharmaceuticals* 4 (2011) 822-847), phencyclidine-(Thomsen M S et al. *Neuropharmacology* 56 (2009) 1001-1009), opioid-(Zhang W, *Int J Clin Exp Med* 8 (2015) 1871-1879), cannabis-(Solinas M et al. *J Neurosci* 27 (2007) 5615-5620), cocaine- (Francis M M et al. *Mol Pharmacol* 60 (2001) 71-79), caffeine-, hallucinogen-, inhalant-, sedative-, hypnotic-, anxiolytic-, polysubstance- or other substance-related disorders, sleep disorders (McNamara J P et al. *Psychol Health Med* 19 (2014) 410-419), such as narcolepsy (Krahn et al *J Clin Sleep Med* 5 (2009) 390), dyssomnias, primary hypersomnia, breathing-related sleep disorders, circadian rhythm sleep disorder, and dyssomnia not otherwise specified, parasomnias, sleep terror disorder, sleepwalking disorder, and parasomnia not otherwise specified, sleep disorders related to another mental disorder (including, insomnia related to another mental disorder and hypersomnia related to another mental disorder), sleep disorder due to a general medical condition and substance-induced sleep disorder, metabolic and eating disorders (Somm E *Arch Immunol Ther Exp* 62 (2014) 62: 87-101), such as anorexia nervosa (Cuesto G et al. *J Neurogenet* 31 (2017) 266-287), bulimia nervosa, obesity (Lakhan S E and Kirchgessner A *J Transl Med* 9 (2011) 129-139), compulsive eating disorder, binge eating disorder, and eating disorder not otherwise specified, diabetes mellitus (Marrero M B et al. *J Pharmacol Exp Ther* 332 (2010) 173-180), ulcerative colitis (Salaga et al. *JPET* 356 (2016) 157-169), Crohn's disease (Bencherif M et al. *Cell Mol Life Sci* 68 (2011) 931-949), irritable bowel syndrome (Keszthelyi D et al. *Neurogastroenerol Motil* 21 (2009) 1239-1249), autism spectrum disorders (Deutsch et al. *Clin Neuropharmacol* 33 (2010) 114-120), including autistic disorder, Asperger's disorder, Rett's disorder, childhood disintegrative disorder and pervasive developmental disorder not otherwise specified, attention deficit hyperactivity disorder (Wilens T E and Decker M W *Biochem Pharmacol* 74 (2007) 1212-1223), disruptive behaviour disorders, oppositional defiant disorder, and disruptive behaviour disorder not otherwise specified, and tic disorders such as Tourette's disorder (Gotti C and Clementi F *Prog Neurobiol* 74 (2004) 363-396), personality disorders (Kamens H M et al. *Behav Genet* 46 (2016) 693-704), sexual dysfunctions, such as sexual desire disorders, sexual arousal disorders, orgasmic disorders, sexual pain disorder, sexual dysfunction not otherwise specified, paraphilias, gender identity disorders, infertility (Bray C et al. *Biol Reprod* 73 (2005) 807-814), premenstrual syndrome (Gündisch D and Eibl C *Expert Opin Ther Pat* 21 (2011) 1867-1896), and sexual disorders not otherwise specified, disorders of the respiratory system like cough (Canning B J *Am J Respir Crit Care Med* 195 (2017) A4498), asthma (Santana F P R et al. *Eur Respir J* 148 (2016) PA5066), chronic obstructive pulmonary disease (Maouche K et al. *Proc Natl Acad Sci USA* 110 (2013) 4099-4104), lung inflammation (Enioutina E Y et al. *PLoS One* 10 (2015) e0121128), disorders of the cardiovascular system such as cardiac failure (Mai X K et al. *J Immunol* 200 (2018) 108.11), heart arrhythmia (Mazloom R et al. *PLoS One* 8 (2013) e82251), and hypertension (Chen J K et al. *BMC Cardiovasc Disord* 12 (2012) 38).

The compounds of the invention are also useful in treating inflammation, inflammatory and neuropathic pain (Alsharari S D et al. *Biochem Pharmacol* 86 (2013) 1201-1207), rheumatoid arthritis (van Maanen M A et al. *Arthritis & Rheumatism* 60 (2009) 1272-1281), osteoarthritis (Lee S E *Neurosci Lett* 548 (2013) 291-295), allergy (Yamamoto T et al. *PLoS One* 9 (2014) e85888), sarcoidosis (Nicotine Treatment for Pulmonary Sarcoidosis: A Clinical Trial Pilot Study Elliott Crouser M D, Principal Investigator, Ohio State University ClinicalTrials.gov Identifier: NCT02265874), psoriasis (Westman M et al. *Scand J Immunol* 70 (2009) 136-140), ataxia (Taslim N et al. *Behav Brain Res* 217 (2011) 282-292), dystonia (Zimmerman C N et al. *Front Syst Neurosci* 11 (2017) 43), systemic lupus erythematosus (Fairley A S and Mathis K W *Physiol Rep* 5 (2017) e13213), mania (Janowsky D S et al. *Lancet* 2 (1972) 632-635), restless legs syndrome (Buchfuhrer M J *Neurotherapeutics* 9 (2012) 776-790), progressive supranuclear palsy (Warren N M et al. *Brain* 128 (2005) 239-245), epilepsy (Bertrand D *Epilepsy, Curr* 2 (2002) 191-193), myoclonus (Leppik I E *Epilepsia* 44 (2003) 2-6), migraine (Liu Q et al. *J Pain Res* 11 (2018) 1129-1140), amnesia (Bali Zs K et al. *Front Cell Neurosci* 11 (2017) 271), chronic fatigue syndrome (Shan Z Y et al. *J Magn Reson Imaging* 44 (2016) 1301-1311), cataplexy (Ebben M R and Krieger A C *J Clin Sleep Med* 8 (2012) 195-196), brain ischemia (Han Z et al. *J Neurochem* 131 (2014) 498-508), multiple sclerosis (Di Bari M et al. *Cent Nerv Syst Agents Med Chem* 17 (2017) 109-115), encephalomyelitis (Hao J et al. *Exp Neurol* 227 (2011): 110-119), jetlag (Shi M et al. *eLife* 3 (2014) e01473), cerebral amyloid angiopathy (Clifford P M et al. *Brain Res* 1234 (2008) 158-171), sepsis (Ren C et al. *Int J Biol Sci* 14 (2018) 748-759), and in general, in treating all types of diseases and disorders connected to the positive allosteric modulation of the α7 nAChR.

Furthermore, these compounds can also be combined with other therapeutic agents including, but not limited to acetylcholinesterase inhibitors (such as galantamine, rivastigmine, donepezil, tacrine, phenserine, ladostigil and ABT-089); NMDA receptor agonists or antagonists (such as memantine, neramexane, EVT101, and AZD4282); anti-amyloid antibodies including anti-amyloid humanized monoclonal antibodies (such as bapineuzumab, ACCOO1, CAD 106, AZD3102, H12A11V1); beta- (such as verubecestat, and AZD3293) or gamma-secretase inhibitors (such as LY450139 and TAK 070) or modulators; tau phosphorylation inhibitors; ApoE4 conformation modulators; p25/CDK5 inhibitors; NK1/NK3 receptor antagonists; COX-2 inhibitors (such as celecoxib, rofecoxib, valdecoxib, 406381 and 644784); LRRK2 inhibitors; HMG-CoA reductase inhibitors; NSAIDs (such as ibuprofen); vitamin E; glycine transport inhibitors; glycine site antagonists (such as lacosamide); LXR β agonists; androgen receptor modulators; blockers of Aβ oligomer formation; NR2B antagonists, anti-inflammatory compounds (such as (R)-flurbiprofen, nitroflurbiprofen, ND-1251, VP-025, HT-0712, and EHT-202); PPAR gamma agonists (such as pioglitazone and rosiglitazone); CB-1 receptor antagonists or inverse agonists (such as AVE1625): CB-2 agonists (such as 842166 and SAB378); VR-1 antagonists (such as AMG517, 705498, 782443, PAC20030, VI 14380 and A425619); bradykinin B1 receptor antagonists (such as SSR240612 and NVP-SAA164); sodium channel blockers and antagonists (such as VX409 and SPI860); NOS inhibitors (such as SD6010 and 274150); antibiotics; growth hormone secretagogues (such as ibutamoren, ibutamoren mesylate, and capromorelin); potassium channel openers; AMPA agonists or AMPA modulators (such as CX-717, LY 451395, LY404187 and S-18986); GSK3 inhibitors (such as AZD1080, SAR502250 and CEP16805); neuronal nicotinic agonists; MARK ligands; $M_1$ or $M_4$ mAChR agonists or PAMs; mGluR2 antagonists or NAMs or PAMs; mGluR5 antagonists (such as AZD9272); alpha-adrenerg agonists; ADAM-10 ligands; sedatives, hypnotics, anxiolytics, antipsychotics, cyclopyrrolones, imidazopyridines, pyrazolopyrimidines, minor tranquilizers, melatonin agonists and antagonists, melatonergic agents; orexin antagonists and agonists; prokineticin agonists and antagonists; T-type calcium channel antagonists; triazolopyridines benzodiazepines, barbiturates; $5-HT_{1A}$ antagonists (such as lecozotan); $5-HT_2$ antagonists; $5-HT_4$ agonists (such as PRX-03140); 5-HT, antagonists (such as GSK 742467, SGS-518, FK-962, SL-65.0155, SRA-333 and xaliproden); histamine H3 receptor antagonists and inverse agonists (such as S38093, ABT-834, ABT 829, GSK 189254 and CEP16795); $PDE_4$ inhibitors (such as HT0712); $PDE_9$ inhibitors (such as BI40936); $PDE_{10}$ inhibitors; HDAC inhibitors; KCNQ antagonists; $GABA_A$ inverse agonists; GABA signalling enhancers; GABA agonists, $GABA_A$ receptor alpha5 subunit NAMs or PAMs, antipsychotics; MAO-B inhibitors; dopamine transport inhibitors; noradrenaline transport inhibitors; $D_2$ agonists and partial agonists; anticholinergics (such as biperiden); COMT inhibitors (such as entacapone); A2a adenosine receptor antagonists; cholinergic agonists; compounds from the phenothiazine, thioxanthene (such as chlorprothixene and thiothixene), heterocyclic dibenzazepine (such as clozapine), butyrophenone (such as haloperidol), diphenylbutylpiperidine (such as pimozide) and indolone (such as molindolone) classes of neuroleptic agents; loxapine, sulpiride and risperidone; levodopa; calcium channel blockers (such as ziconotide and NMED160); MMP inhibitors; thrombolytic agents; opioid analgesics (such as codeine, fentanyl, hydromorphone, levorphanol, meperidine, methadone, morphine, oxycodone, oxymorphone, pentazocine, propoxyphene); pramipexole; ropinirole; neutrophil inhibitory factor; SSRIs or SSNRIs; tricyclic antidepressant drugs; norepinephrine modulators; lithium; valproate; gabapentin; pregabalin; rizatriptan; zolmitriptan; naratriptan and sumatriptan or other drugs that affect receptors or enzymes that either increase the efficacy, safety, convenience, or reduce unwanted side effects or toxicity of the compounds of the present invention.

Known positive allosteric modulators of the α7 nicotinic acetylcholine receptor include 2-aniline-4-aryl thiazole derivatives (WO 2007/031440 A2, JANSSEN PHARMACEUTICA NV), amide derivatives (WO 2009/100294 A2, ABBOT LAB.), trisubstituted 1,2,4-triazoles (WO 2009/115547 A1, JANSSEN PHARMACEUTICA NV), indole derivatives (WO 2009/127678 A1, GLAXO GROUP LTD. and WO 2009/127679 A1, GLAXO GROUP LTD.), tetrazole-substituted aryl amide derivatives (WO 2009/043780 A1, HOFFMANN LA ROCHE), cyclopropyl aryl amide derivatives (WO 2009/043784 A1, HOFFMANN LA ROCHE), trisubstituted pyrazoles (WO 2009/135944 A1, JANSSEN PHARMACEUTICA NV), pyrrole derivatives (WO 2014/141091 A1, LUPIN LTD), cyclopropylbenzene derivatives (WO 2017/165256 A1, MERCK SHARP & DOHME CORP.), and substituted bicyclic heteroaryl derivatives (WO 2018/085171 A1, MERCK SHARP & DOHME CORP.).

The present invention is directed to a novel class of compounds that exhibit positive allosteric modulation of the α7 nicotinic acetylcholine receptor.

BRIEF DESCRIPTION OF THE DRAWINGS

An exemplary embodiment of the present invention is illustrated by way of example in the accompanying drawings in which like reference numbers indicate the same or similar elements and in which.

SUMMARY OF THE INVENTION

Figure 1:
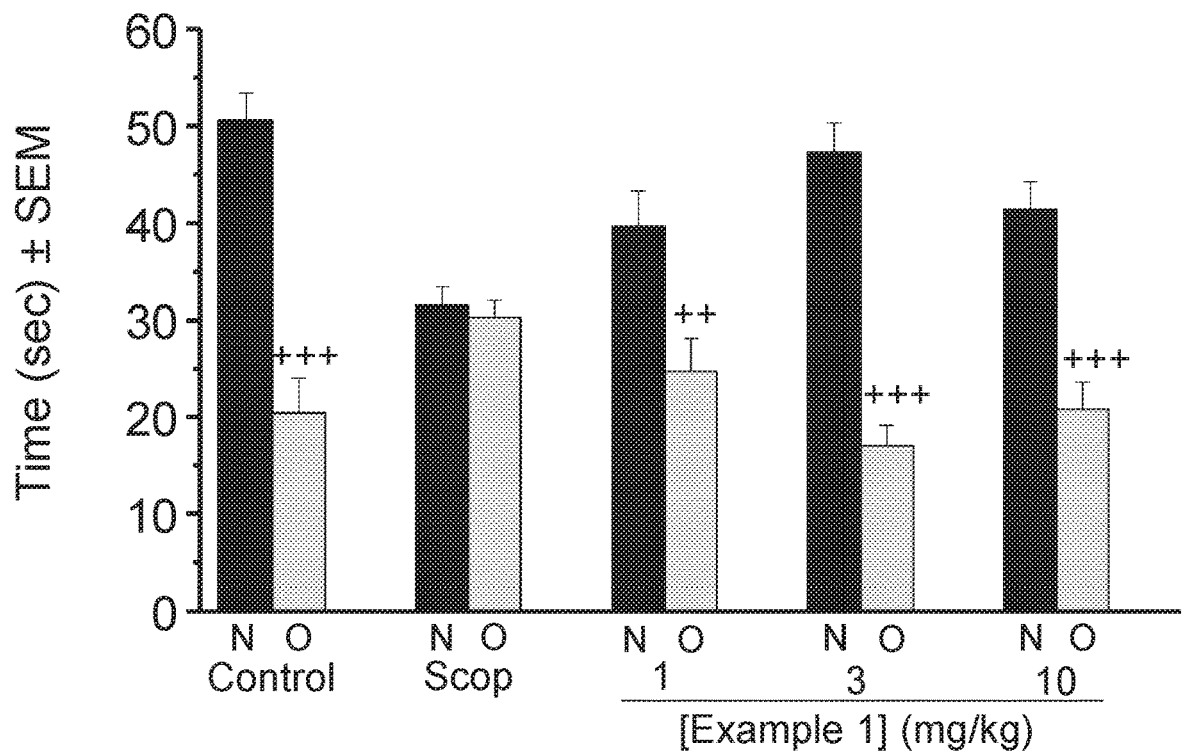
FIG. 1 illustrates the results of place recognition test of compound Example 1. Exploration times spent in the novel [N] vs. familiar [O] arms of the Y maze are depicted). Scop: scopolamine (1 mg/kg, ip.). $^+p<0.05$; $^{++}p<0.01$; $^{+++}p<0.001$.
Figure 2:
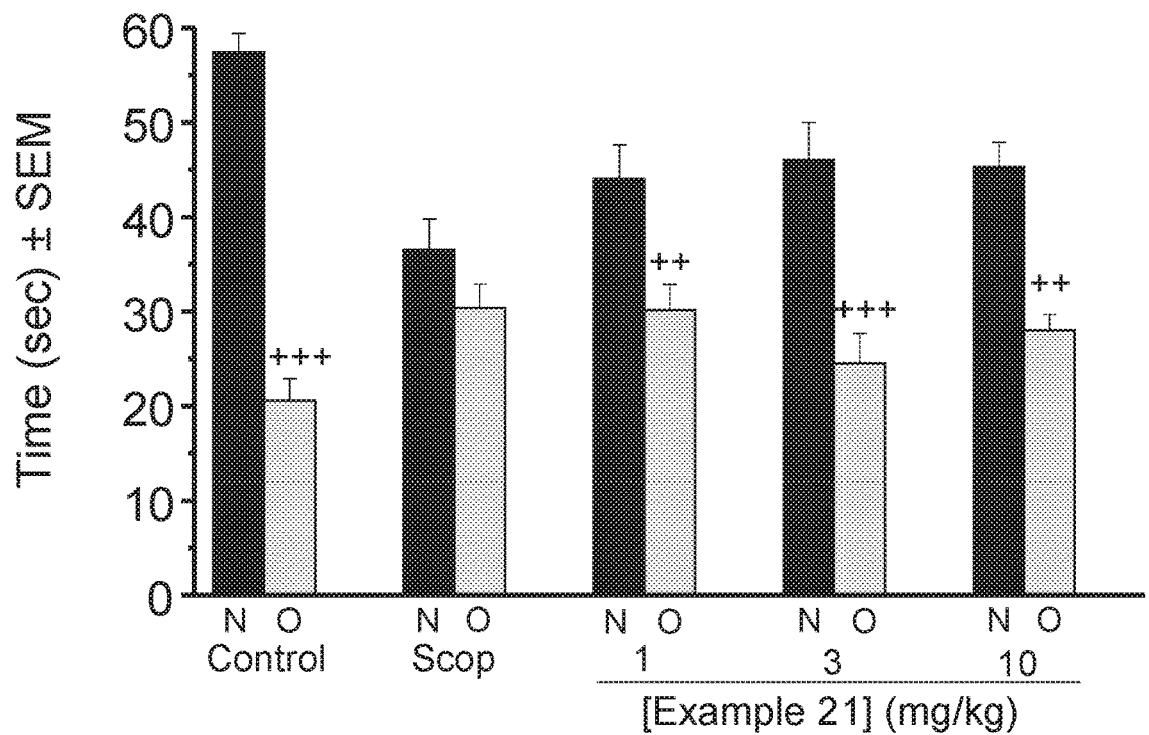
FIG. 2 illustrates the results of place recognition test of compound Example 21. Exploration times spent in the novel [N] vs. familiar [O] arms of the Y maze are depicted). Scop: scopolamine (1 mg/kg, ip.). $^+p<0.05$; $^{++}p<0.01$; $^{+++}p<0.001$.
Figure 3:
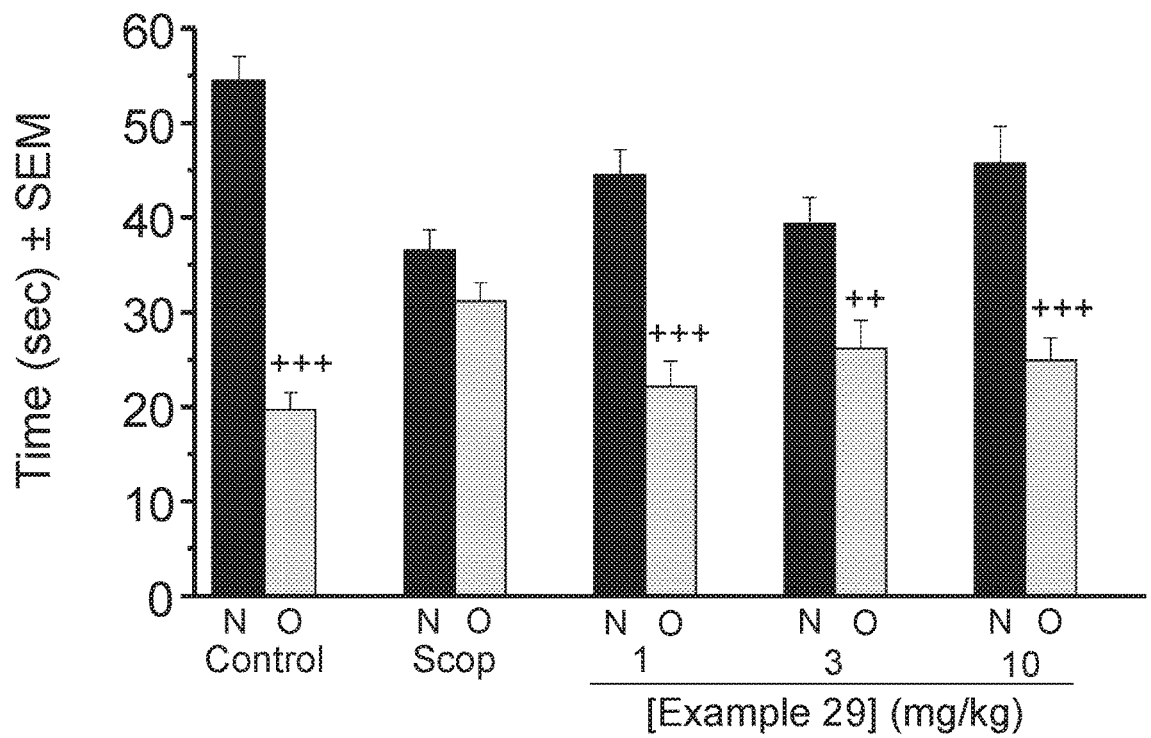
FIG. 3 illustrates the results of place recognition test of compound Example 29. Exploration times spent in the novel [N] vs. familiar [O] arms of the Y maze are depicted). Scop: scopolamine (1 mg/kg, ip.). $^+p<0.05$; $+^+p<0.01$; $^{+++}p<0.001$.
Figure 4:
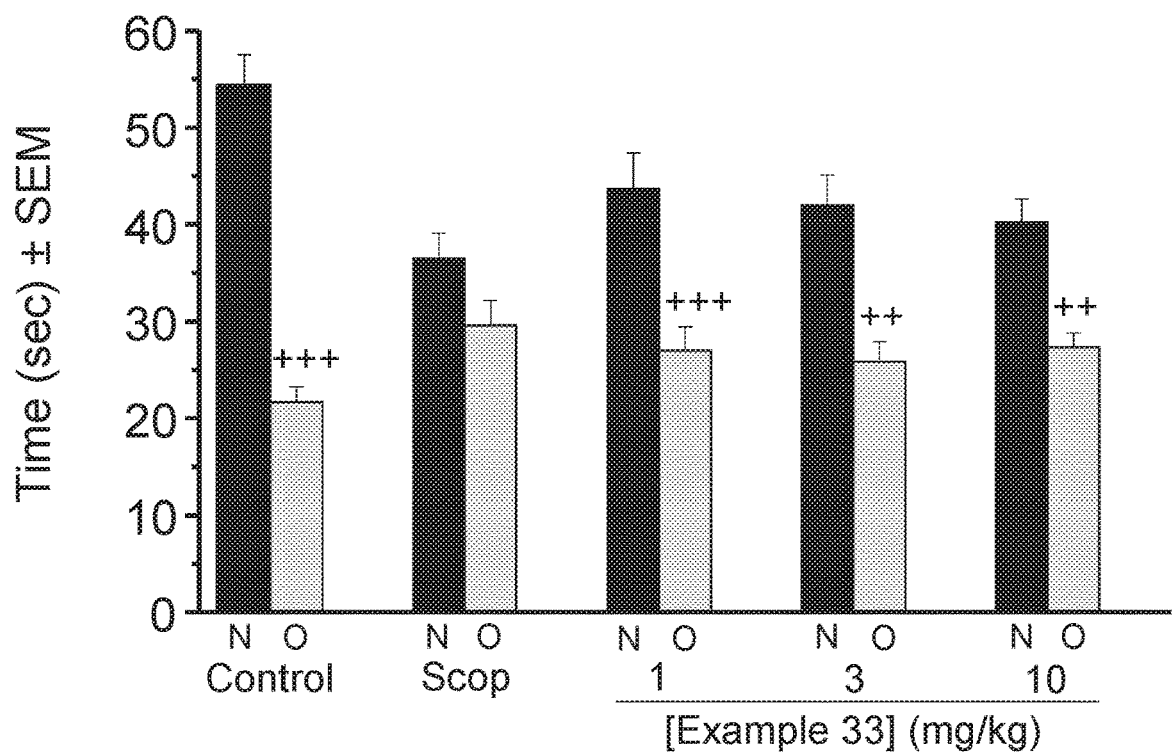
FIG. 4 illustrates the results of place recognition test of compound Example 33. Exploration times spent in the novel [N] vs. familiar [O] arms of the Y maze are depicted). Scop: scopolamine (1 mg/kg, ip.). $^+p<0.05$; $^{++}p<0.01$; $^{+++}p<0.001$.
Figure 5:
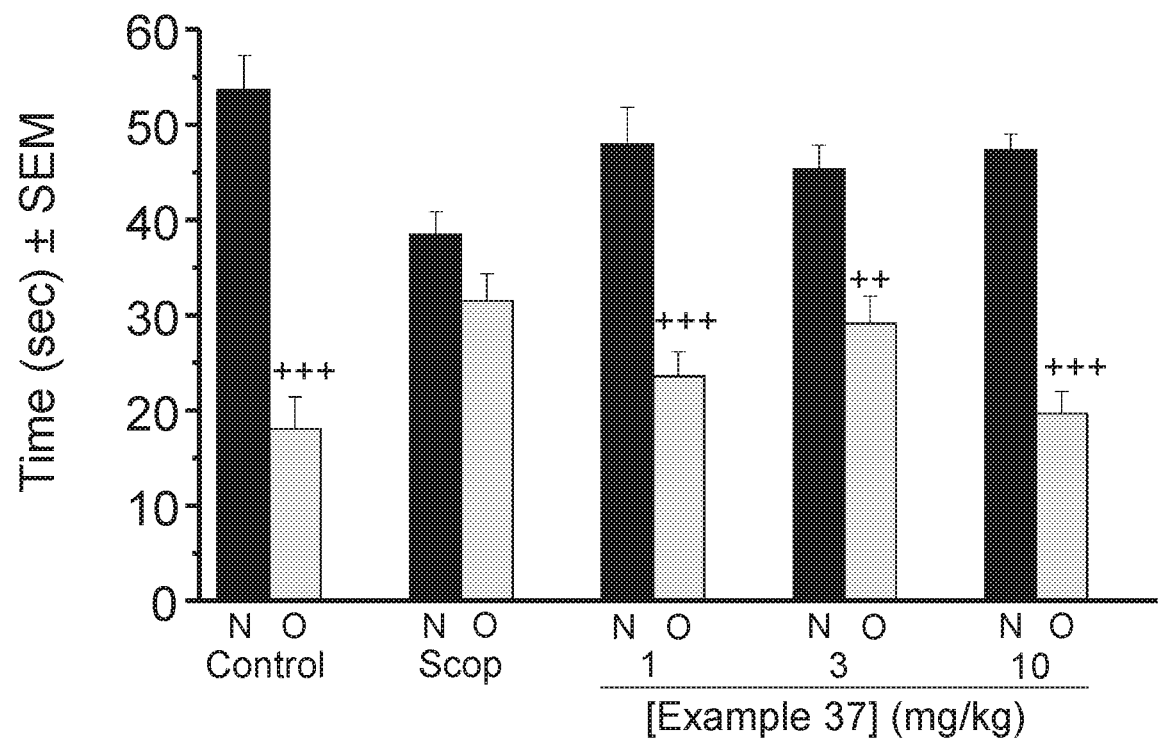
FIG. 5 illustrates the results of place recognition test of compound Example 37. Exploration times spent in the novel [N] vs. familiar [O] arms of the Y maze are depicted). Scop: scopolamine (1 mg/kg, ip.). $^+p<0.05$; $^{++}p<0.01$; $^{+++}p<0.001$.
Figure 6:
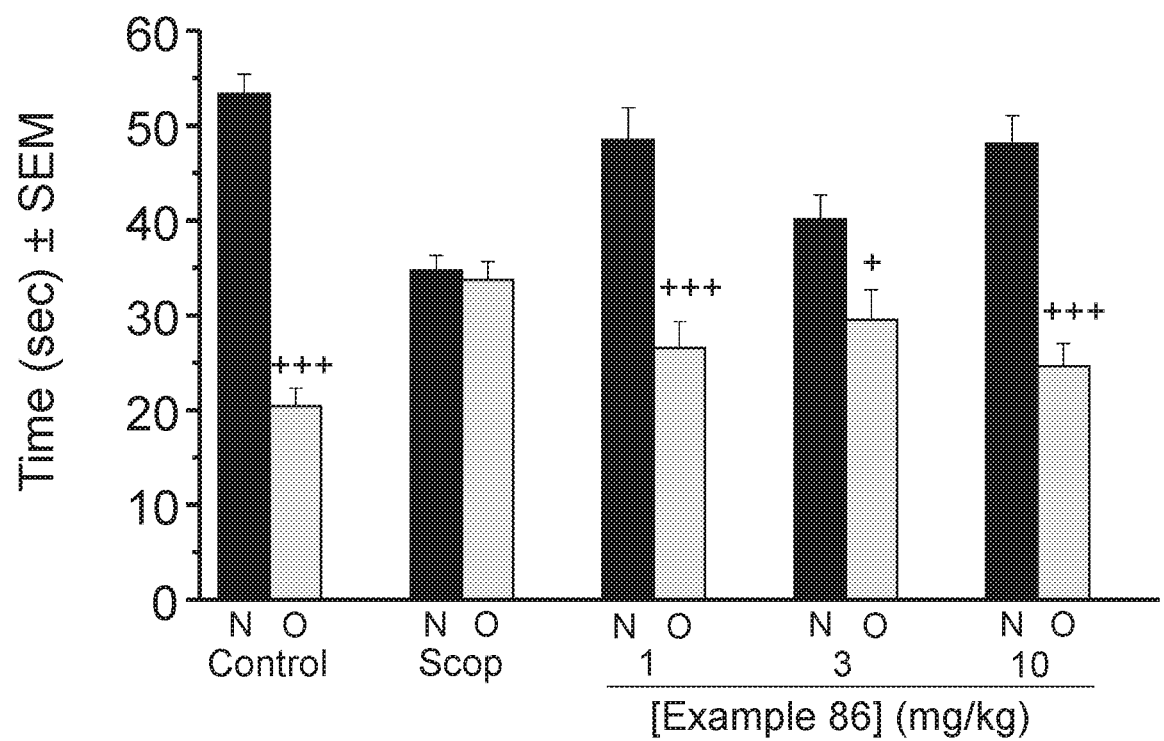
FIG. 6 illustrates the results of place recognition test of compound Example 86. Exploration times spent in the novel [N] vs. familiar [O] arms of the Y maze are depicted). Scop: scopolamine (1 mg/kg, ip.). $^+p<0.05$; $^{++}p<0.01$; $^{+++}p<0.001$.
Figure 7:
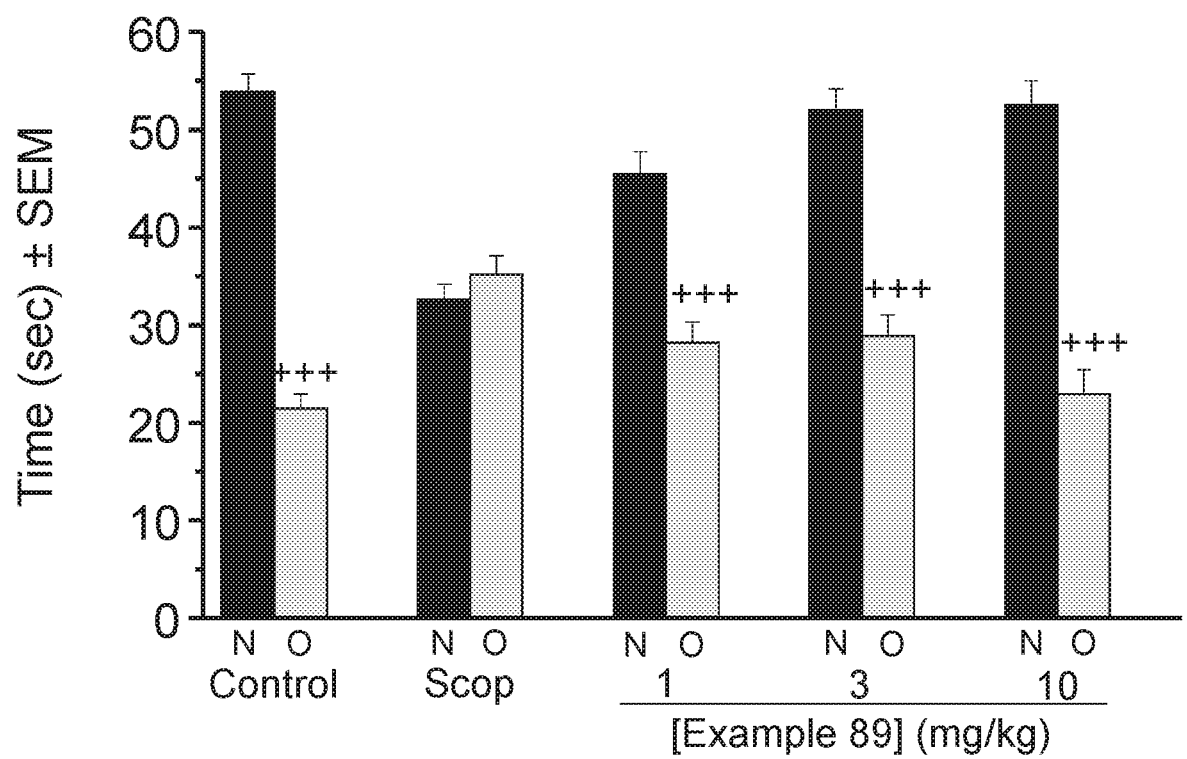
FIG. 7 illustrates the results of place recognition test of compound Example 89. Exploration times spent in the novel [N] vs. familiar [O] arms of the Y maze are depicted). Scop: scopolamine (1 mg/kg, ip.). $^+p<0.05$; $^{++}p<0.01$; $^{+++}p<0.001$.

The present invention relates to compounds of formula (I),

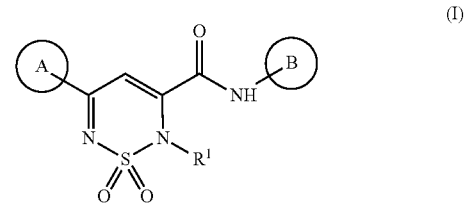

wherein
A is saturated, unsaturated or aromatic, monocyclic or bycyclic, fused or bridged carbocyclyl, or a saturated, unsaturated or aromatic monocyclic or bycyclic, fused or bridged heterocyclyl, optionally substituted by one or more halogen atom or halogen atoms, $C_{1-6}$alkyl, $C_{1-6}$alkoxy, or halo$C_{1-6}$alkyl;
B is saturated, unsaturated or aromatic, monocyclic or bycyclic, fused or bridged carbocyclyl, or a saturated, unsaturated or aromatic monocyclic or bycyclic, fused or bridged heterocyclyl, optionally substituted by one or more halogen atom or halogen atoms, $C_{1-6}$alkyl, $C_{1-6}$alkoxy, halo$C_{1-6}$alkyl, CN, C(O)$C_{1-6}$alkyl, or halo$C_{1-6}$alkoxy;

$R^1$ is $C_{1-6}$alkyl, $C_{1-6}$alkenyl, halo$C_{1-6}$alkyl, $C_{3-8}$cycloalkyl$C_{1-6}$alkyl, $C_{1-6}$alkoxy$C_{1-6}$alkyl, or $C_{4-6}$heterocyclyl;

or pharmaceutically acceptable salts, biologically active metabolites, pro-drugs, racemates, enantiomers, diastereomers, solvates and hydrates thereof.

In a further aspect, the present invention provides a compound of formula (I), as defined above for use in the treatment or prevention of a disease associated with α7 nicotinic acetylcholine receptor activity.

In a further aspect, the present invention provides the use of a compound of formula (I), as defined above, for the manufacture of a medicament for the treatment or prevention of a disease associated with α7 nicotinic acetylcholine receptor activity.

In a further aspect, the present invention provides a method for the treatment or prevention of a disease associated with α7 nicotinic acetylcholine receptor activity comprising administering to a mammal in need of such treatment or prevention an effective amount of at least one compound of formula (I), as defined above.

In a further aspect, the compounds of formula (I) as defined above, can be administered in combination with other compounds used for the treatment or prevention of a disease associated with α7 nicotinic acetylcholine receptor activity.

In a further aspect, the present invention provides a process for the manufacture of the compounds of formula (I).

DETAILED DESCRIPTION OF THE INVENTION

The present invention relates to compounds of formula (I),

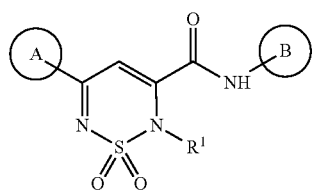

(I)

wherein

A is saturated, unsaturated or aromatic, monocyclic or bycyclic, fused or bridged carbocyclyl, or a saturated, unsaturated or aromatic monocyclic or bycyclic, fused or bridged heterocyclyl, optionally substituted by one or more halogen atom or halogen atoms, $C_{1-6}$alkyl, $C_{1-6}$alkoxy, or halo$C_{1-6}$alkyl;

B is saturated, unsaturated or aromatic, monocyclic or bycyclic, fused or bridged carbocyclyl, or a saturated, unsaturated or aromatic monocyclic or bycyclic, fused or bridged heterocyclyl, optionally substituted by one or more halogen atom or halogen atoms, $C_{1-6}$alkyl, $C_{1-6}$alkoxy, halo$C_{1-6}$alkyl, CN, C(O)$C_{1-6}$alkyl, or halo$C_{1-6}$alkoxy;

$R^1$ is $C_{1-6}$alkyl, $C_{1-6}$alkenyl, halo$C_{1-6}$alkyl, $C_{3-8}$cycloalkyl$C_{1-6}$alkyl, $C_{1-6}$alkoxy$C_{1-6}$alkyl, or $C_{4-6}$heterocyclyl;

or pharmaceutically acceptable salts, biologically active metabolites, pro-drugs, racemates, enantiomers, diastereomers, solvates and hydrates thereof.

The term "saturated, unsaturated or aromatic, monocyclic or bycyclic, fused or bridged carbocyclyl" refers alone or in combination with other groups to a monovalent monocyclic or bicyclic, fused or bridged, saturated, mono-, or bi-unsaturated, or aromatic ring system comprising 3 to 10 carbon ring atoms. Saturated carbocycles include monovalent monocyclic or bicyclic, fused or bridged, saturated carbocyclic groups comprising 3 to 10 carbon ring atoms. Examples include cyclopropyl, cyclobutyl, cyclopentyl, cyclopentenyl, cyclohexyl, cycloheptyl, cyclooctyl, bicyclo[3.1.0]hexanyl, bicyclo[2.2.1]heptanyl, bicyclo[2.2.2]octanyl or adamantanyl and the like. Unsaturated carbocycles include monovalent monocyclic or bicyclic, fused or bridged, mono-, or bi-unsaturated carbocyclic groups comprising 4 to 10 carbon ring atoms. Examples include cyclobutenyl, cyclopentenyl, cyclohexenyl, cyclohexadienyl, cycloheptenyl and the like. Aromatic carbocycles include monovalent, mono- or bicyclic aromatic carbocyclic groups comprising 6 to 10 carbon ring atoms. Examples include phenyl and naphthyl.

The term "saturated, unsaturated or aromatic monocyclic or bycyclic, fused or bridged heterocyclyl" refers alone or in combination with other groups to a monovalent monocyclic or bicyclic, fused or bridged, saturated, mono-, or bi-unsaturated, or aromatic ring system comprising 3 to 12 ring atoms, having at least one ring comprising one, two, or three or four ring heteroatoms, chosen from nitrogen, oxygen or sulphur, preferably nitrogen and oxygen. Saturated heterocycles include monovalent monocyclic or bicyclic, fused or bridged, saturated heterocyclic groups comprising 3 to 12 ring atoms, having at least one ring comprising one, two, or three or four ring heteroatoms, chosen from nitrogen, oxygen or sulphur, preferably nitrogen and oxygen. Examples include, azetidinyl, oxetanyl, pyrrolidinyl, pirazolidinyl, izoxasolidinyl, tetrahydrofuryl, piperidinyl, piperazinyl, tetrahydropyranyl, morpholinyl, thiomorpholinyl, decahydroquinolinyl, decahydroisoquinolinyl, azaadamantanyl. Unsaturated heterocycles include monovalent monocyclic or bicyclic, fused or bridged, mono-, or bi-unsaturated heterocyclic groups comprising 5 to 12 ring atoms, having at least one ring comprising one, two, or three or four ring heteroatoms, chosen from nitrogen, oxygen or sulphur, preferably nitrogen and oxygen. Examples include, pyrrolinyl, pyrazolinyl, benzoxazolyl, benzthiazolyl, indolyl, isoindolyl, azaindolyl, benzodioxolyl, pyrazolo[1,5-a]pyrimidinyl, pyrazolo[1,5-a]pyridinyl, 1,2,3,4-tetrahydro-isoquinolinyl. Aromatic heterocycles include monovalent, mono- or bicyclic aromatic heterocyclic groups comprising 5 to 12 ring atoms, having at least one ring comprising one, two, or three or four ring heteroatoms, chosen from nitrogen, oxygen or sulphur, preferably nitrogen and oxygen. Examples include, pyrrolyl, pyrazolyl, imidazolyl, furyl, thiophenyl, oxazolyl, isoxazolyl, thiazolyl, pyridyl, pyridazyl, pyrimidinyl, pyrazinyl, benzimidazolyl, quinolinyl, isoquinolinyl.

The term "halo" or "halogen", as used herein as such or as part of another group, refers to fluoro, chloro, bromo or iodo.

The term "$C_{1-6}$alkyl", as used herein as such or as part of another group, refers to a branched or straight chain saturated hydrocarbon group having one, two, three, four, five or six carbon atoms including, but not limited to, methyl, ethyl, n-propyl, i-propyl, i-butyl, sec-butyl, and tert-butyl.

The term "halo$C_{1-6}$alkyl", as used herein, refers to at least one halogen, as defined above, bonded to the parent molecular moiety through an "$C_{1-6}$alkyl" group, as defined above. When there are several halogens, the halogens can be identical or different and the halogens can be attached to different carbon atoms or several halogens can be attached to the same carbon atom. Halo$C_{1-6}$alkyl groups include, but are not limited to, difluoromethyl, trifluoromethyl, trifluoroethyl and 2-chloroethyl.

The term "$C_{1-6}$alkoxy", as used herein refers to an $C_{1-6}$alkyl group, as defined above, bonded to the parent molecular moiety through an oxygen atom including, but not limited to, methoxy, ethoxy, n-propoxy, i-propoxy and tert-butoxy.

The term "halo$C_{1-6}$alkoxy", as used herein refers to at least one halogen, as defined above, bonded to the parent molecular moiety through a "$C_{1-6}$alkoxy" group, as defined above. When there are several halogens, the halogens can be identical or different and the halogens can be attached to different carbon atoms or several halogens can be attached to the same carbon atom. Halo$C_{1-6}$alkoxy groups include, but are not limited to, trifluoromethoxyl, difluoromethoxyl, trifluoroethoxyl.

The term "$C_{1-6}$alkenyl", as used herein refers to linear or branched-chain monovalent hydrocarbon radical of two to six carbon atoms with at least one site of unsaturation, i.e., a carbon-carbon, sp double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "$C_{3-8}$cycloalkyl", as used herein as such or as part of another group, refers to cyclopropyl, cyclobutyl or cyclopentyl, cyclohexyl, cycloheptyl, cyclooctyl.

The term "$C_{3-8}$cycloalkyl$C_{1-6}$ alkyl", as used herein refers to refers to a $C_{3-8}$cycloalkyl group, as defined above, bonded to the parent molecular moiety through a "$C_{1-6}$alkyl" group, as defined above, including, but not limited to, cyclopropylmethyl and cyclobutylmethyl.

The term "$C_{1-6}$alkoxy$C_{1-6}$alkyl" as used herein refers to refers to a $C_{1-6}$alkoxy group, as defined above, bonded to the parent molecular moiety through a "$C_{1-6}$alkyl" group, as defined above, including, but not limited to, —$C_2H_5$—O—$CH_3$, —$CH_3$—O—$C_2H_5$, —$CH_3$—O—$CH_3$, —$C_2H_5$—O—$C_2H_5$, —$C_3H_7$—O—$CH_3$, —$CH_3$—O—$C_3H_7$, —$C_3H_7$—O—$C_2H_5$, —$C_2H_5$—O—$C_3H_7$.

The term "$C_{4-6}$heterocyclyl", as used herein refers to an optionally substituted moiety, consisting of 4-6 atoms forming one to two rings, incorporating one, two, or three or four heteroatoms, chosen from nitrogen, oxygen or sulfur. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, thiamorpholinyl.

The term "pharmaceutically acceptable" describes an ingredient that is useful in preparing a pharmaceutical composition, is generally safe, non-toxic and neither biologically nor otherwise undesirable, and includes those acceptable for veterinary use as well as human pharmaceutical use.

The term "hydrate" means non-covalent combinations between water and solute.

The term "solvate" means non-covalent combinations between solvent and solute. Solvents include, but are not limited to, ethanol, 2-propanol, acetonitrile and tetrahydrofuran.

"Optional" or "optionally" means that the subsequently described event or circumstance may but need not occur, and that the description includes instances where the event or circumstance occurs and instances in which it does not.

"Optionally substituted" means unsubstituted or substituted with one or more of the substituents as described herein. Here, "one or more" means from one to the highest possible number of substitution, that is, from replacing one hydrogen to replacing all hydrogens. One, two or three substituents on a given atom are preferred.

"Treating" or "treatment" of a disease state includes:
a) preventing the disease state, i.e. causing the clinical symptoms of the disease state not to develop in a subject that may be exposed to or predisposed to the disease state, but does not yet experience or display symptoms of the disease state,
b) inhibiting the disease state, i.e., arresting the development of the disease state or its clinical symptoms, or
c) relieving the disease state, i.e., causing temporary or permanent regression of the disease state or its clinical symptoms.

The term "pharmaceutically acceptable salt" refers to a conventional acid addition salt or a base addition salt, which preserves the biological efficacy and properties of the compounds of formula (I) and which can be formed with suitable non-toxic organic or inorganic acids or organic or inorganic bases. Examples of acid addition salts include salts derived from inorganic acids, such as, but not limited to, hydrochloric acid, hydrobromic acid, hydroiodic acid, sulfuric acid, sulphamic acid, phosphoric acid, nitric acid and perchloric acid and derived from various organic acids, such as, but not limited to, acetic acid, propionic acid, benzoic acid, glycolic acid, phenylacetic acid, salicylic acid, malonic acid, maleic acid, oleic acid, pamoic acid, palmitic acid, benzenesulfonic acid, toluenesulfonic acid, methanesulfonic acid, oxalic acid, tartaric acid, succinic acid, citric acid, malic acid, lactic acid, glutamic acid, fumaric acid and the like. Examples of base addition salts are salts derived from ammonium-, potassium-, sodium- and quaternary ammonium hydroxides such as tetramethylammonium hydroxide.

The term "pro-drug" refers to derivatives of compounds of formula (I) according to the invention which themselves have no therapeutic effect but containing such groups which, after in vivo chemical or metabolic degradation (biotransformation) become "biologically active metabolite" which is responsible for the therapeutic effect. Such decomposing groups associated with the compounds of formula (I) of the present invention, in particular those suitable for prodrugs, are known in the art and may also be applied for the compounds of the present invention (Rautio et al., Nature Reviews—Drug Discovery 2008, 7:255-270).

In one embodiment, the present invention relates to compounds of formula (I), wherein A is saturated, unsaturated or aromatic, monocyclic or bycyclic, fused or bridged carbocyclyl, or a saturated, unsaturated or aromatic monocyclic or bycyclic, fused or bridged heterocyclyl, containing 1-3 heteroatoms selected from the group nitrogen, oxygen and sulphur, optionally substituted by one or more halogen atom or halogen atoms, $C_{1-3}$alkyl, $C_{1-3}$alkoxy, or halo$C_{1-3}$alkyl;

B is saturated, unsaturated or aromatic, monocyclic or bycyclic, fused or bridged carbocyclyl, or a saturated, unsaturated or aromatic monocyclic or bycyclic, fused or bridged heterocyclyl, containing 1-3 heteroatoms selected from the group nitrogen, oxygen and sulphur, optionally substituted by one or more halogen atom or halogen atoms, $C_{1-3}$alkyl, $C_{1-3}$alkoxy, halo$C_{1-3}$alkyl, CN, C(O)$C_{1-3}$alkyl, or halo$C_{1-3}$alkoxy;

$R^1$ is $C_{1-4}$alkyl, $C_{1-3}$alkenyl, halo$C_{1-3}$alkyl, $C_{3-8}$cycloalkyl$C_{1-3}$ alkyl, $C_{1-3}$alkoxy$C_{1-3}$alkyl, or $C_{4-6}$heterocyclyl;

or pharmaceutically acceptable salts, biologically active metabolites, pro-drugs, racemates, enantiomers, diastereomers, solvates and hydrates thereof.

In one embodiment, the present invention relates to compounds of formula (I), wherein A is saturated, unsaturated or aromatic, 4-9 membered, monocyclic or bycyclic, fused or bridged carbocyclyl, or a saturated, unsaturated or aromatic 4-9 membered, monocyclic or bycyclic, fused or bridged heterocyclyl containing 1-3 heteroatoms selected from the group nitrogen and oxygen, optionally substituted by one or more halogen atom or halogen atoms, $C_{1-6}$alkyl, $C_{1-6}$alkoxy, or halo$C_{1-6}$alkyl;

B is saturated, unsaturated or aromatic, 4-9 membered, monocyclic or bycyclic, fused or bridged carbocyclyl, or a saturated, unsaturated or aromatic 4-9 membered, monocyclic or bycyclic, fused or bridged heterocyclyl containing 1-3 heteroatoms selected from the group nitrogen and oxygen, optionally substituted by one or more halogen atom or halogen atoms, $C_{1-6}$alkyl, $C_{1-6}$alkoxy, halo$C_{1-6}$alkyl, CN, C(O)$C_{1-6}$alkyl, or halo$C_{1-6}$alkoxy;

$R^1$ is $C_{1-6}$alkyl, $C_{1-6}$alkenyl, halo$C_{1-6}$alkyl, $C_{3-8}$cycloalkyl$C_{1-6}$alkyl, $C_{1-6}$alkoxy$C_{1-6}$alkyl, or $C_{4-6}$heterocyclyl;

or pharmaceutically acceptable salts, biologically active metabolites, pro-drugs, racemates, enantiomers, diastereomers, solvates and hydrates thereof.

In one embodiment, the present invention relates to compounds of formula (I), wherein A is saturated, unsaturated or aromatic, 4-9 membered, monocyclic or bycyclic, fused or bridged carbocyclyl, or a saturated, unsaturated or aromatic 4-9 membered, monocyclic or bycyclic, fused or bridged heterocyclyl containing 1-3 heteroatoms selected from the group of nitrogen, and oxygen optionally substituted by one or more halogen atom or halogen atoms, $C_{1-3}$alkyl, $C_{1-3}$alkoxy, or halo$C_{1-3}$alkyl;

B is saturated, unsaturated or aromatic, 4-9 membered, monocyclic or bycyclic, fused or bridged carbocyclyl, or a saturated, unsaturated or aromatic 4-9 membered, monocyclic or bycyclic, fused or bridged heterocyclyl containing 1-3 heteroatoms selected from the group nitrogen, and oxygen, optionally substituted by one or more halogen atom or halogen atoms, $C_{1-3}$alkyl, $C_{1-3}$alkoxy, halo$C_{1-3}$alkyl, CN, C(O)$C_{1-3}$alkyl, or halo$C_{1-3}$alkoxy;

$R^1$ is $C_{1-4}$alkyl, $C_{1-3}$alkenyl, halo$C_{1-3}$alkyl, $C_{3-8}$cycloalkyl$C_{1-3}$alkyl, $C_{1-3}$ alkoxy$C_{1-3}$alkyl, or $C_{4-6}$heterocyclyl;

or pharmaceutically acceptable salts, biologically active metabolites, pro-drugs, racemates, enantiomers, diastereomers, solvates and hydrates thereof.

In one embodiment, the present invention relates to compounds of formula (I),

A is a cyclopentenyl, cyclohexyl, phenyl, cycloheptyl, bicyclo[3.1.0]hexanyl or indazolyl, optionally substituted by one or more halogen atom or halogen atoms, $C_{1-3}$alkyl, $C_{1-3}$alkoxy, or halo$C_{1-3}$alkyl;

B is a phenyl, pyridyl, pyrazyl, pyrazinyl, pyrimidinyl, benzodioxolyl, 1,2,3,4-tetrahydro-isoquinolinyl, or pyrazolo[1,5-a]pyridinyl, optionally substituted by one or more halogen atom or halogen atoms, $C_{1-3}$alkyl, $C_{1-3}$alkoxy, halo$C_{1-3}$alkyl, CN, C(O)$C_{1-3}$alkyl, or halo$C_{1-3}$alkoxy;

$R^1$ is $CH_3$, $C_2H_5$, nPr, iPr, nBu, secBu, allyl, —$CH_2$—$CF_3$, —$CH_2$-cBu, —$CH_2$-cPr, —$C_2H_5$—O—$CH_3$, or tetrahydrofuryl;

or pharmaceutically acceptable salts, biologically active metabolites, pro-drugs, racemates, enantiomers, diastereomers, solvates and hydrates thereof.

In one embodiment, the present invention relates to compounds of formula (I) selected from the group of:

5-(3,4-dimethoxyphenyl)-2-methyl-N-(3-methylphenyl)-1,1-dioxo-2H-1$\lambda^6$,2,6-thiadiazine-3-carboxamide;

5-(1,3-dimethyl-1H-indazol-5-yl)-2-methyl-N-(3-methylphenyl)-1,1-dioxo-2H-1$\lambda^6$,2,6-thiadiazine-3-carboxamide;

5-(3,4-dimethoxyphenyl)-2-ethyl-N-(3-methylphenyl)-1,1-dioxo-2H-1$\lambda^6$,2,6-thiadiazine-3-carboxamide;

5-(3,4-dimethoxyphenyl)-2-ethyl-1,1-dioxo-N-[6-(trifluoromethyl)pyridin-2-yl]-2H-1$\lambda^6$,2,6-thiadiazine-3-carboxamide;

2-ethyl-5-[4-methoxy-3-(trifluoromethyl)phenyl]-N-(3-methoxyphenyl)-1,1-dioxo-2H-1$\lambda^6$,2,6-thiadiazine-3-carboxamide;

2-ethyl-5-[4-methoxy-3-(trifluoromethyl)phenyl]-N-(4-methoxyphenyl)-1,1-dioxo-2H-1$\lambda^6$,2,6-thiadiazine-3-carboxamide;

2-ethyl-1,1-dioxo-5-[(1r,4r)-4-(trifluoromethyl)cyclohexyl]-N-[6-(trifluoromethyl)pyridin-2-yl]-2H-1$\lambda^6$,2,6-thiadiazine-3-carboxamide;

N-(6-cyanopyridin-2-yl)-2-ethyl-1,1-dioxo-5-[(1r,4r)-4-(trifluoromethyl)cyclohexyl]-2H-1$\lambda^6$,2,6-thiadiazine-3-carboxamide;

5-(3,4-dimethoxyphenyl)-1,1-dioxo-2-(propan-2-yl)-N-[6-(trifluoromethyl)pyridin-2-yl]-2H-1$\lambda^6$,2,6-thiadiazine-3-carboxamide;

5-(3,4-dimethoxyphenyl)-1,1-dioxo-2-propyl-N-[3-(trifluoromethyl)phenyl]-2H-1$\lambda^6$,2,6-thiadiazine-3-carboxamide;

5-(3,4-dimethoxyphenyl)-1,1-dioxo-2-propyl-N-[6-(trifluoromethyl)pyridin-2-yl]-2H-1$\lambda^6$,2,6-thiadiazine-3-carboxamide;

5-[4-methoxy-3-(trifluoromethyl)phenyl]-1,1-dioxo-2-propyl-N-[6-(trifluoromethyl)pyridin-2-yl]-2H-1$\lambda^6$,2,6-thiadiazine-3-carboxamide:

5-(4-methoxy-3-methylphenyl)-1,1-dioxo-2-propyl-N-[6-(trifluoromethyl)pyridin-2-yl]-2H-1$\lambda^6$,2,6-thiadiazine-3-carboxamide;

5-(3-chloro-4-methoxyphenyl)-1,1-dioxo-2-propyl-N-[6-(trifluoromethyl)pyridin-2-yl]-2H-1$\lambda^6$,2,6-thiadiazine-3-carboxamide;

2-(cyclopropylmethyl)-1,1-dioxo-5-[(1r,4r)-4-(trifluoromethyl)cyclohexyl]-N-[6-(trifluoromethyl)pyridin-2-yl]-2H-1$\lambda^6$,2,6-thiadiazine-3-carboxamide;

5-(3,4-dimethoxyphenyl)-1,1-dioxo-2-(prop-2-en-1-yl)-N-[6-(trifluoromethyl)pyridin-2-yl]-2H-1$\lambda^6$,2,6-thiadiazine-3-carboxamide;

5-(3,4-dimethoxyphenyl)-N-(4-methoxyphenyl)-1,1-dioxo-2-propyl-2H-1$\lambda^6$,2,6-thiadiazine-3-carboxamide:

5-(3,4-dimethoxyphenyl)-N-(3-methylphenyl)-1,1-dioxo-2-propyl-2H-1$\lambda^6$,2,6-thiadiazine-3-carboxamide;

5-[4-methoxy-3-(trifluoromethyl)phenyl]-1,1-dioxo-2-propyl-N-[3-(trifluoromethyl)phenyl]-1$\lambda^6$,2,6-thiadiazine-3-carboxamide;

5-(3,4-dimethoxyphenyl)-N-(6-fluoropyridin-2-yl)-1,1-dioxo-2-(propan-2-yl)-2H-1$\lambda^6$,2,6-thiadiazine-3-carboxamide;

N-(6-fluoropyridin-2-yl)-1,1-dioxo-2-(propan-2-yl)-5-[(1r,4r)-4-(trifluoromethyl)cyclohexyl]-2H-1$\lambda^6$,2,6-thiadiazine-3-carboxamide;

2-(cyclopropylmethyl)-N-(6-fluoropyrazin-2-yl)-1,1-dioxo-5-[(1r,4r)-4-(trifluoromethyl)cyclohexyl]-1$\lambda^6$,2,6-thiadiazine-3-carboxamide;

2-[(2R)-butan-2-yl]-5-(3,4-dimethoxyphenyl)-1,1-dioxo-N-[6-(trifluoromethyl)pyridin-2-yl]-1$\lambda^6$,2,6-thiadiazine-3-carboxamide;

2-ethyl-5-[4-methoxy-3-(trifluoromethyl)phenyl]-1,1-dioxo-N-[6-(trifluoromethyl)pyridin-2-yl]-2H-1$\lambda^6$,2,6-thiadiazine-3-carboxamide;

1,1-dioxo-2-(propan-2-yl)-5-[(1r,4r)-4-(trifluoromethyl)cyclohexyl]-N-[6-(trifluoromethyl)pyrazin-2-yl]-2H-1$\lambda^6$,2,6-thiadiazine-3-carboxamide;

2-(cyclopropylmethyl)-5-(4,4-difluorocyclohexyl)-1,1-dioxo-N-[6-(trifluoromethyl)pyridin-2-yl]-2H-1$\lambda^6$,2,6-thiadiazine-3-carboxamide:

2-(cyclopropylmethyl)-1,1-dioxo-5-[(1r,4r)-4-(trifluoromethyl)cyclohexyl]-N-[2-(trifluoromethyl)pyrimidin-4-yl]-2H-1$\lambda^6$,2,6-thiadiazine-3-carboxamide;

or pharmaceutically acceptable salts, biologically active metabolites, pro-drugs, racemates, enantiomers, diastereomers, solvates and hydrates thereof.

In a further aspect, the present invention provides a compound of formula (I), as defined above for use in the treatment or prevention of a disease associated with α7 nicotinic acetylcholine receptor activity.

In a further aspect, the present invention provides the use of a compound of formula (I), as defined above, for the manufacture of a medicament for the treatment or prevention of a disease associated with α7 nicotinic acetylcholine receptor activity.

In a further aspect, the present invention provides a method for the treatment or prevention of a disease associated with α7 nicotinic acetylcholine receptor activity comprising administering to a mammal in need of such treatment or prevention an effective amount of at least one compound of formula (I), as defined above.

In one embodiment, the disease associated with α7 nicotinic acetylcholine receptor activity is selected from the group of psychotic disorders, including, but not limited to, schizophrenia, schizophreniform disorder, schizoaffective disorder, delusional disorder, brief psychotic disorder, psychotic disorder due to a general medical condition, substance-induced psychotic disorder or psychotic disorder not otherwise specified; cognitive impairment, including, but not limited to, cognitive impairment as a result of stroke, Alzheimer's disease, Huntington's disease, Pick disease, HIV associated dementia, frontotemporal dementia, Lewy body dementia, vascular dementia, cerebrovascular disease or other dementia states and dementia associated to other degenerative disorders, including, but not limited to, amyotrophic lateral sclerosis, other acute or sub-acute conditions that may cause cognitive decline, including, but not limited to, delirium, traumatic brain injury, senile dementia, mild cognitive impairment, Down's syndrome, depression and cognitive deficit related to other diseases, and dyskinetic disorders including, but not limited to, Parkinson's disease, neuroleptic-induced parkinsonism, or tardive dyskinesias, depression and mood disorders, including, but not limited to, depressive disorders and episodes, bipolar disorders, cyclothymic disorder, and bipolar disorder not otherwise specified, other mood disorders, substance-induced mood disorder and mood disorder not otherwise specified; anxiety disorders, panic disorder and panic attacks, obsessive compulsive disorder, posttraumatic stress disorder, acute stress disorder, generalized anxiety disorder, anxiety disorder due to a general medical condition, substance-induced anxiety disorder, phobias, and anxiety disorder not otherwise specified; substance related disorders, including, but not limited to, substance use or substance-induced disorders, including, but not limited to, alcohol-, nicotine-, amphetamine-, phencyclidine-, opioid-, cannabis-, cocaine-, caffeine-, hallucinogen-, inhalant-, sedative-, hypnotic-, anxiolytic-, polysubstance- or other substance-related disorders; sleep disorders, including, but not limited to, narcolepsy, dyssomnias, primary hypersomnia, breathing-related sleep disorders, circadian rhythm sleep disorder and dyssomnia not otherwise specified; parasomnias, sleep terror disorder, sleepwalking disorder and parasomnia not otherwise specified; sleep disorders related to another mental disorder; sleep disorder due to a general medical condition and substance-induced sleep disorder; metabolic and eating disorders, including, but not limited to, anorexia nervosa, bulimia nervosa, obesity, compulsive eating disorder, binge eating disorder and eating disorder not otherwise specified; diabetes mellitus, ulcerative colitis, Crohn's disease, irritable bowel syndrome; autism spectrum disorders, including, but not limited to, autistic disorder, Asperger's disorder, Rett's disorder, childhood disintegrative disorder and pervasive developmental disorder not otherwise specified; attention deficit hyperactivity disorder, disruptive behaviour disorders, oppositional defiant disorder and disruptive behaviour disorder not otherwise specified; and tic disorders, including, but not limited to, Tourette's disorder; personality disorders; sexual dysfunctions such as sexual desire disorders, sexual arousal disorders, orgasmic disorders, sexual pain disorder, sexual dysfunction not otherwise specified, paraphilias, gender identity disorders, infertility, premenstrual syndrome and sexual disorders not otherwise specified; disorders of the respiratory system like cough, asthma, chronic obstructive pulmonary disease, lung inflammation, disorders of the cardiovascular system such as cardiac failure, heart arrhythmia, hypertension; inflammation, inflammatory and neuropathic pain, rheumatoid arthritis, osteoarthritis, allergy, sarcoidosis, psoriasis, ataxia, dystonia, systemic lupus erythematosus, mania, restless legs syndrome, progressive supranuclear palsy, epilepsy, myoclonus, migraine, amnesia, chronic fatigue syndrome, cataplexy, brain ischemia, multiple sclerosis, encephalomyelitis, jetlag, cerebral amyloid angiopathy, and sepsis.

In one embodiment, the disease associated with α7 nicotinic acetylcholine receptor activity is selected from the group of cognitive impairment, schizophrenia and autism.

The invention, further relates to combination therapies wherein a compound of the invention or a pharmaceutical composition or formulation comprising a compound of the invention is administered with another therapeutic agent or agents, for the treatment of one or more of the conditions previously indicated. Such therapeutic agents may be selected from: acetylcholinesterase inhibitors, NMDA receptor agonists or antagonists, anti-amyloid antibodies including anti-amyloid humanized monoclonal antibodies, beta- or gamma-secretase inhibitors or modulators, tau phosphorylation inhibitors, ApoE4 conformation modulators, p25/CDK5 inhibitors, NK1/NK3 receptor antagonists, COX-2 inhibitors, LRRK2 inhibitors, HMG-CoA reductase inhibitors, NSAIDs, vitamin E, glycine transport inhibitors, glycine site antagonists, LXR R agonists, androgen receptor modulators, blockers of Aβ oligomer formation, NR2B antagonists, anti-inflammatory compounds, PPAR gamma agonists, CB-1 receptor antagonists or inverse agonists, CB-2 agonists, VR-1 antagonists, bradykinin B1 receptor antagonists, sodium channel blockers and antagonists, NOS inhibitors, antibiotics, growth hormone secretagogues, potassium channel openers, AMPA agonists or AMPA modulators, GSK3 inhibitors, neuronal nicotinic agonists, MARK ligands, $M_1$ or $M_4$ mAChR agonists or PAMs, mGluR2 antagonists or NAMs or PAMs, mGluR5 antagonists, alpha-adrenerg agonists, ADAM-10 ligands, sedatives, hypnotics, anxiolytics, antipsychotics, cyclopyrrolones, imidazopyridines, pyrazolopyrimidines, minor tranquilizers, melatonin agonists and antagonists, melatonergic agents, orexin antagonists and agonists, prokineticin agonists and antagonists, T-type calcium channel antagonists, triazolopyridines benzodiazepines, barbiturates, $5\text{-HT}_{1A}$ antagonists, $5\text{-HT}_2$ antagonists, $5\text{-HT}_4$ agonists, $5\text{-HT}_6$ receptor antagonists, histamine H3 receptor antagonists and inverse agonists, $PDE_4$ inhibitors, $PDE_9$ inhibitors, $PDE_{10}$ inhibitors, HDAC inhibitors, KCNQ antagonists, $GABA_A$ inverse agonists, GABA signalling enhancers, GABA agonists, $GABA_A$ receptor alpha5 subunit NAMs or PAMs, antipsychotics, MAO-B inhibitors, dopamine transport inhibitors, noradrenaline transport inhibitors, $D_2$ agonists and partial agonists, anticholinergics, COMT inhibitors, A2a adenosine receptor antagonists, cholinergic agonists, neuroleptic agents, loxapine, sulpiride and risperidone, levodopa, calcium channel blockers, MMP inhibitors, thrombolytic agents, opioid analgesics, pramipexole, ropinirole, neutrophil inhibitory factor, SSRIs or SSNRIs, tricyclic antidepressant drugs, norepinephrine modulators, lithium, valproate, gabapentin, pregabalin, rizatriptan, zolmitriptan, naratriptan, and sumatriptan.

In one embodiment, the therapeutic agents are selected from the group of: acetylcholinesterase inhibitors, NMDA receptor antagonists, beta-secretase inhibitors, antipsychotics, $GABA_A$ receptor alpha5 subunit NAMs or PAMs, histamine $H_3$ receptor antagonists, $5\text{-HT}_6$ receptor antagonists, M1 or M4 mAChR agonists or PAMs, mGluR2 antagonists or NAMs or PAMs, and levodopa.

In a further aspect the present invention provides a process for the manufacture of the compounds of formula (I) according to the following reaction route:

Throughout the specification, general formulae are designated by Roman numerals (I), (II), (III) etc.

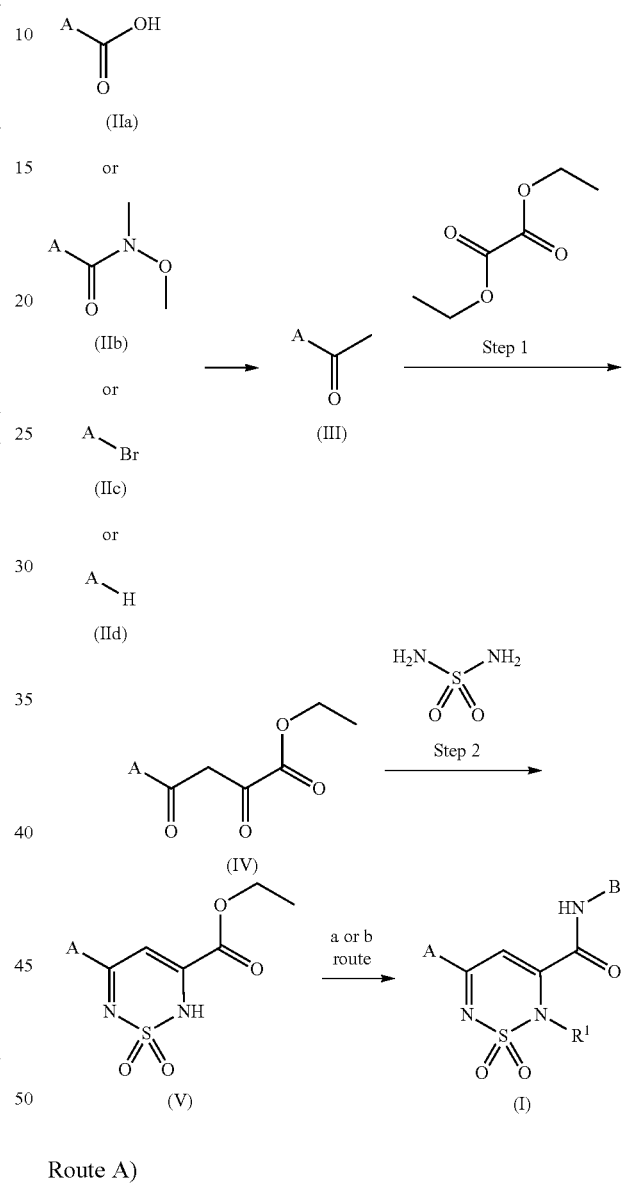

Route A)

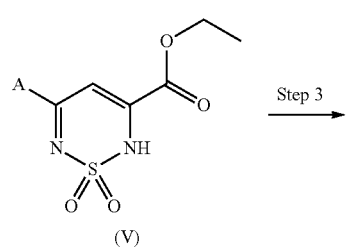

-continued
Step 6

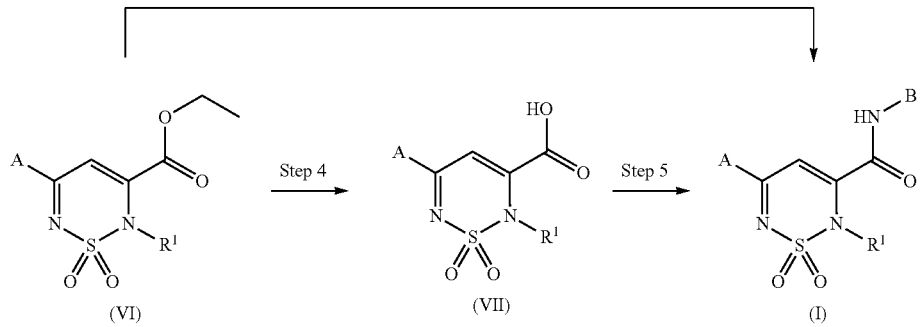

Route B)

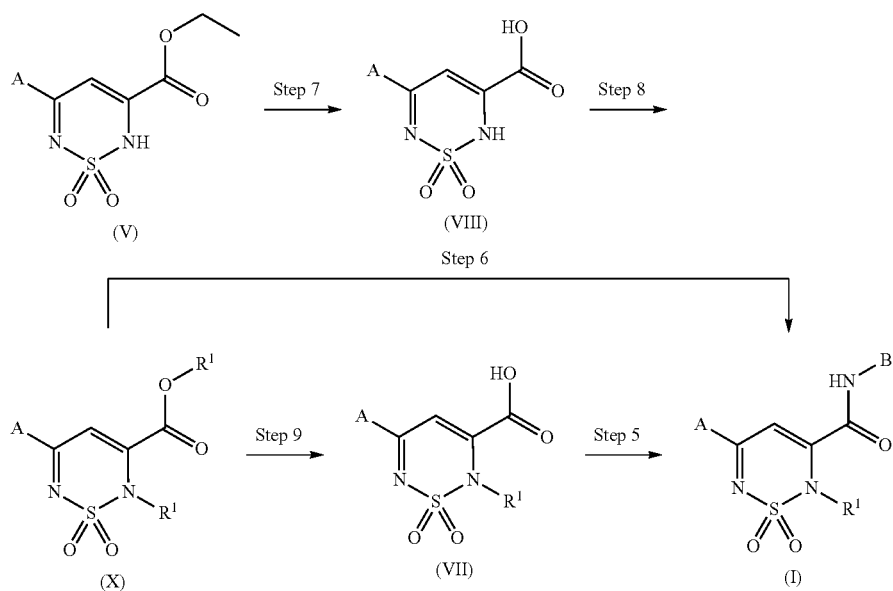

Reacting a carboxylic acid of formula (IIa) or a carboxylic acid derivative of formula (IIb)—wherein the meaning of A is described above for compound of formula (I)—with methyl lithium, or reacting compound of formula (IIc)—wherein the meaning of A is an aromatic, monocyclic or bycyclic, fused or bridged carbocyclyl or a saturated, unsaturated or aromatic, monocyclic or bycyclic, fused or bridged heterocyclyl, optionally substituted by one or more of $C_{1-6}$alkyl, $C_{1-6}$alkoxy, or halo$C_{1-6}$alkyl—with tributyl(1-ethoxyvinyl)tin, or reacting compound of formula (IId) with acetyl chloride—wherein the meaning of A is an aromatic, monocyclic or bycyclic, fused or bridged carbocyclyl or a saturated, unsaturated or aromatic, monocyclic or bycyclic, fused or bridged heterocyclyl, optionally substituted by one or more of $C_{1-6}$alkyl, $C_{1-6}$alkoxy, halo$C_{1-6}$alkyl, or halogen—ketone derivative of formula (III) was obtained

(III)

—wherein the meaning of A is as described above for formula (I)—and compound of formula (III) is reacted with diethyl oxalate to provide 2,4-dioxo ester derivative of formula (IV)

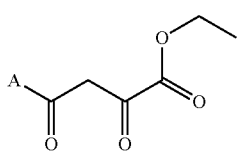

(IV)

—wherein the meaning of A is as described above for formula (I)—which is reacted with sulfamide, then the obtained 1,1-dioxo-1,3-thiadiazine carboxylic acid ester derivative of formula (V)

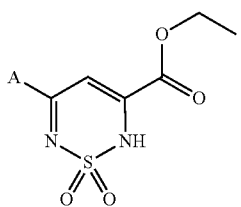
(V)

—wherein the meaning of A is as described above for formula (I)—can be transformed to the desired end product of the formula (I) in different ways:

ROUTE A) compound of formula (V) is alkylated to furnish N-alkyl thiadiazine derivative of formula (VI)

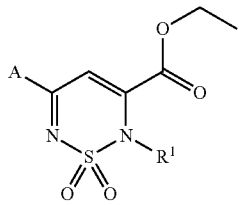
(VI)

—wherein the meaning of A and $R^1$ is as described above for formula (I)—which is hydrolysed leading to carboxylic acid derivative of formula (VII)

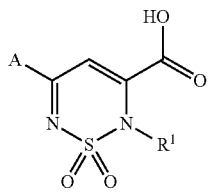
(VII)

—wherein the meaning of A and $R^1$ is as described above for formula (I)—which is coupled with an appropriate amine (B—$NH_2$)—wherein the meaning of B is as described above for formula (I)—to provide the desired amide of formula (I); or ROUTE B) the ester derivative of formula (V) is hydrolysed to furnish the carboxylic acid derivative of formula (VIII)

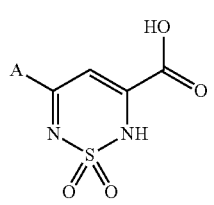
(VIII)

—wherein the meaning of A is as described above for formula (I)—which is then N,O-dialkylated in one step resulting the corresponding ester compound of formula (X)

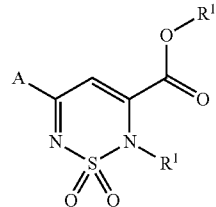
(X)

—wherein the meaning of A and $R^1$ is as described above for formula (I)—which is then either hydrolysed to derivative of formula (VII)

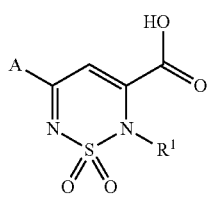
(VII)

—wherein the meaning of A and $R^1$ is as described above for formula (I)—and then reacted with the appropriate amine (B—$NH_2$) resulting in the targeted amide derivative of formula (I), or compound of formula (X) is transformed directly to the amide derivative of the formula (I) by reaction with the appropriate amine (B—$NH_2$).

The ketone derivative of formula (III) can be purchased or synthesized in the following ways:

i. The reaction of a carboxylic acid derivative of formula (IIa) with methyl lithium is preferably carried out in a suitable solvent, e.g., diethyl ether. The reaction is preferably carried out at −15° C. The necessary reaction time is 2-4 hours. The reactions are followed by thin layer chromatography. The reaction mixture is preferably quenched by addition of saturated ammonium chloride solution. The product is isolated by extraction with a suitable organic solvent, e.g., diethyl ether.

ii. The reaction of Weinreb amide of formula (IIb) with methyl lithium is preferably carried out in a suitable solvent, e.g., diethyl ether. The reaction is preferably carried out at −78° C. The necessary reaction time is 2-4 hours. The reactions are followed by thin layer chromatography. The reaction mixture is preferably quenched by addition of aqueous hydrogen chloride solution. The product is isolated by extraction with a suitable organic solvent, e.g., diethyl ether.

iii. The reaction of the corresponding halogenide of formula (IIc) with tributyl(1-ethoxyvinyl)tin in the presence of a suitable palladium catalyst, e.g., tetrakis (triphenylphosphine)palladium(0) and a base, preferably tripotassium phosphate in a suitable solvent, e.g., toluene or N-methyl-2-pyrrolidone. The reaction is preferably carried out at 80-90° C. The necessary reaction time is 6-7 hours. The reactions are followed by thin layer chromatography. The reaction mixture is diluted with water and extracted with an appropriate organic solvent, e.g., ethyl acetate. The organic phase is treated with 1 M hydrochloric acid solution at room temperature by vigorously stirring for 30 minutes. The pH of the mixture is adjusted to 7-8 by the addition of 25% aqueous ammonia solution and extracted with a suitable organic solvent, e.g., ethyl acetate and purified by column chromatography.

iv. The Friedel-Crafts reaction of the corresponding aromatic compound of formula (IId) with acetyl chloride in the presence of a suitable base, preferably aluminium chloride in a suitable solvent, preferably dichloromethane is carried out at 40° C. The necessary reaction time is 2 hours. The reaction mixture is poured onto 3 M HCl solution and extracted with diethyl ether. The combined organic layer is washed with saturated $NaHCO_3$ solution and brine, dried and evaporated to dryness.

The synthesis of compounds of formula (I) is described in more detail below:

Step 1

The Claisen condensation reaction of the acetyl derivative of formula (III) with diethyl oxalate to dioxoester derivative of formula (IV) is preferably carried out in the presence of a strong base, preferably sodium ethylate in a suitable solvent, e.g., ethanol. The reaction is preferably carried out at room temperature. The necessary reaction time is 6-15 hours. The reaction is followed by thin layer chromatography. The reaction mixture is quenched by pouring onto diluted aqueous hydrochloric acid solution (pH=1-3), and the product is isolated by filtration or by extraction with a suitable organic solvent, e.g., ethyl acetate.

Step 2

Cyclisation of the dioxoester of formula (IV) with sulfamide providing 1,1-dioxo-1,3-thiadiazine carboxylic acid ester derivative of formula (V) is performed in the presence of anhydrous ethanol saturated with hydrochloric acid in ethanol, as the solvent. The reaction is preferably carried out at 60-80° C. The necessary reaction time is 2-15 hours. The reactions are followed by thin layer chromatography. The product is isolated either by filtration, or by extraction.

The 1,1-dioxo-1,3-thiadiazine carboxylic acid ester derivative of formula (V) can be transformed to the desired end product of formula (I) in different ways:

Route A)

N-alkylation of 1,1-dioxo-1,3-thiadiazine carboxylic acid ester derivative of formula (V) is executed in different methods:

Step 3

Thiadiazine derivative of formula (V) is reacted with a suitable alkyl halogenide in a suitable solvent, preferably acetone, acetonitrile or N,N-dimethylformamide in the presence of a suitable amine, e.g., triethyl amine, diisopropyl ethylamine at 65-80° C. The necessary reaction time is 2-24 hours. The reaction mixture is diluted with water and acidified with aqueous hydrochloric acid solution. The product is isolated by extraction with a suitable organic solvent, preferably ethyl acetate and the isomers of product are separated by column chromatography. The structures of the products are determined by NMR spectroscopy and mass spectrometry.

Thiadiazine derivative of formula (V) is reacted with a secondary alcohol in the presence of triphenyl phosphine and diisopropyl azodicarboxylate in a suitable solvent, preferably tetrahydrofuran at 25-67° C. The necessary reaction time is 20-72 hours. The solvent is evaporated in vacuo and the product is isolated by column chromatography.

Step 4

Hydrolysis of N-alkylated ester of formula (VI) is carried out with base, e.g., 1-5 M NaOH or LiOH solution in a suitable solvent, e.g., tetrahydrofuran, or preferably ethanol at room temperature. The necessary reaction time is 1-3 hours. The reaction mixture is neutralised with aqueous hydrochloric acid solution. The organic solvent is evaporated in vacuo, the aqueous residue is acidified to pH=1-2, and the product is isolated by filtration or extraction with a suitable organic solvent, preferably ethyl acetate.

Step 5

The carboxylic acid of formula (VII) is coupled with the corresponding amine using a suitable coupling agent, such as HATU (1-[bis(dimethylamino)methylene]-1H-1,2,3-triazolo[4,5-b]pyridinium 3-oxide hexafluorophosphate) or EDC (1-ethyl-3-(3-dimethylaminopropyl)carbodiimide) in the presence of a suitable base, e.g., triethylamine, diisopropylethylamine, in a suitable solvent, preferably N,N-dimethylformamide. The reaction is preferably carried out at room temperature. The necessary reaction time is 6-48 hours. The reaction mixture is worked up either by evaporation of the solvent, or poured onto aqueous hydrochloric acid solution and extracted with a suitable organic solvent, preferably ethyl acetate. The product is isolated by column chromatography. The structures of the products are determined by NMR and mass spectrometry.

The amidation of carboxylic acid of formula (VII) can be performed via the corresponding carboxylic acid chloride as follows:

Carboxylic acid of formula (VII) is treated with oxalyl chloride using a catalytic amount of N,N-dimethylformamide in a suitable organic solvent, preferably dichloromethane. After evaporation of the volatile components, the acyl chloride is reacted with the corresponding amine in the presence of a suitable base, e.g., triethylamine, diisopropylethylamine or tripotassium phosphate in a suitable solvent, e.g., dichloromethane, 1,2-dichloroethane or tetrahydrofuran. The reaction is carried out at 25-80° C. The necessary reaction time is 3-16 hours. The reaction mixture is worked up either by evaporation of the solvent, or poured onto aqueous hydrochloric acid solution, and extracted with a suitable organic solvent, e.g., ethyl acetate or dichloromethane. The product is isolated by column chromatography. The structures of the products are determined by NMR and mass spectrometry.

Step 6

The reaction of N-alkylated ester of formula (VI) with the corresponding amine is carried out in the presence of a strong base, preferably triethyl aluminium, in a suitable solvent, e.g., 1,2-dichloroethane or toluene at 50-110° C. The necessary reaction time is 6-48 hours. The reaction mixture is vigorously stirred with aqueous hydrochloric acid solution at 25-40° C. The product is isolated by extraction with a suitable organic solvent, e.g., ethyl acetate or dichloromethane and by subsequent column chromatography. The structures of the products are determined by NMR and mass spectrometry.

Route B)

Step 7

Hydrolysis of 1,1-dioxo-1,3-thiadiazine carboxylic acid ester derivative of formula (V) is carried out with a base, e.g., 5 M aqueous NaOH solution in a suitable solvent, e.g., tetrahydrofuran, or preferably ethanol at room temperature. The necessary reaction time is 1-3 hours. The product is isolated in two different ways.

i) The reaction mixture is neutralised with aqueous hydrochloric acid solution, and evaporated to dryness in vacuo, the product—which contains sodium chloride-, obtained in this way was used in the next step without further purification.

ii) The reaction mixture is neutralised with aqueous hydrochloric acid solution. The organic solvent is evaporated in vacuo, the aqueous residue is acidified to pH=1-2 and the product is isolated by filtration.

Step 8

N,O-dialkylation of 1,1-dioxo-1,3-thiadiazine carboxylic acid derivative of formula (VIII) with a suitable primary alkyl halogenide or pseudohalogenide, such as propyl bromide, butyl bromide or 2-bromoethyl methylether is carried out in a suitable solvent, preferably acetonitrile or N,N-dimethyl formamide, in the presence of a suitable amine, e.g., triethyl amine, diisopropyl ethylamine or sodium hydride at 65-80° C. The necessary reaction time is 2-24 hours. The reaction mixture is diluted with water and acidified with aqueous hydrochloric acid solution. The product is isolated by extraction with a suitable organic solvent, preferably ethyl acetate, and the isomers of product are separated by column chromatography. The structures of the products are determined by NMR spectroscopy and mass spectrometry.

Step 9

Hydrolysis of N-alkylated ester of formula (X) is carried out with a base, e.g., 1-2 M NaOH or LiOH solution in a suitable solvent, e.g., tetrahydrofuran, or preferably ethanol at room temperature. The necessary reaction time is 1-3 hours. The reaction mixture is neutralised with aqueous hydrochloric acid solution. The organic solvent is evaporated in vacuo, the aqueous residue is acidified to pH=1-2, and the product is isolated by filtration or extraction with a suitable organic solvent, preferably ethyl acetate.

Amidation of N-alkylated carboxylic acid of formula (VII) to provide amide of formula (I) is performed as described in Step 5 above.

The reaction of N-alkylated ester of formula (X) with the corresponding amine is carried out as described in Step 6 above.

The present disclosure includes within its scope all the possible isotopically labelled forms of the compounds.

The compounds of the present invention can be administered by oral, parenteral (e.g., intramuscular, intraperitoneal, intravenous, intraarticular, intrathecal, intraperitoneal, direct intraventricular, intracerebroventicular, intramedullary injection, intracisternal injection or infusion, subcutaneous injection or implant), ophthalmic, nasal, vaginal, rectal, sublingual and topical routes of administration and may be formulated, alone or together, in suitable dosage unit formulations comprising pharmaceutically acceptable excipients suitable for each route of administration.

Alternatively, one may administer the compounds in a local rather than systemic manner, for example, via injection of the compound directly in the renal or cardiac area, often in a modified release formulation. Furthermore, one may administer the drug in a targeted drug delivery system, for example, in a liposome coated with a tissue-specific antibody. The liposomes are taken up selectively by the targeted organ.

The pharmaceutical compositions of the present invention usually contain 0.01 to 500 mg of the active ingredient in a single dosage unit. However, it is possible that the amount of the active ingredient in some compositions exceeds the upper or lower limits defined above.

The compounds may be administered on a regimen of 1 to 4 times per day, preferably once or twice per day.

This dosage level and regimen can be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition and the host undergoing therapy.

As a further aspect of the invention, there is provided the pharmaceutical manufacture of medicaments containing the compounds of formula (I) or pharmaceutically acceptable salts, biologically active metabolites, pro-drugs, racemates, enantiomers, diastereomers, solvates and hydrates thereof.

The pharmaceutical compositions of the present invention may be formulated as different pharmaceutical dosage forms, including, but not limited to, solid oral dosage forms like tablets (e.g., buccal, sublingual, effervescents, chewable, orodispersible, freeze dried), capsules, lozenges, pastilles, pills, orodispersible films, granules, powders; liquid oral dosage forms, including, but not limited to, solutions, emulsions, suspensions, syrups, elixirs, oral drops; parenteral dosage forms, including, but not limited to, intravenous injections, intramuscular injections, subcutaneous injections; other dosage forms, including, but not limited to, eye drops, semi-solid eye preparations, nasal drops or sprays, transdermal dosage forms, suppositories, rectal capsules, rectal solutions, emulsions and suspensions, etc.

The pharmaceutical compositions of the present invention can be manufactured in any conventional manner, e.g., by mixing, dissolving, emulsifying, suspending, entrapping, freeze-drying, extruding, laminating, film-casting, granulating, grinding, encapsulating, dragee-making or tabletting processes.

Pharmaceutical compositions for use in accordance with the present invention thus can be formulated in any conventional manner using one or more physiologically acceptable excipients. Any of the well-known techniques and excipients may be used as suitable and as understood in the art.

Suitable excipients for the preparation of the dosage forms may be selected from the following categories, including, but not limited to, tablet and capsule fillers, tablet and capsule binders, release modifying agents, disintegrants, glidants, lubricants, sweetening agents, taste-masking agents, flavoring agents, coating agents, surfactants, antioxidants, buffering agents, complexing agents, emulsifying agents, lyophilization aids, microencapsulating agents, ointment bases, penetration enhancers, solubilizing agents, solvents, suppository bases, and suspending agents.

In one embodiment, the invention relates to the use of specific excipients which are capable of improving the solubility, dissolution, penetration, absorption and/or bioavailability of the active ingredient(s), including, but not limited to, hydrophilic polymers, hot melt extrusion excipients, surfactants, buffering agents, complexing agents, emulsifying agents, lyophilization aids, superdisintegrants, microencapsulating agents, penetration enhancers, solubilizing agents, co-solvents, and suspending agents.

The above described ingredients and different routes of manufacture are merely representative. Other materials as well as processing techniques and the like well known in the art can also be used.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In general, the compounds of formula (I) can be prepared in accordance with the general knowledge of one skilled in the art and/or using methods set forth in the Example and/or Intermediate sections that follow. Solvents, temperatures, pressures, and other reaction conditions can readily be selected by one of ordinary skill in the art. Starting materials are commercially available and/or readily prepared by one skilled in the art.

The present invention will be now illustrated by the following not limiting examples.

In the following examples "room temperature" denotes a temperature in the range from 20° C. to 25° C.

The abbreviations used in the specific examples have the following meanings:

| | |
|---|---|
| AlEt₃ | triethylaluminium |
| conc. | concentrated |
| DMSO | dimethyl sulfoxide |
| EDC | (1-ethyl-3-(3-dimethylaminopropyl)carbodiimide) |
| ESI | electronspray ionisation |
| HATU | (1-[bis(dimethylamino)methylene]-1H-1,2,3-triazolo[4,5-b]pyridinium 3-oxide hexafluorophosphate) |
| HEPES | (4-(2-hydroxyethyl)-1-piperazineethanesulfonic acid) |
| LC-MS | liquid chromatography coupled with mass spectroscopy |
| THF | tetrahydrofuran |

Step 1

Intermediate 1

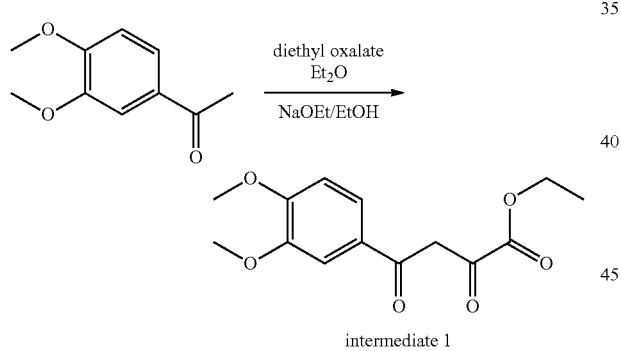

intermediate 1

Ethyl 4-(3,4-dimethoxyphenyl)-2,4-dioxobutanoate

In an inert atmosphere, diethyl oxalate (20 ml, 0.15 mol) was added to a sodium ethylate solution freshly prepared from sodium (3.5 g, 0.15 mol) and ethanol (300 mL). A solution of 1-(3,4-dimethoxyphenyl)ethanone (9.20 g, 0.05 mol) in diethyl ether (150 mL) was added dropwise, and the mixture was stirred for 2 hours at room temperature.

The reaction mixture was poured onto ice-water (500 mL) and acidified to pH=1-2 by the addition of 6 M HCl solution during cooling with ice. The yellow precipitate was collected by filtration, washed with water, and dried under vacuum at room temperature. Yield: 13.5 g (94%) yellow solid, m/z (M+H)⁺: 281.2

The intermediates in Table 1 were synthesized according to the procedure described for Intermediate 1. All necessary starting materials were purchased from different vendors.

TABLE 1

| Intermediate | Structure |
|---|---|
| 2 | [structure] |
| 3 | [structure] |
| 4 | [structure] |
| 5 | [structure] |
| 6 | [structure] |
| 7 | [structure] |
| 8 | [structure] |
| 9 | [structure] |

TABLE 1-continued

| Intermediate | Structure |
|---|---|
| 10 | 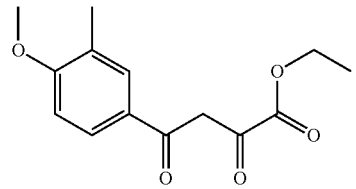 [SMILES: CCOC(=O)C(=O)CC(=O)c1ccc(OC)c(C)c1] |
| 11 | 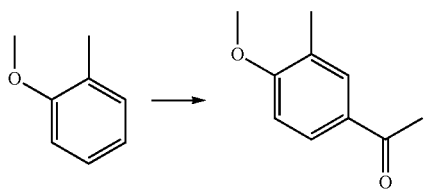 |

Intermediate 12

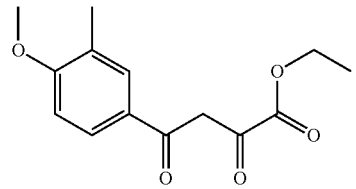 [SMILES: CCOC(=O)C(=O)CC(=O)c1ccc(OC)c(C)c1]

Ethyl 4-(4-methoxy-3-methylphenyl)-2,4-dioxobutanoate

The title compound was prepared from 1-(4-methoxy-3-methylphenyl)ethanone according to the method described for Intermediate 1.

1-(4-methoxy-3-methylphenyl)ethanone was synthesized according to the following method:

Under an inert atmosphere, to a solution of 2-methylanisol (7.92 g, 64.8 mmol) in dichloromethane (40 mL), aluminium chloride (9.45 g, 70.9 mmol) was added. To the obtained mixture (5.1 mL, 71.5 mmol) acetyl chloride was added dropwise, and the mixture was heated under reflux for 2 hours.

The reaction mixture was poured slowly onto 3 M HCl solution and extracted with diethyl ether. The combined organic layer was washed with saturated $NaHCO_3$ solution and brine, dried over $Na_2SO_4$ and evaporated to dryness. Yield: 10.33 g (97%) light yellow oil.

Intermediate 13

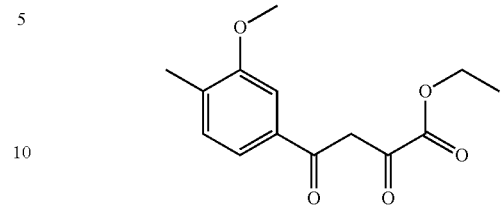

Ethyl 4-(3-methoxy-4-methylphenyl)-2,4-dioxobutanoate

The title compound was prepared from 1-(3-methoxy-4-methylphenyl)ethanone according to the method described for Intermediate 1.

1-(3-methoxy-4-methylphenyl)ethanone was synthesized according to the following method:

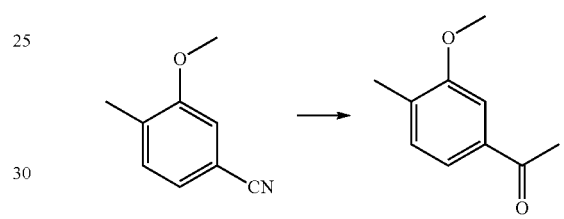

Under an inert atmosphere, to a solution of 3-methoxy-4-methylbenzonitrile (2.00 g, 13.6 mmol) in tetrahydrofuran (50 mL), a methylmagnesium chloride solution (5 mL, 3M in tetrahydrofuran) was added dropwise during cooling with ice at 0-2° C., and the mixture was stirred at 40° C. for 12 hours.

The reaction mixture was quenched by dropwise addition of 6 M HCl solution (3.4 mL), and was stirred stirred at 40° C. for another hour. The mixture was extracted with ethyl acetate, the combined organic layer was washed with brine, dried over $Na_2SO_4$, evaporated, and the crude residue was purified with column chromatography on silica gel with gradient elution, using a mixture of dichloromethane and cyclohexane as eluent. Yield: 356 mg (16%/).

Intermediate 14

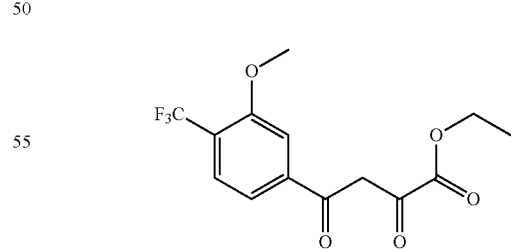

Ethyl 4-[3-methoxy-4-(trifluoromethyl)phenyl]-2,4-dioxobutanoate

The title compound was prepared from 1-(3-methoxy-4-trifluoromethylphenyl)ethanone according to the method described for Intermediate 1.

1-[3-methoxy-4-(trifluoromethyl)phenyl]ethanone was synthesized according to the following method:

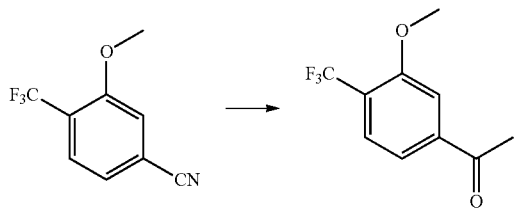

Under an inert atmosphere, to a solution of 3-methoxy-4-(trifluoromethyl)benzonitrile (4.11 g, 20.4 mmol) in diethyl ether (100 mL), a methylmagnesium chloride solution (7.5 mL, 3M in tetrahydrofuran) was added dropwise during cooling with ice at 0-2° C., and the mixture was stirred at room temperature further for 2 hours.

The reaction mixture was quenched by dropwise addition of 6 M HCl solution (100 mL), and was stirred at room temperature for another hour. The mixture was extracted with ethyl acetate, the combined organic layer was washed with brine, dried over $Na_2SO_4$, evaporated, and the crude residue was purified with column chromatography on silica gel, using a 1:9 mixture of ethyl acetate and cyclohexane as eluent. Yield: 600 mg (13%) yellow solid.

Intermediate 15

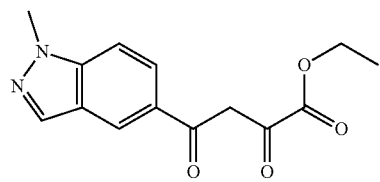 [SMILES: CCOC(=O)C(=O)CC(=O)c1ccc2c(cnn2C)c1]

Ethyl 4-(1-methyl-1H-indazol-5-yl)-2,4-dioxobutanoate

The title compound was prepared from 1-(1-methyl-1H-indazol-5-yl)ethanone according to the method described for Intermediate 1.

1-(1-methyl-1H-indazol-5-yl)ethanone was synthesized according to the following method:

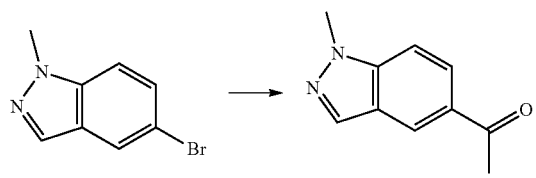

A solution of 5-bromo-1-methyl-1H-indazole (2.91 g, 13.8 mmol) in N-methyl-2-pyrrolidone (55 mL) was purged with argon gas for 15 minutes. Tripotassium phosphate (5.85 g, 27.6 mmol), tributyl(1-ethoxyvinyl)tin (4.7 mL, 13.9 mmol) and tetrakis(triphenylphosphine)palladium(0) (0.80 g, 0.69 mmol) were added, and the mixture was stirred at 80-90° C. for 6 hours under argon atmosphere. The reaction mixture was diluted with water, and extracted with ethyl acetate. The organic phase was treated with 1 M hydrochloric acid solution at room temperature by vigorously stirring for 30 minutes. The pH of the mixture was adjusted to 7-8 by the addition of 25% w/w aqueous ammonia solution, and extracted with ethyl acetate. The organic phase was washed with water, dried over $Na_2SO_4$, and evaporated to dryness. The residue was purified by column chromatography on silica gel using a mixture of ethyl acetate and cyclohexane (3:1) as eluent. Yield: 1.64 g (68%).

Intermediate 16

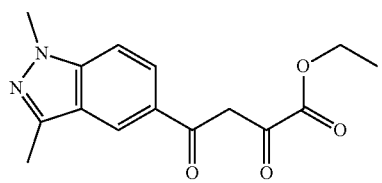 [SMILES: CCOC(=O)C(=O)CC(=O)c1ccc2c(c1)c(C)nn2C]

Ethyl 4-(1,3-dimethyl-1H-indazol-5-yl)-2,4-dioxobutanoate

The title compound was prepared from 1-(1,3-dimethyl-1H-indazol-5-yl)ethanone according to the method described for Intermediate 1.

1-(1,3-dimethyl-1H-indazol-5-yl)ethanone was prepared from 5-bromo-1,3-dimethyl-1H-indazol according to the method described for Intermediate 15.

5-bromo-1,3-dimethyl-1H-indazol was synthesized according to the following method:

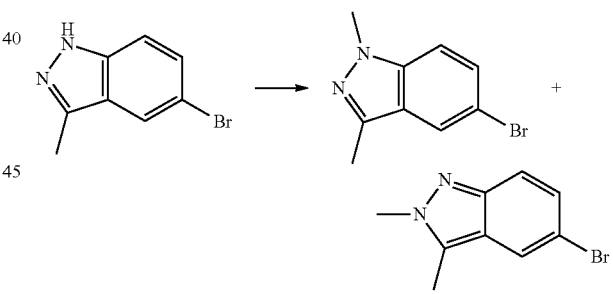

To a suspension of sodium hydride (0.98 g, 24.5 mmol, 60% in mineral oil) in N,N-dimethylformamide (70 mL), 5-bromo-3-methyl-1H-indazol (4.30 g, 20.4 mmol) was added in portions under an inert atmosphere at room temperature, and the obtained suspension was stirred further for 15 minutes. Iodomethane (1.7 ml, 27.5 mmol) was added, and the mixture was stirred further for 3 hours at room temperature. Water was added, and the mixture was extracted with ethyl acetate. The organic phase was washed with 2 M $Na_2S_2O_3$ solution and water, dried over $Na_2SO_4$, and evaporated to dryness. The regioisomeric products were separated by column chromatography on silica gel, using a mixture of ethyl acetate and cyclohexane (2:1) as eluent. Yield: 3.16 g (69%) for the desired product 5-bromo-1,3-dimethyl-1H-indazol and 1.26 g (27%) for 5-bromo-2,3-dimethyl-1H-indazol.

Intermediate 17

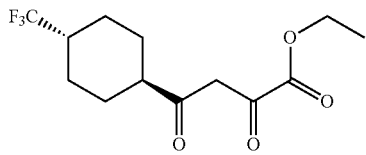 [SMILES: CCOC(=O)C(=O)CC(=O)[C@H]1CC[C@H](C(F)(F)F)CC1]

Ethyl 2,4-dioxo-4-[(1r,4r)-4-(trifluoromethyl)cyclohexyl]butanoate

The title compound was prepared from 1-[trans-4-(trifluoromethyl)cyclohexyl]ethanone according to the method described for Intermediate 1.

1-[trans-4-(trifluoromethyl)cyclohexyl]ethanone was synthesized according to the following method:

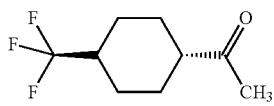

Under argon, atmosphere to a solution of trans-4-(trifluoromethyl)cyclohexanecarboxylic acid (3.14 g, 16 mmol) in dry diethyl ether (75 mL), a methyl lithium solution in diethyl ether (1.6 M, 25 mL, 40 mmol) was added dropwise at −20° C. to 15° C. for 45-60 minutes, and the mixture was stirred further at −15° C. for 1 hour. The reaction mixture was quenched by addition of saturated NH$_4$Cl solution (25 mL) (pH~8) and water (25 mL) at 0° C., and extracted with diethyl ether. The combined organic layer was dried over Na$_2$SO$_4$, filtered and concentrated in vacuo (at 350-400 mbar at room temperature). Yield: 3.075 g (99%) colourless oil.

Intermediate 18

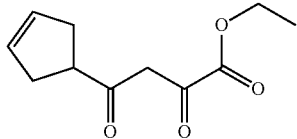

Ethyl 4-(cyclopent-3-en-1-yl)-2,4-dioxobutanoate

The title compound was prepared from 1-(cyclopent-3-en-1-yl)ethanone according to the method described for Intermediate 1.

1-(cyclopent-3-en-1-yl)ethanone was synthesized according to the following method:

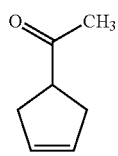

To a solution of cyclopent-3-ene-1-carboxylic acid (1.346 g, 12 mmol) and a few drops of N,N-dimethylformamide in dry dichloromethane (30 mL), oxalyl chloride (2.03 mL, 24 mmol) in dichloromethane (5 mL) was added dropwise at 25° C. under argon atmosphere. The reaction mixture was stirred for 30 minutes and the volatile components were removed in vacuo. The obtained cyclopent-3-ene-1-carbonyl chloride was dissolved in dichloromethane (25 mL), and the solution was added dropwise to a mixture of N,O-dimethylhydroxylamine hydrochloride (1.117 g, 12 mmol) and triethylamine (3.68 mL, 26.41 mmol) in dry dichloromethane (25 mL) at 25° C. The reaction mixture was concentrated in vacuo and suspended in ethyl acetate (30 mL). The suspension was filtered, and the filtrate was concentrated in vacuo. The residue was chromatographed on silica gel, eluting with a mixture of cyclohexane and ethyl acetate (7:3) to yield 1.043 g (78%) of the Weinreb amide.

To a solution of Weinreb amide (1.043 g, 6.1 mmol) in diethyl ether (50 mL), a methyl lithium solution in diethyl ether (1.6 M, 4.54 mL, 7.26 mmol) was added dropwise at −65° C. to −78° C., and the mixture was stirred further at −78° C. for 2 hours. The reaction mixture was allowed to warm to 0° C., and quenched by the addition of 1 M HCl solution (10 mL) and water (10 mL) during ice cooling. The reaction mixture was extracted with diethyl ether, the combined organic layer was dried over Na$_2$SO$_4$, filtered and concentrated in vacuo (at 350-400 mbar at room temperature). The title compound was obtained (0.663 g, 99%) as an oil.

Step 2

Intermediate 19

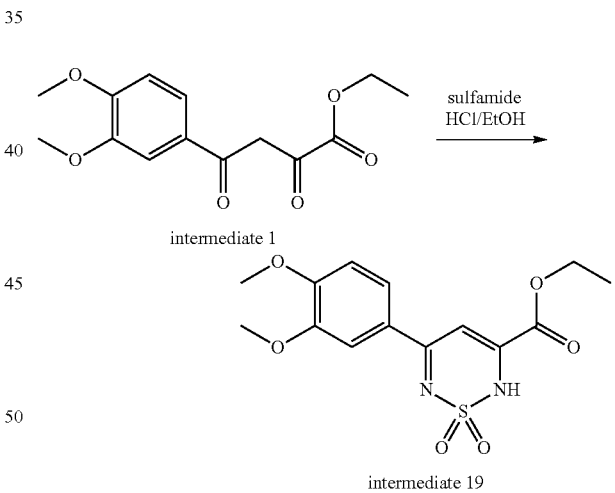

Ethyl 5-(3,4-dimethoxyphenyl)-1,1-dioxo-2H-1$\lambda^6$,2,6-thiadiazine-3-carboxylate To a suspension of Intermediate 1 (ethyl 4-(3,4-dimethoxyphenyl)-2,4-dioxobutanoate, 13.5 g, 48.2 mmol) in ethanol (280 mL), sulfamide (9.4 g, 98 mmol) and ethanol saturated with hydrogen chloride (30%, 35 mL) was added, and the mixture was stirred at 60° C. (inner) overnight. The obtained suspension was cooled in an ice-water bath, and the yellow precipitate was collected by filtration, washed with cold ethanol, and dried in vacuo at 40° C. Yield: 15.79 g (96%) yellow solid, m/z (M+H)$^+$: 341.1

The following intermediates in Table 2 were synthesized from the corresponding intermediates (1-18) according to the procedure described for Intermediate 19.

TABLE 2

| Intermediate | Structure | Starting intermediate |
|---|---|---|
| 20 | 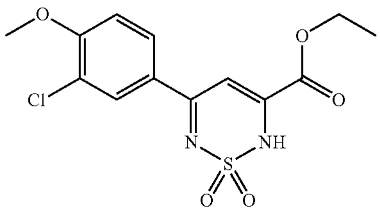 [SMILES: CCOC(=O)C1=CC(c2ccc(OC)c(Cl)c2)=NS(=O)(=O)N1] | 2 |
| 21 | 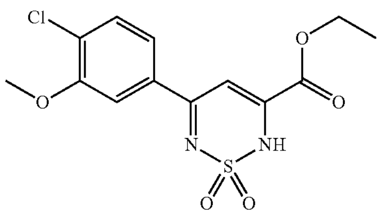 [SMILES: CCOC(=O)C1=CC(c2ccc(Cl)c(OC)c2)=NS(=O)(=O)N1] | 3 |
| 22 | 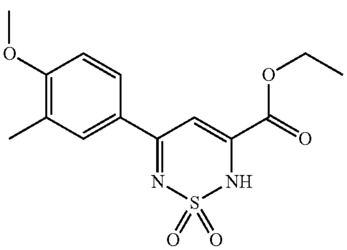 [SMILES: CCOC(=O)C1=CC(c2ccc(OC)c(C)c2)=NS(=O)(=O)N1] | 12 |
| 23 | 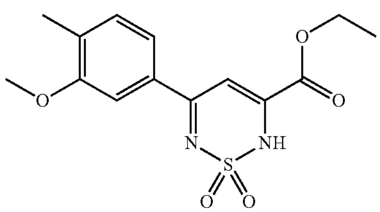 [SMILES: CCOC(=O)C1=CC(c2ccc(C)c(OC)c2)=NS(=O)(=O)N1] | 13 |
| 24 | 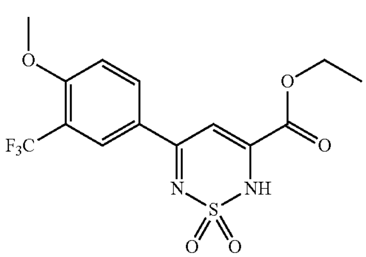 [SMILES: CCOC(=O)C1=CC(c2ccc(OC)c(C(F)(F)F)c2)=NS(=O)(=O)N1] | 4 |
| 25 | 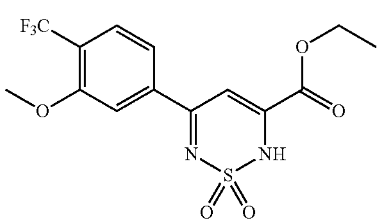 [SMILES: CCOC(=O)C1=CC(c2ccc(C(F)(F)F)c(OC)c2)=NS(=O)(=O)N1] | 14 |

TABLE 2-continued

| Intermediate | Structure | Starting intermediate |
|---|---|---|
| 26 | 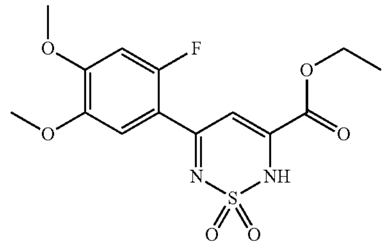 [SMILES: CCOC(=O)C1=CC(c2cc(OC)c(OC)cc2F)=NS(=O)(=O)N1] | 5 |
| 27 | 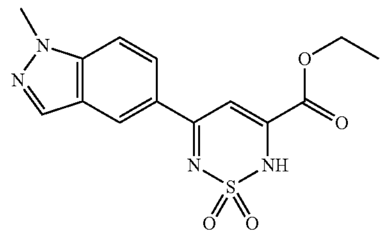 [SMILES: CCOC(=O)C1=CC(c2ccc3c(cnn3C)c2)=NS(=O)(=O)N1] | 15 |
| 28 | 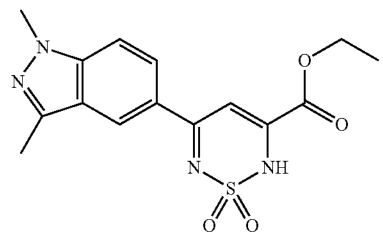 [SMILES: CCOC(=O)C1=CC(c2ccc3c(c2)c(C)nn3C)=NS(=O)(=O)N1] | 16 |
| 29 | 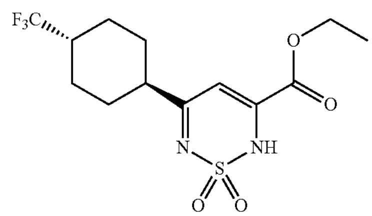 [SMILES: CCOC(=O)C1=CC([C@H]2CC[C@H](C(F)(F)F)CC2)=NS(=O)(=O)N1] | 17 |
| 30 | 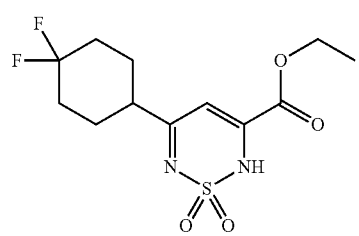 [SMILES: CCOC(=O)C1=CC(C2CCC(F)(F)CC2)=NS(=O)(=O)N1] | 6 |
| 31 | 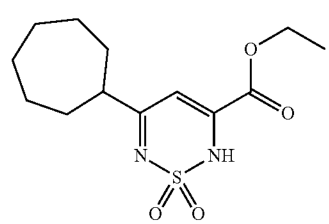 [SMILES: CCOC(=O)C1=CC(C2CCCCCC2)=NS(=O)(=O)N1] | 7 |

TABLE 2-continued

| Intermediate | Structure | Starting intermediate |
|---|---|---|
| 32 | 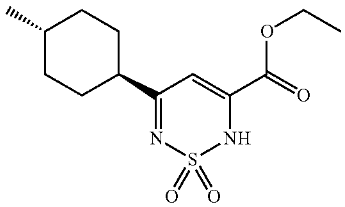 [SMILES: CCOC(=O)C1=CC([C@H]2CC[C@H](C)CC2)=NS(=O)(=O)N1] | 8 |
| 33 | 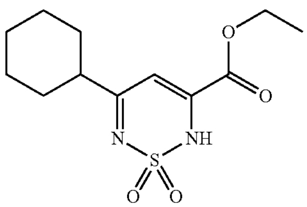 [SMILES: CCOC(=O)C1=CC(C2CCCCC2)=NS(=O)(=O)N1] | 9 |
| 34 | 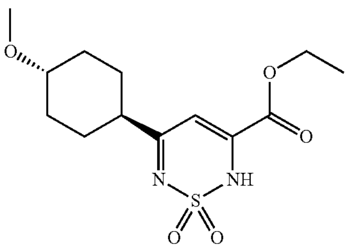 [SMILES: CCOC(=O)C1=CC([C@H]2CC[C@H](OC)CC2)=NS(=O)(=O)N1] | 10 |
| 35 | 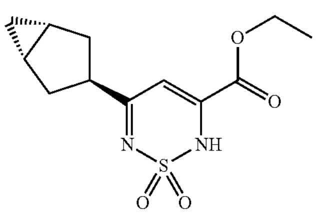 [SMILES: CCOC(=O)C1=CC([C@H]2C[C@@H]3C[C@@H]3C2)=NS(=O)(=O)N1] | 11 |
| 36 | 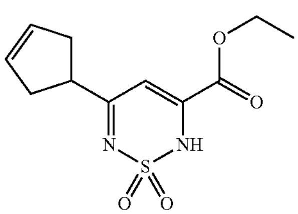 [SMILES: CCOC(=O)C1=CC(C2CC=CC2)=NS(=O)(=O)N1] | 18 |

Step 3

Intermediate 37

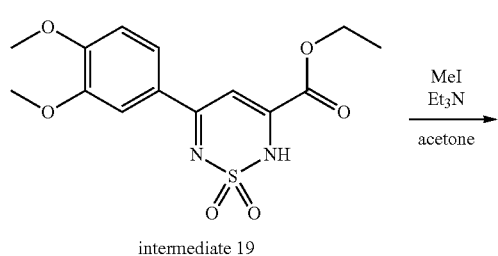

intermediate 19 → (MeI, Et₃N, acetone) →

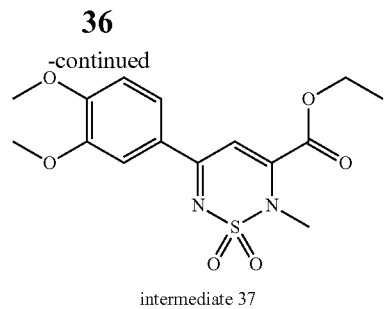

intermediate 37

Ethyl 5-(3,4-dimethoxyphenyl)-2-methyl-1,1-dioxo-2H-1λ$^6$,2,6-thiadiazine-3-carboxylate A mixture of Intermediate 19 (8.26 g, 24.27 mmol), triethylamine (3.7 mL, 26.7 mmol) and iodomethane (17 mL, 273 mmol) in acetone (430 mL) was stirred at 56° C. for 4.5 hours.

The solvent was removed under reduced pressure, to the residue 5% HCl solution (120 mL) was added, and the mixture was extracted with dichloromethane. The organic phase was washed with water, 5% $Na_2S_2O_3$ solution and water again. The combined organic layer was dried over $Na_2SO_4$, filtered, concentrated in vacuo and the residue was purified by column chromatography on silica gel, using a stepwise gradient of a mixture of cyclohexane and diisopropyl ether (40:1 to 10:1) as the eluent, to give 5.60 g (65%) of the product as yellow crystals.

The following intermediates in Table 3 were synthesized from the corresponding intermediates (see them in step 2) according to the procedure described for Intermediate 37.

TABLE 3

| Intermediate | Structure | Starting intermediate |
|---|---|---|
| 38 | 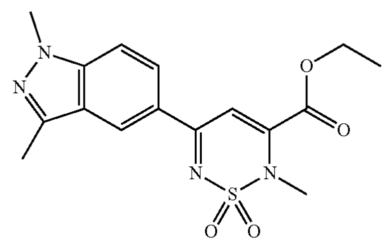 [SMILES: CCOC(=O)C1=CC(c2ccc3c(c2)c(C)nn3C)=NS(=O)(=O)N1C] | 28 |
| 39 | 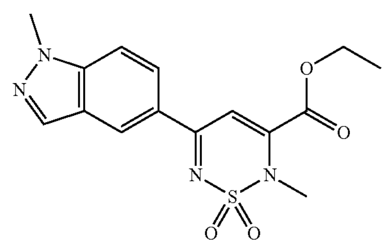 [SMILES: CCOC(=O)C1=CC(c2ccc3c(cnn3C)c2)=NS(=O)(=O)N1C] | 27 |
| 41 | 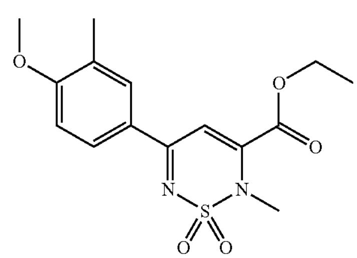 [SMILES: CCOC(=O)C1=CC(c2ccc(OC)c(C)c2)=NS(=O)(=O)N1C] | 22 |

TABLE 3-continued

| Intermediate | Structure | Starting intermediate |
|---|---|---|
| 41 | (structure) | 20 |
| 42 | (structure) | 21 |
| 43* | (structure) | 29 |
| 44 | (structure) | 30 |
| 45 | (structure) | 19 |
| 46 | (structure) | 24 |
| 47 | (structure) | 22 |
| 48 | (structure) | 25 |
| 49 | (structure) | 23 |
| 50* | (structure) | 29 |
| 51* | (structure) | 34 |
| 52* | (structure) | 31 |
| 53* | (structure) | 32 |

TABLE 3-continued

| Intermediate | Structure | Starting intermediate |
|---|---|---|
| 54* | 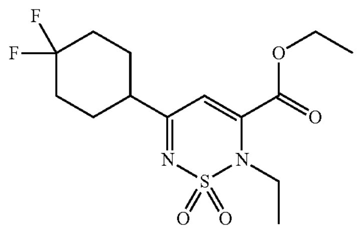 [SMILES: CCOC(=O)C1=CC(C2CCC(F)(F)CC2)=NS(=O)(=O)N1CC] | 30 |
| 55* | 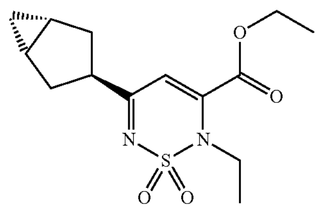 | 35 |
| 56* | 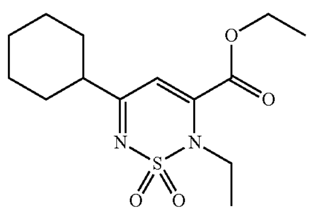 [SMILES: CCOC(=O)C1=CC(C2CCCCC2)=NS(=O)(=O)N1CC] | 33 |
| 57* | 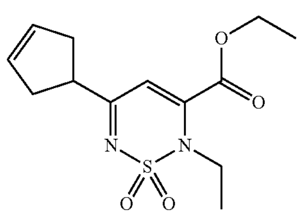 [SMILES: CCOC(=O)C1=CC(C2CC=CC2)=NS(=O)(=O)N1CC] | 36 |

*N,N-dimethylformamide was applied as solvent instead of acetone

Intermediate 58

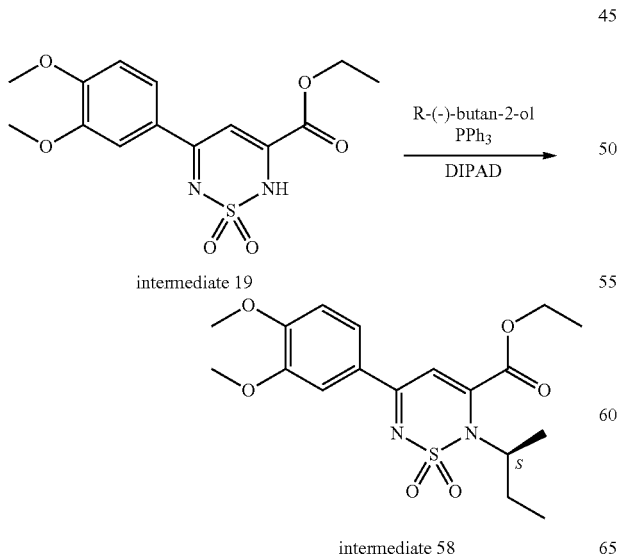

intermediate 19 → intermediate 58 (R-(–)-butan-2-ol, PPh₃, DIPAD)

Ethyl 2-[(2S)-butan-2-yl]-5-(3,4-dimethoxyphenyl)-1,1-dioxo-2H-1λ⁶,2,6-thiadiazine-3-carboxylate To a suspension of Intermediate 19 (ethyl 5-(3,4-dimethoxyphenyl)-1,1-dioxo-2H-1λ⁶,2,6-thiadiazine-3-carboxylate, 3.74 g, 11 mmol), triphenyl phosphine (2.88 g, 11 mmol) and R-(–)-butan-2-ol (0.92 mL, 10 mmol) in a mixture of tetrahydrofuran (50 mL) and N,N-dimethylformamide (10 mL) diisopropyl azodicarboxylate (2.2 mL, 11 mmol) was added dropwise during cooling with ice under an inert atmosphere. The obtained solution was heated under reflux for 7 hours, evaporated to dryness and the residue was purified by flash column chromatography on silica gel in two stages. At first, dichloromethane was used as the eluent, and in the second stage a slow gradient of a mixture of ethyl acetate and dichloromethane was applied. Yield: 460 mg (12%) yellow oil.

The optical purity was not determined in this stage, the product was used in the next step without separating the enantiomers.

The following intermediates in Table 4 were synthesized in Mitsunobu reaction from the Intermediate 19 according to the procedure described for Intermediate 58.

TABLE 4

| Intermediate | Structure |
|---|---|
| 59 | 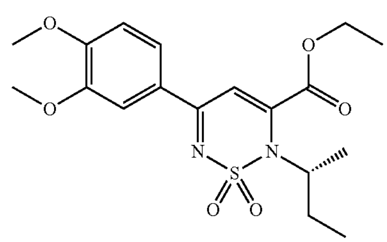 [SMILES: CCOC(=O)C1=CC(c2ccc(OC)c(OC)c2)=NS(=O)(=O)N1[C@H](C)CC] |
| 60 | 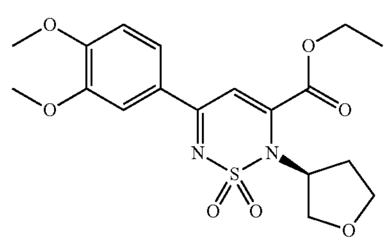 [SMILES: CCOC(=O)C1=CC(c2ccc(OC)c(OC)c2)=NS(=O)(=O)N1[C@H]1CCOC1] |
| 61 | 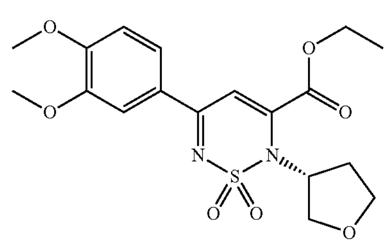 [SMILES: CCOC(=O)C1=CC(c2ccc(OC)c(OC)c2)=NS(=O)(=O)N1[C@@H]1CCOC1] |

Step 4

Intermediate 62

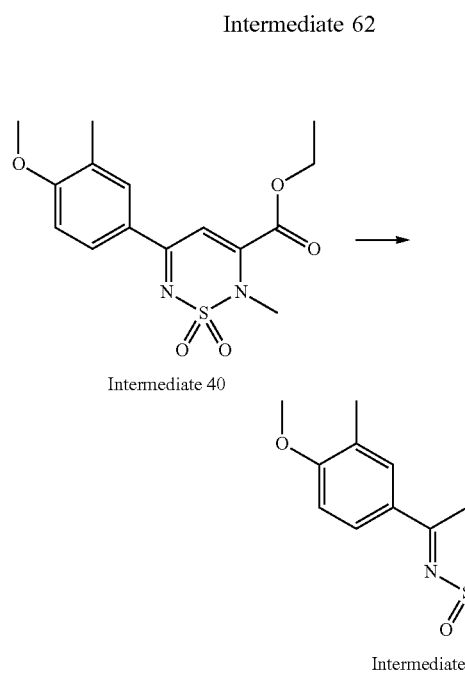

Intermediate 40

Intermediate 62

5-(4-methoxy-3-methylphenyl)-2-methyl-1,1-dioxo-
2H-1λ⁶,2,6-thiadiazine-3-carboxylic Acid To a suspension of intermediate 40 (ethyl 5-(4-methoxy-3-methylphenyl)-2-methyl-1,1-dioxo-2H-1λ⁶,2,6-thiadiazine-3-carboxylate, 520 mg, 1.54 mmol) in ethanol (35 mL), 1 M aqueous NaOH solution (3 mL) was added, and the mixture was stirred at room temperature for 1 hour. The pH of the mixture was adjusted to 4-5 by the addition of 1% HCl solution during cooling with ice. Ethanol was removed under reduced pressure, water was added, and the mixture was acidified further by the addition of 10% HCl to pH=1-2. The mixture was extracted with ethyl acetate, the combined organic layer was washed with brine, dried over $Na_2SO_4$, filtered and evaporated to dryness to give the product in a quantitative yield.

The following intermediates in Table 5 were synthesized via the hydrolysis of the corresponding ester intermediates according to the procedure described for Intermediate 62.

TABLE 5

| Intermediate | Structure | Starting intermediate |
|---|---|---|
| 63* | | 38 |
| 64* | 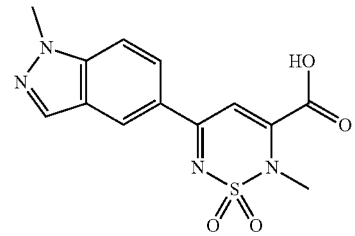 [SMILES: CN1C(C(=O)O)=CC(c2ccc3c(cnn3C)c2)=NS1(=O)=O] | 39 |
| 65 | 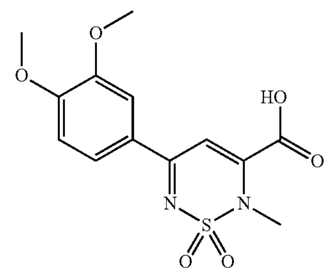 [SMILES: COc1ccc(C2=NS(=O)(=O)N(C)C(C(=O)O)=C2)cc1OC] | 37 |
| 66 | 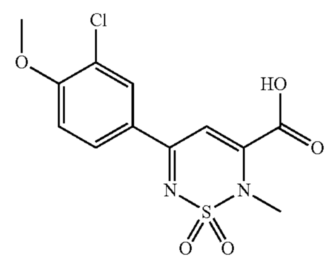 [SMILES: COc1ccc(C2=NS(=O)(=O)N(C)C(C(=O)O)=C2)cc1Cl] | 41 |
| 67 | 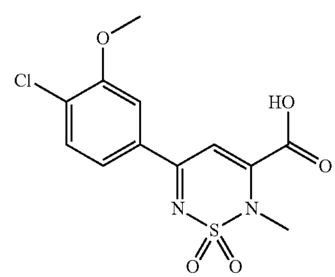 [SMILES: COc1cc(C2=NS(=O)(=O)N(C)C(C(=O)O)=C2)ccc1Cl] | 42 |
| 68 | 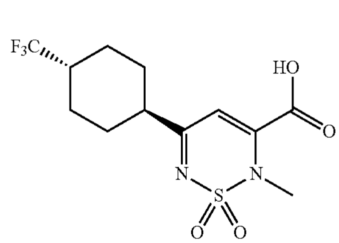 [SMILES: CN1C(C(=O)O)=CC([C@H]2CC[C@H](C(F)(F)F)CC2)=NS1(=O)=O] | 43 |
| 69 | 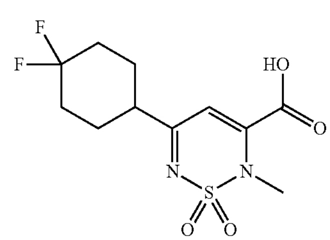 [SMILES: CN1C(C(=O)O)=CC(C2CCC(F)(F)CC2)=NS1(=O)=O] | 44 |

TABLE 5-continued

| Intermediate | Structure | Starting intermediate |
|---|---|---|
| 70 | (3,4-dimethoxyphenyl)-substituted thiadiazine carboxylic acid | 45 |
| 71* | (4-methoxy-3-trifluoromethylphenyl)-substituted thiadiazine carboxylic acid | 46 |
| 72* | (4-methoxy-3-methylphenyl)-substituted thiadiazine carboxylic acid | 47 |
| 73* | (4-trifluoromethyl-3-methoxyphenyl)-substituted thiadiazine carboxylic acid | 48 |
| 74 | (3-methoxy-4-methylphenyl)-substituted thiadiazine carboxylic acid | 49 |
| 75 | (trans-4-trifluoromethylcyclohexyl)-substituted thiadiazine carboxylic acid | 50 |
| 76 | (trans-4-methoxycyclohexyl)-substituted thiadiazine carboxylic acid | 51 |
| 77 | cycloheptyl-substituted thiadiazine carboxylic acid | 52 |
| 78 | (trans-4-methylcyclohexyl)-substituted thiadiazine carboxylic acid | 53 |
| 79 | (4,4-difluorocyclohexyl)-substituted thiadiazine carboxylic acid | 54 |
| 80 | bicyclo[3.1.0]hexyl-substituted thiadiazine carboxylic acid | 55 |
| 81 | cyclohexyl-substituted thiadiazine carboxylic acid | 56 |
| 82 | cyclohexenyl-substituted thiadiazine carboxylic acid | 57 |
| 83 | (3,4-dimethoxyphenyl)-substituted thiadiazine carboxylic acid with sec-butyl N-substituent | 58 |

TABLE 5-continued

| Intermediate | Structure | Starting intermediate |
|---|---|---|
| 84 | (structure) | 59 |
| 85 | (structure) | 60 |
| 86 | (structure) | 61 |

*5 mol equivalents 5M conc. aqueous NaOH solution

Step 5

Example 1

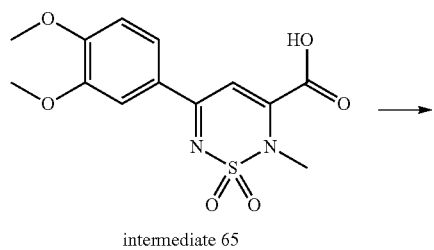

intermediate 65

→

Example 1

5-(3,4-dimethoxyphenyl)-2-methyl-N-(3-methylphenyl)-1,1-dioxo-2H-1$\lambda^6$,2,6-thiadiazine-3-carboxamide Under an inert atmosphere, to a suspension of Intermediate 65 (5-(3,4-dimethoxyphenyl)-2-methyl-1,1-dioxo-2H-1$\lambda^6$,2,6-thiadiazine-3-carboxylic acid, 700 mg, 2.15 mmol) and 1-[bis(dimethylamino)methylene]-1H-1,2,3-triazolo[4,5-b]pyridinium 3-oxid hexafluorophosphate (HATU, 1.06 g, 2.79 mmol) in N,N-dimethylformamide (20 mL) m-toluidine (0.46 mL, 4.3 mmol) and N,N-diisopropylethylamine (1.48 mL, 8.50 mmol) was added during cooling with ice, and the obtained solution was stirred at room temperature for 2 days. 10% HCl solution (100 mL) was added, and the mixture was extracted with ethyl acetate, the combined organic layer was washed with water, dried over $Na_2SO_4$, and evaporated to dryness. The residue was purified by flash column chromatography on silica gel, applying gradient elution with a 0 to 2.5% V/V ethyl acetate-dichloromethane mixture as eluent, and a subsequent crystallization from a mixture of dichloromethane and diethyl ether. Yield: 460 mg (52%) yellow crystals, m/z (M+H)$^+$: 416.1.

The following examples in Table 6 were synthesized according to the procedure (via HATU coupling) described for Example 1.

TABLE 6

| Example | Structure | LC-MS (ESI) m/z (M + H)$^+$ | Starting intermediate |
|---|---|---|---|
| 2 | (structure) | 485.1 | 65 |

TABLE 6-continued
| Example | Structure | LC-MS (ESI) m/z (M + H)+ | Starting intermediate |
|---|---|---|---|
| 3* | 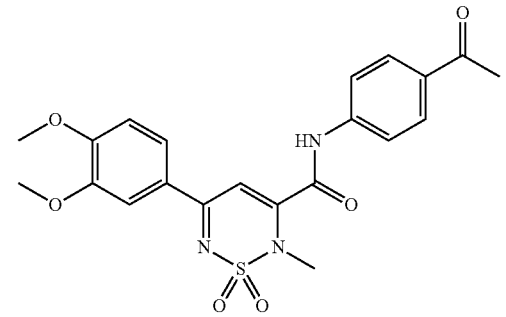 [SMILES: COc1ccc(C2=NS(=O)(=O)N(C)C(C(=O)Nc3ccc(C(C)=O)cc3)=C2)cc1OC] | | purchased library compound |
| 4 | 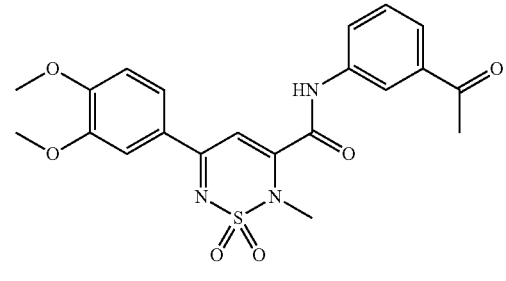 [SMILES: COc1ccc(C2=NS(=O)(=O)N(C)C(C(=O)Nc3cccc(C(C)=O)c3)=C2)cc1OC] | 444.1 | 65 |
| 5 | 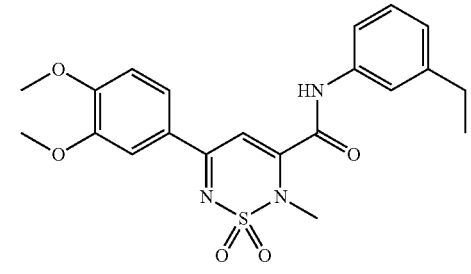 [SMILES: CCc1cccc(NC(=O)C2=CC(c3ccc(OC)c(OC)c3)=NS(=O)(=O)N2C)c1] | 430.2 | 65 |
| 6 | 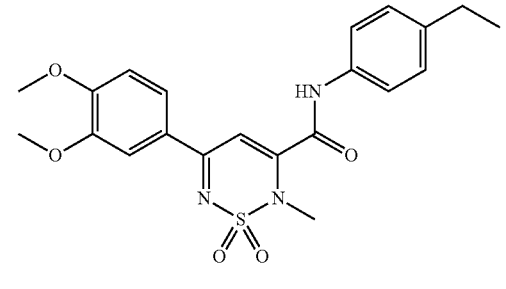 [SMILES: CCc1ccc(NC(=O)C2=CC(c3ccc(OC)c(OC)c3)=NS(=O)(=O)N2C)cc1] | 430.1 | 65 |
| 7 | 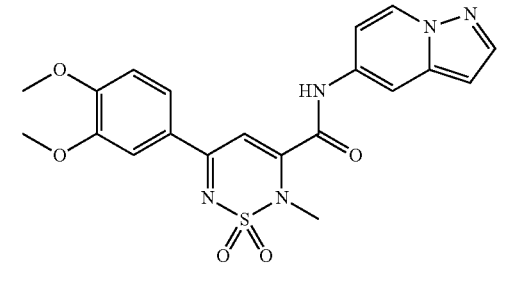 [SMILES: COc1ccc(C2=NS(=O)(=O)N(C)C(C(=O)Nc3ccn4nccc4c3)=C2)cc1OC] | 442.1 | 65 |

TABLE 6-continued

| Example | Structure | LC-MS (ESI) m/z (M + H)⁺ | Starting intermediate |
|---|---|---|---|
| 8 | 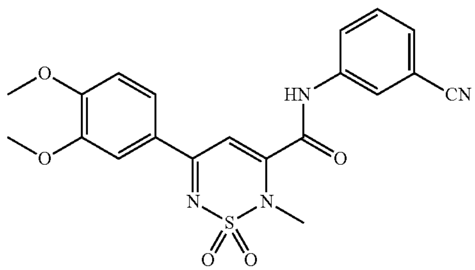 [SMILES: COc1ccc(C2=NS(=O)(=O)N(C)C(C(=O)Nc3cccc(C#N)c3)=C2)cc1OC] | 427.1 | 65 |
| 9 | 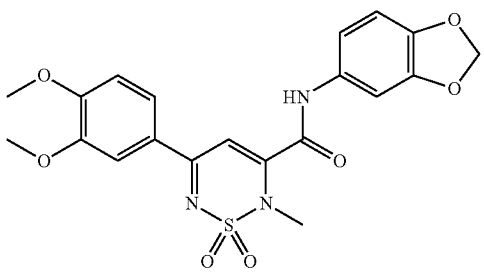 [SMILES: COc1ccc(C2=NS(=O)(=O)N(C)C(C(=O)Nc3ccc4c(c3)OCO4)=C2)cc1OC] | 446.0 | 65 |
| 10 | 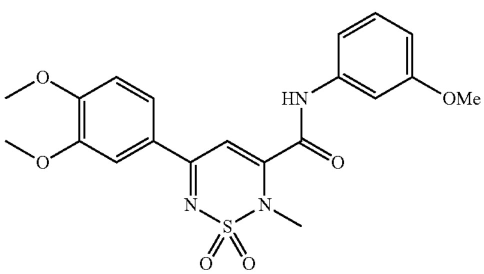 [SMILES: COc1cccc(NC(=O)C2=CC(c3ccc(OC)c(OC)c3)=NS(=O)(=O)N2C)c1] | 432.1 | 65 |
| 11 | 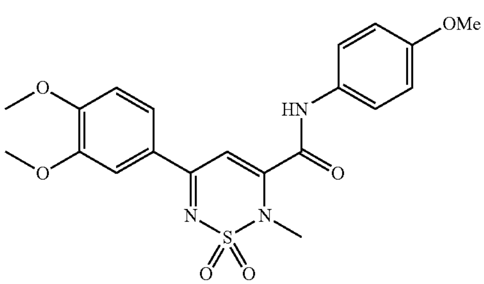 [SMILES: COc1ccc(NC(=O)C2=CC(c3ccc(OC)c(OC)c3)=NS(=O)(=O)N2C)cc1] | 432.1 | 65 |
| 12 | 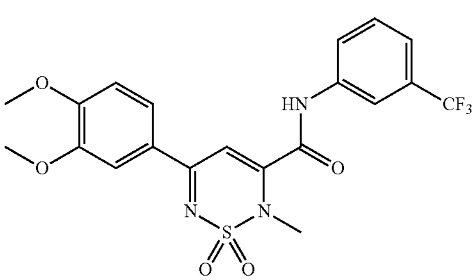 [SMILES: COc1ccc(C2=NS(=O)(=O)N(C)C(C(=O)Nc3cccc(C(F)(F)F)c3)=C2)cc1OC] | 470.2 | 65 |

TABLE 6-continued

| Example | Structure | LC-MS (ESI) m/z (M + H)+ | Starting intermediate |
|---|---|---|---|
| 13 | 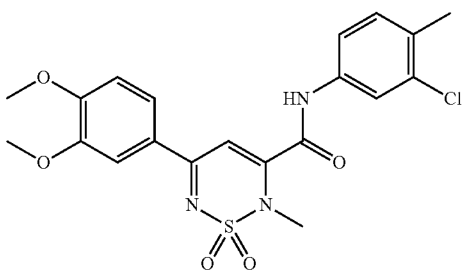 [SMILES: COc1ccc(C2=NS(=O)(=O)N(C)C(C(=O)Nc3ccc(C)c(Cl)c3)=C2)cc1OC] | 450.1 | 65 |
| 14 | 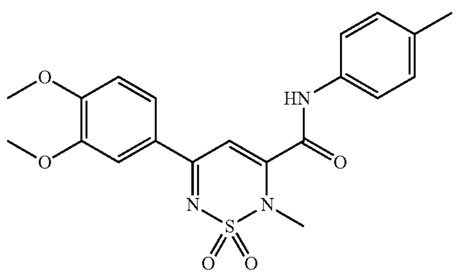 | 416.1 | 65 |
| 15 | 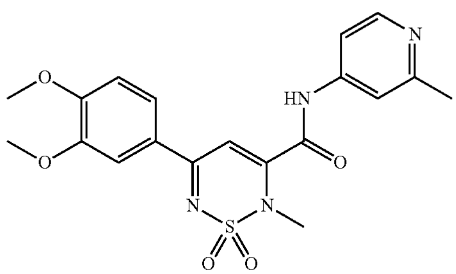 | 417.1 | 65 |
| 16 | 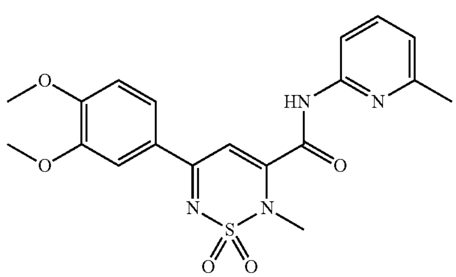 | 417.1 | 65 |
| 17 | 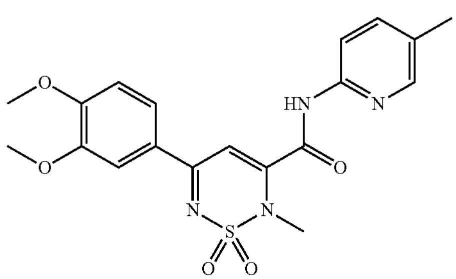 | 417.1 | 65 |

TABLE 6-continued

| Example | Structure | LC-MS (ESI) m/z (M + H)+ | Starting intermediate |
| --- | --- | --- | --- |
| 18 | 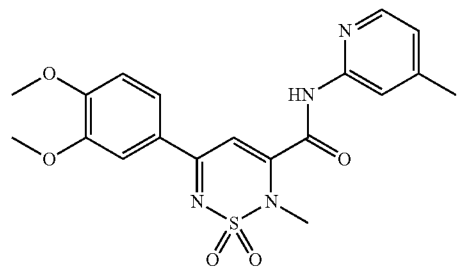 | 417.1 | 65 |
| 19 | 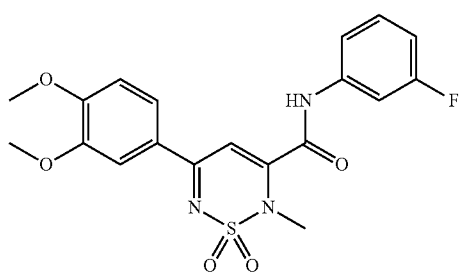 [SMILES: COc1ccc(C2=NS(=O)(=O)N(C)C(C(=O)Nc3cccc(F)c3)=C2)cc1OC] | 420.1 | 65 |
| 20 | 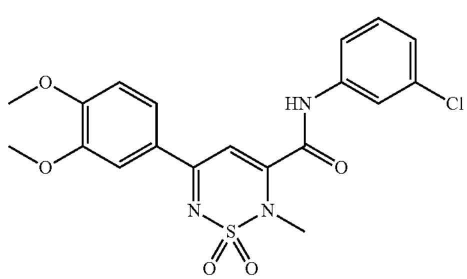 [SMILES: COc1ccc(C2=NS(=O)(=O)N(C)C(C(=O)Nc3cccc(Cl)c3)=C2)cc1OC] | 436.1 | 65 |
| 21 | 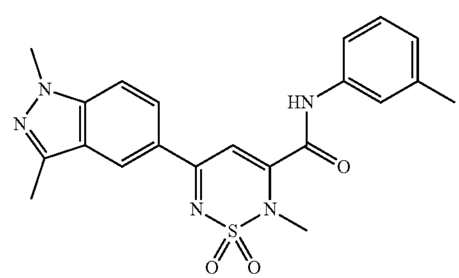 [SMILES: Cc1cccc(NC(=O)C2=CC(c3ccc4c(c3)c(C)nn4C)=NS(=O)(=O)N2C)c1] | 424.1 | 63 |
| 22 | 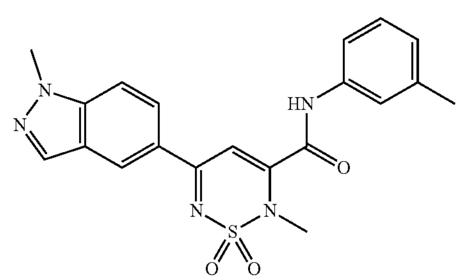 [SMILES: Cc1cccc(NC(=O)C2=CC(c3ccc4c(cnn4C)c3)=NS(=O)(=O)N2C)c1] | 410.1 | 64 |

TABLE 6-continued

| Example | Structure | LC-MS (ESI) m/z (M + H)+ | Starting intermediate |
|---|---|---|---|
| 23 | 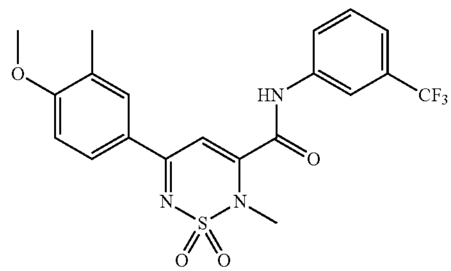 [SMILES: COc1ccc(C2=NS(=O)(=O)N(C)C(C(=O)Nc3cccc(C(F)(F)F)c3)=C2)cc1C] | 454.1 | 62 |
| 24 | 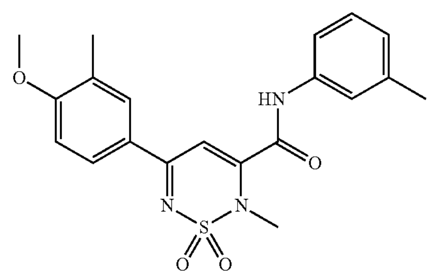 [SMILES: COc1ccc(C2=NS(=O)(=O)N(C)C(C(=O)Nc3cccc(C)c3)=C2)cc1C] | 400.2 | 62 |
| 25 | 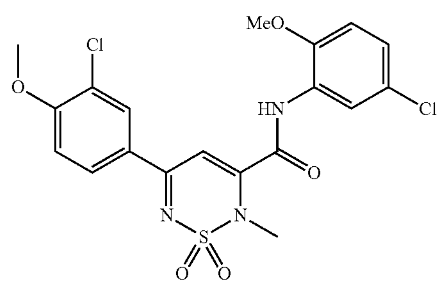 [SMILES: COc1ccc(C2=NS(=O)(=O)N(C)C(C(=O)Nc3cc(Cl)ccc3OC)=C2)cc1Cl] | 470.0 | 66 |
| 26 | 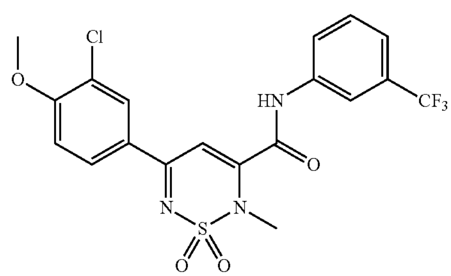 [SMILES: COc1ccc(C2=NS(=O)(=O)N(C)C(C(=O)Nc3cccc(C(F)(F)F)c3)=C2)cc1Cl] | 474.0 | 66 |
| 27 | 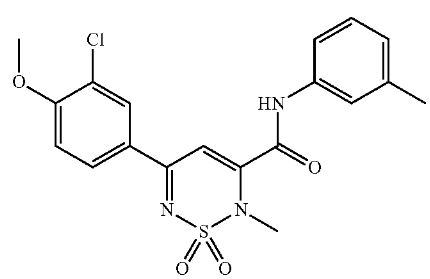 [SMILES: COc1ccc(C2=NS(=O)(=O)N(C)C(C(=O)Nc3cccc(C)c3)=C2)cc1Cl] | 420.0 | 66 |

TABLE 6-continued

| Example | Structure | LC-MS (ESI) m/z (M + H)+ | Starting intermediate |
|---|---|---|---|
| 28 | 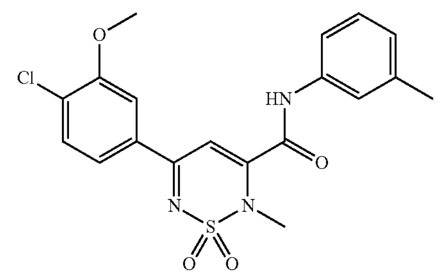 [SMILES: COc1cc(C2=NS(=O)(=O)N(C)C(C(=O)Nc3cccc(C)c3)=C2)ccc1Cl] | 420.2 | 67 |
| 29 | 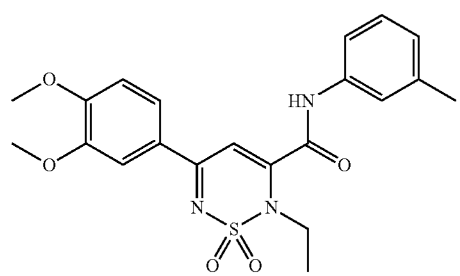 | 430.1 | 70 |
| 30 | 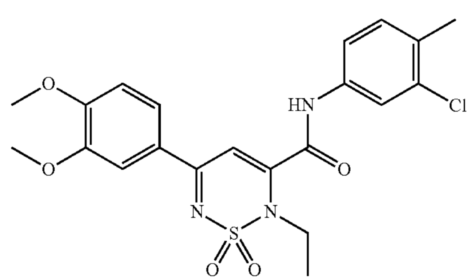 | 464.1 | 70 |
| 31 | 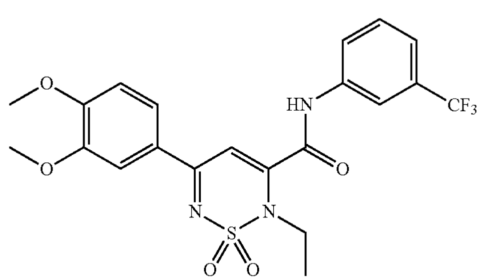 [SMILES: CCN1C(C(=O)Nc2cccc(C(F)(F)F)c2)=CC(c2ccc(OC)c(OC)c2)=NS1(=O)=O] | 484.2 | 70 |
| 32 | 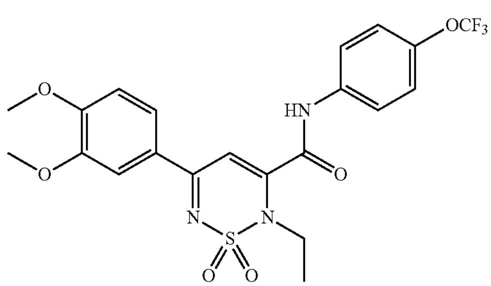 [SMILES: CCN1C(C(=O)Nc2ccc(OC(F)(F)F)cc2)=CC(c2ccc(OC)c(OC)c2)=NS1(=O)=O] | 500.2 | 70 |

TABLE 6-continued

| Example | Structure | LC-MS (ESI) m/z (M + H)+ | Starting intermediate |
|---|---|---|---|
| 33 | 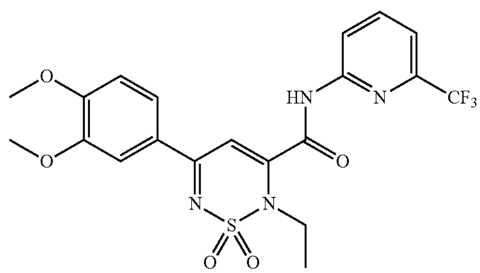 [SMILES: CCN1C(C(=O)Nc2cccc(C(F)(F)F)n2)=CC(c2ccc(OC)c(OC)c2)=NS1(=O)=O] | 485.2 | 70 |
| 34 | 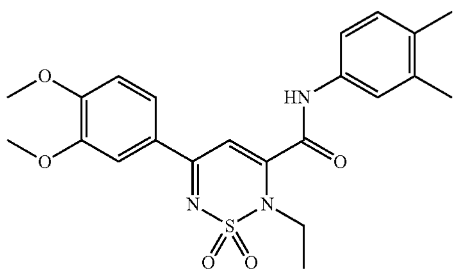 | 444.2 | 70 |
| 35 | 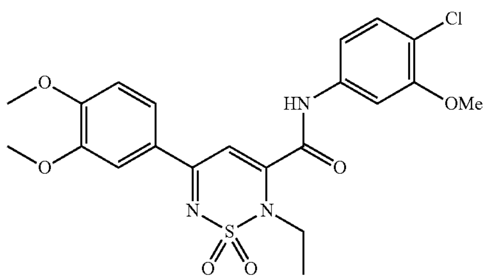 [SMILES: CCN1C(C(=O)Nc2ccc(Cl)c(OC)c2)=CC(c2ccc(OC)c(OC)c2)=NS1(=O)=O] | 480.2 | 70 |
| 36 | 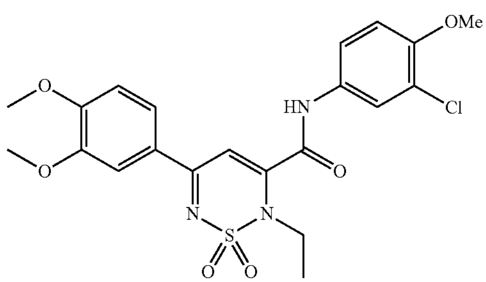 | 480.1 | 70 |
| 37 | 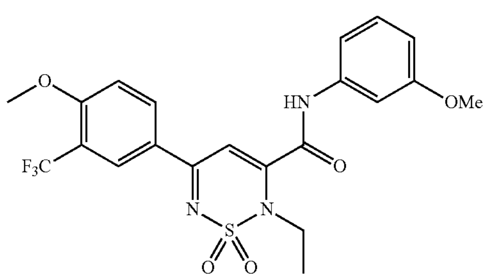 [SMILES: CCN1C(C(=O)Nc2cccc(OC)c2)=CC(c2ccc(OC)c(C(F)(F)F)c2)=NS1(=O)=O] | 484.2 | 71 |

TABLE 6-continued

| Example | Structure | LC-MS (ESI) m/z (M + H)+ | Starting intermediate |
|---|---|---|---|
| 38 | 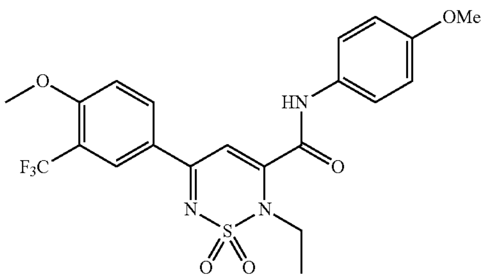 | 484.2 | 71 |
| 39 | 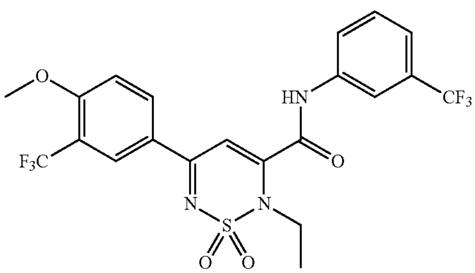 [SMILES: CCN1C(C(=O)Nc2cccc(C(F)(F)F)c2)=CC(c2ccc(OC)c(C(F)(F)F)c2)=NS1(=O)=O] | 522.2 | 71 |
| 40 | 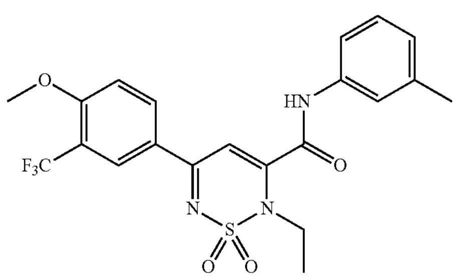 | 468.2 | 71 |
| 41 | 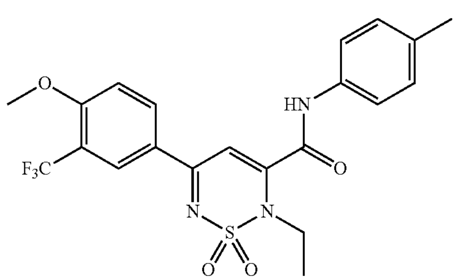 | 468.2 | 71 |
| 42 | 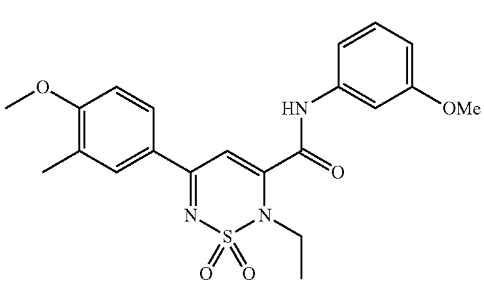 [SMILES: CCN1C(C(=O)Nc2cccc(OC)c2)=CC(c2ccc(OC)c(C)c2)=NS1(=O)=O] | 430.2 | 72 |

TABLE 6-continued

| Example | Structure | LC-MS (ESI) m/z (M + H)+ | Starting intermediate |
|---|---|---|---|
| 43 | 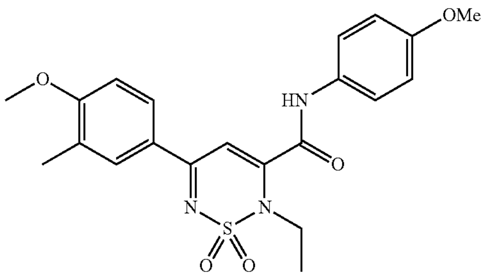 [SMILES: CCN1C(C(=O)Nc2ccc(OC)cc2)=CC(c2ccc(OC)c(C)c2)=NS1(=O)=O] | 430.2 | 72 |
| 44 | 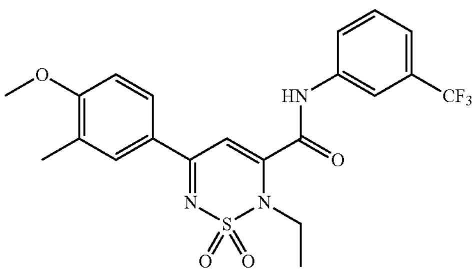 [SMILES: CCN1C(C(=O)Nc2cccc(C(F)(F)F)c2)=CC(c2ccc(OC)c(C)c2)=NS1(=O)=O] | 468.2 | 72 |
| 45 | 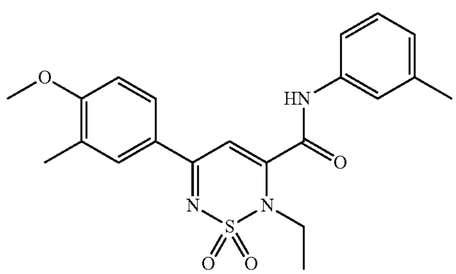 | 414.2 | 72 |
| 46 | 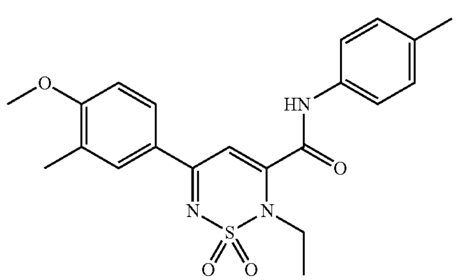 | 414.2 | 72 |
| 47 | 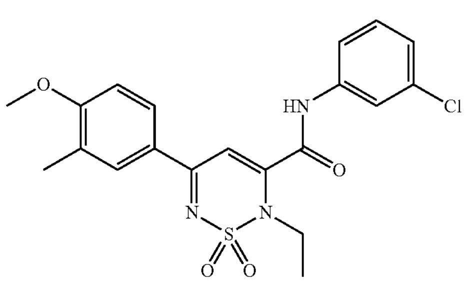 [SMILES: CCN1C(C(=O)Nc2cccc(Cl)c2)=CC(c2ccc(OC)c(C)c2)=NS1(=O)=O] | 434.2 | 72 |

TABLE 6-continued

| Example | Structure | LC-MS (ESI) m/z (M + H)+ | Starting intermediate |
|---|---|---|---|
| 48 | 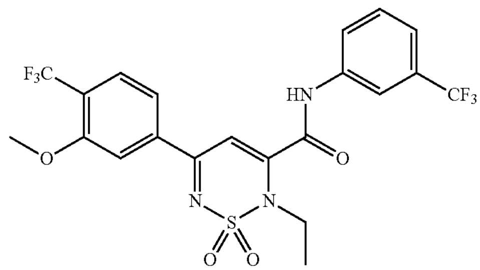 [SMILES: CCN1C(C(=O)Nc2cccc(C(F)(F)F)c2)=CC(c2ccc(C(F)(F)F)c(OC)c2)=NS1(=O)=O] | 522.1 | 73 |
| 49 | 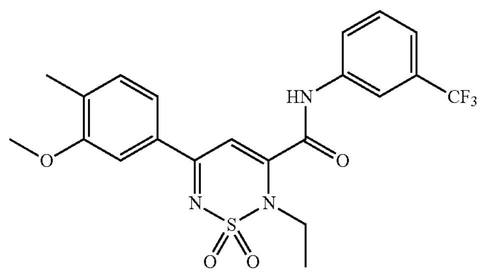 [SMILES: CCN1C(C(=O)Nc2cccc(C(F)(F)F)c2)=CC(c2ccc(C)c(OC)c2)=NS1(=O)=O] | 468.1 | 74 |
| 50 | 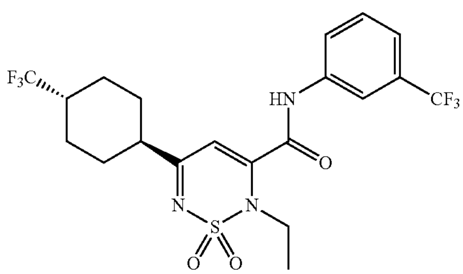 | 498.2 | 75 |
| 51 | 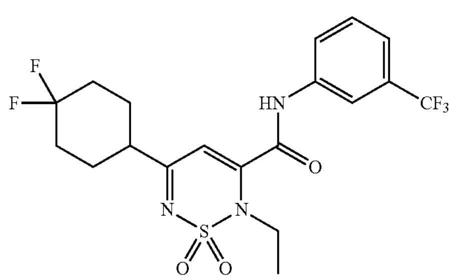 [SMILES: CCN1C(C(=O)Nc2cccc(C(F)(F)F)c2)=CC(C2CCC(F)(F)CC2)=NS1(=O)=O] | 466.1 | 79 |
| 52 | 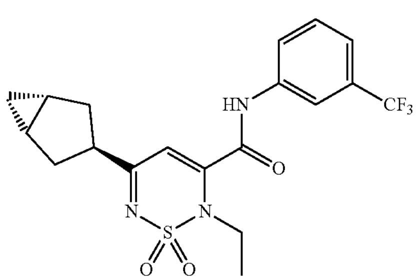 | 428.1 | 80 |

*Purchased library compound from ChemDiv (compound ID: E135-0764)

Example 53

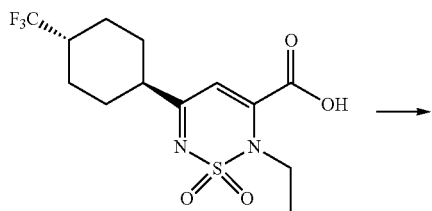

intermediate 75

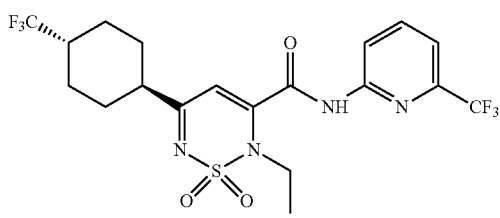

Example 53

2-ethyl-1,1-dioxo-5-[(1r,4r)-4-(trifluoromethyl)cyclohexyl]-N-[6-(trifluoromethyl)pyridin-2-yl]-2H-1λ⁶,2,6-thiadiazine-3-carboxamide In an inert atmosphere, to a solution of Intermediate 75 (2-ethyl-1,1-dioxo-5-[(1r,4r)-4-(trifluoromethyl)cyclohexyl]-2H-1λ⁶,2,6-thiadiazine-3-carboxylic acid; 500 mg, 1.41 mmol) and N,N-dimethylformamide (3 drops) in dichloromethane (20 mL), a solution of oxalyl chloride (0.24 mL, 2.82 mmol) in dichloromethane (10 mL) was added dropwise at room temperature. After 15 minutes of stirring at room temperature, the reaction mixture was evaporated to dryness, dichloromethane (20 mL) was added, and it was evaporated to dryness again. The residue (carbonyl chloride) was dissolved in tetrahydrofuran under an inert atmosphere, cooled to 0° C., tripotassium phosphate (375 mg, 1.76 mmol) and 2-amino-6-(trifluormethyl)pyridine (229 mg, 1.41 mmol) was added, and the mixture was stirred at room temperature for 3 hours.

The inorganic salts were filtered off, the filtrate was concentrated, and the residue was purified by column chromatography on silica gel with a terner mixture of cyclohexane, ethyl acetate and diisopropyl ether (40:10:1), as eluent. Yield: 440 mg (63%), m/z (M+H)⁺: 499.1.

The following examples in Table 7 were synthesized according to the procedure (via acid chloride coupling) described for Example 53.

TABLE 7

| Example | Structure | LC-MS (ESI) m/z (M + H)⁺ | Starting intermediate |
|---|---|---|---|
| 54 | 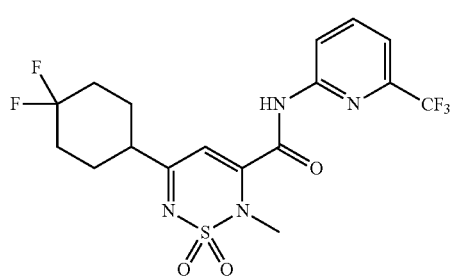 | 485.1 | 68 |
| 55 | 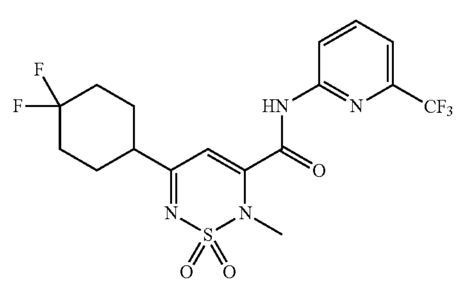 [SMILES: CN1C(C(=O)Nc2cccc(C(F)(F)F)n2)=CC(C2CCC(F)(F)CC2)=NS1(=O)=O] | 453.1 | 69 |

TABLE 7-continued

| Example | Structure | LC-MS (ESI) m/z (M + H)+ | Starting intermediate |
|---|---|---|---|
| 56 | 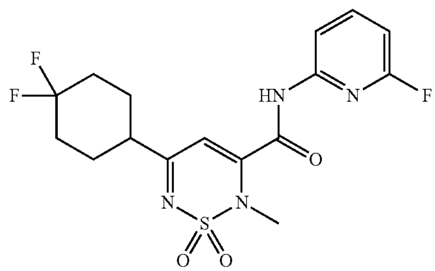 [SMILES: CN1C(C(=O)Nc2cccc(F)n2)=CC(C2CCC(F)(F)CC2)=NS1(=O)=O] | M + Na+ = 425.1 | 69 |
| 57 | 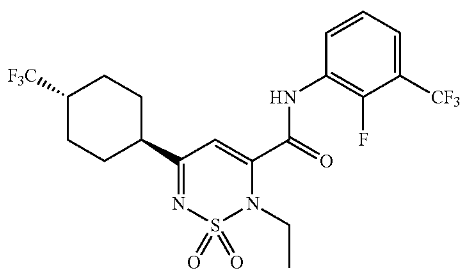 [SMILES: CCN1C(C(=O)Nc2cccc(C(F)(F)F)c2F)=CC([C@H]2CC[C@H](C(F)(F)F)CC2)=NS1(=O)=O] | 516.2 | 75 |
| 58 | 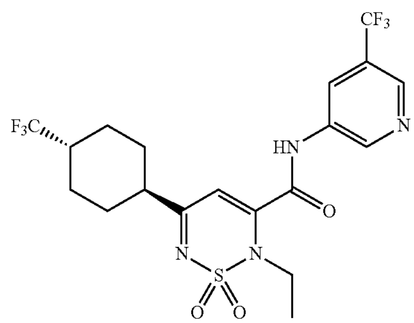 [SMILES: CCN1C(C(=O)Nc2cncc(C(F)(F)F)c2)=CC([C@H]2CC[C@H](C(F)(F)F)CC2)=NS1(=O)=O] | 499.1 | 75 |
| 59 | 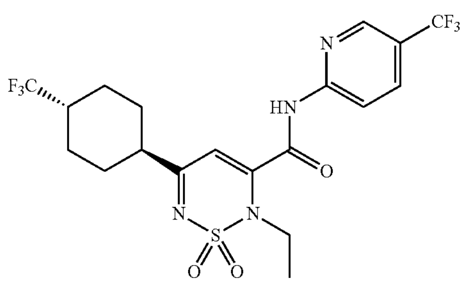 [SMILES: CCN1C(C(=O)Nc2ccc(C(F)(F)F)cn2)=CC([C@H]2CC[C@H](C(F)(F)F)CC2)=NS1(=O)=O] | 499.1 | 75 |
| 60* | 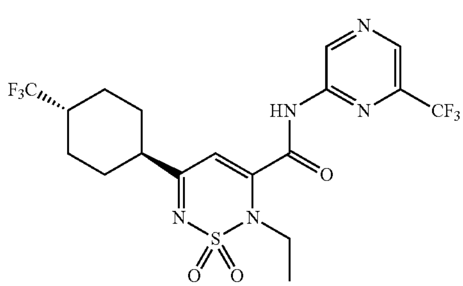 [SMILES: CCN1C(C(=O)Nc2cncc(C(F)(F)F)n2)=CC([C@H]2CC[C@H](C(F)(F)F)CC2)=NS1(=O)=O] | 500.1 | 75 |

TABLE 7-continued

| Example | Structure | LC-MS (ESI) m/z (M + H)+ | Starting intermediate |
|---|---|---|---|
| 61 | 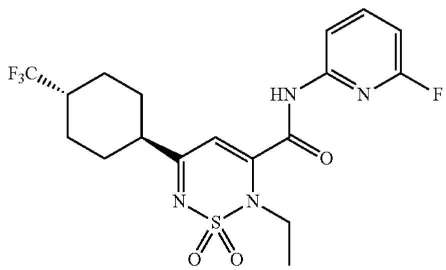 [SMILES: CCN1C(C(=O)Nc2cccc(F)n2)=CC([C@H]2CC[C@H](C(F)(F)F)CC2)=NS1(=O)=O] | 449.2 | 75 |
| 62 | 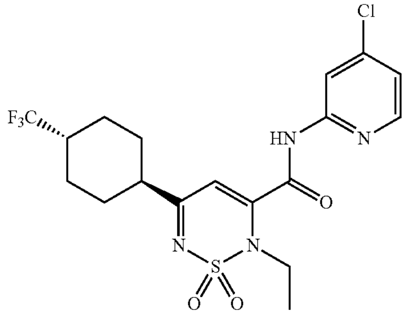 [SMILES: CCN1C(C(=O)Nc2cc(Cl)ccn2)=CC([C@H]2CC[C@H](C(F)(F)F)CC2)=NS1(=O)=O] | 465.1 | 75 |
| 63* | 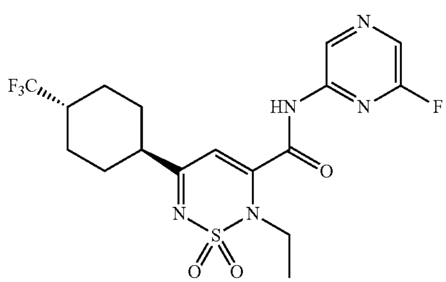 [SMILES: CCN1C(C(=O)Nc2cncc(F)n2)=CC([C@H]2CC[C@H](C(F)(F)F)CC2)=NS1(=O)=O] | 450.0 | 75 |
| 64* | 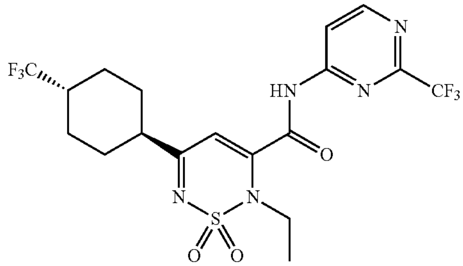 [SMILES: CCN1C(C(=O)Nc2ccnc(C(F)(F)F)n2)=CC([C@H]2CC[C@H](C(F)(F)F)CC2)=NS1(=O)=O] | 500.1 | 75 |
| 65 | 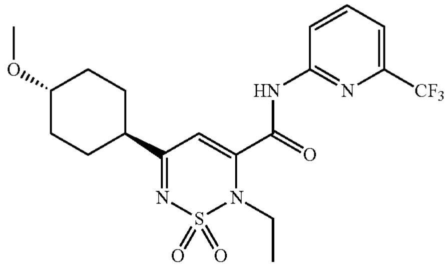 [SMILES: CCN1C(C(=O)Nc2cccc(C(F)(F)F)n2)=CC([C@H]2CC[C@H](OC)CC2)=NS1(=O)=O] | 461.2 | 76 |

TABLE 7-continued

| Example | Structure | LC-MS (ESI) m/z (M + H)+ | Starting intermediate |
|---|---|---|---|
| 66 | 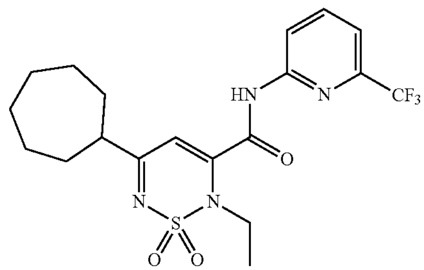 [SMILES: CCN1C(C(=O)Nc2cccc(C(F)(F)F)n2)=CC(C2CCCCCC2)=NS1(=O)=O] | 445.2 | 77 |
| 67 | 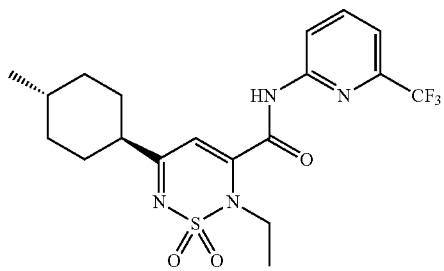 [SMILES: CCN1C(C(=O)Nc2cccc(C(F)(F)F)n2)=CC([C@H]2CC[C@H](C)CC2)=NS1(=O)=O] | 445.2 | 78 |
| 68 | 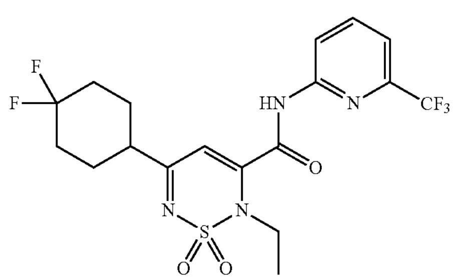 [SMILES: CCN1C(C(=O)Nc2cccc(C(F)(F)F)n2)=CC(C2CCC(F)(F)CC2)=NS1(=O)=O] | 467.1 | 79 |
| 69* | 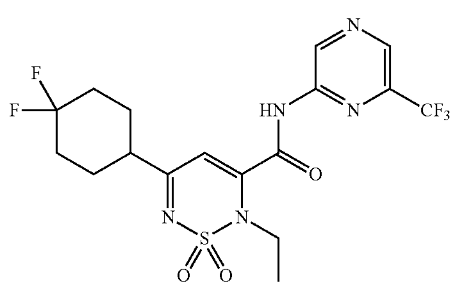 [SMILES: CCN1C(C(=O)Nc2cncc(C(F)(F)F)n2)=CC(C2CCC(F)(F)CC2)=NS1(=O)=O] | 468.2 | 79 |
| 70 | 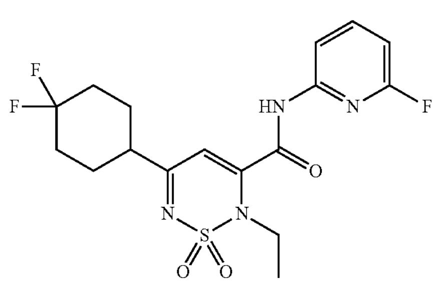 [SMILES: CCN1C(C(=O)Nc2cccc(F)n2)=CC(C2CCC(F)(F)CC2)=NS1(=O)=O] | 417.1 | 79 |

TABLE 7-continued

| Example | Structure | LC-MS (ESI) m/z (M + H)+ | Starting intermediate |
| --- | --- | --- | --- |
| 71 | 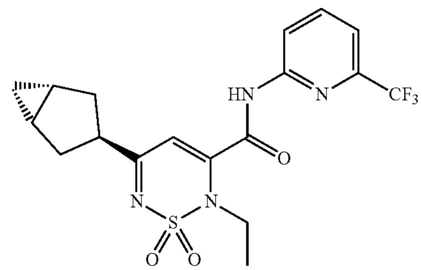 | 429.1 | 80 |
| 72 | 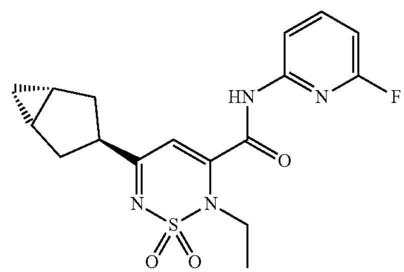 | 379.2 | 80 |
| 73 | 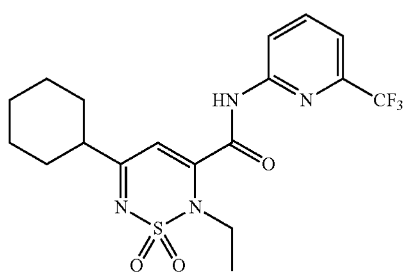 [SMILES: CCN1C(C(=O)Nc2cccc(C(F)(F)F)n2)=CC(C2CCCCC2)=NS1(=O)=O] | 431.1 | 81 |
| 74 | 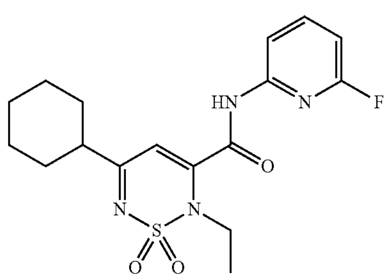 [SMILES: CCN1C(C(=O)Nc2cccc(F)n2)=CC(C2CCCCC2)=NS1(=O)=O] | 381.1 | 81 |
| 75 | 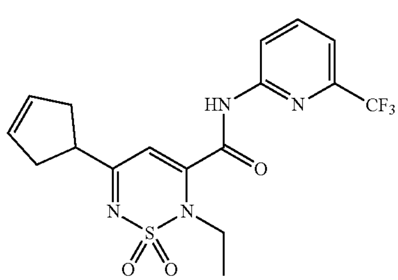 [SMILES: CCN1C(C(=O)Nc2cccc(C(F)(F)F)n2)=CC(C2CC=CC2)=NS1(=O)=O] | 415.1 | 82 |

TABLE 7-continued

| Example | Structure | LC-MS (ESI) m/z (M + H)+ | Starting intermediate |
|---|---|---|---|
| 76* | 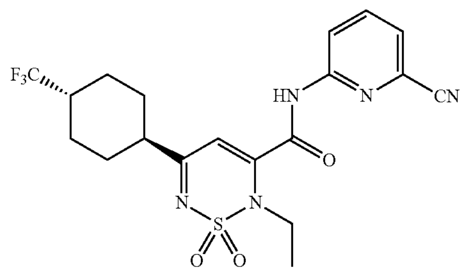 [SMILES: CCN1C(C(=O)Nc2cccc(C#N)n2)=CC([C@H]2CC[C@H](C(F)(F)F)CC2)=NS1(=O)=O] | 456.1 | 75 |
| 77 | 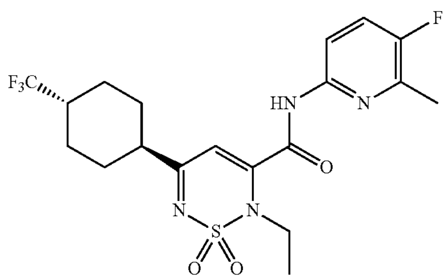 [SMILES: CCN1C(C(=O)Nc2ccc(F)c(C)n2)=CC([C@H]2CC[C@H](C(F)(F)F)CC2)=NS1(=O)=O] | 463.1 | 75 |
| 78 | 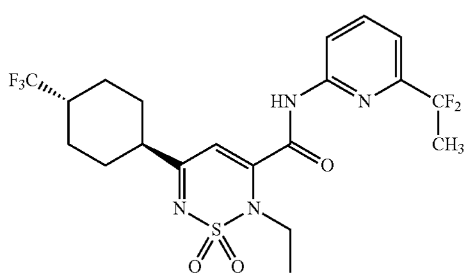 [SMILES: CCN1C(C(=O)Nc2cccc(C(C)(F)F)n2)=CC([C@H]2CC[C@H](C(F)(F)F)CC2)=NS1(=O)=O] | 495.1 | 75 |
| 79* | 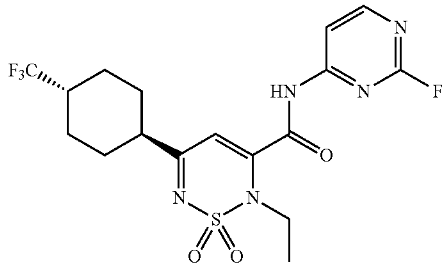 [SMILES: CCN1C(C(=O)Nc2ccnc(F)n2)=CC([C@H]2CC[C@H](C(F)(F)F)CC2)=NS1(=O)=O] | 450.1 | 75 |
| 80 | 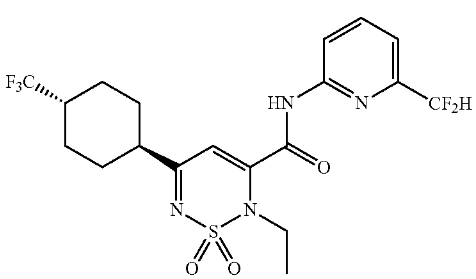 [SMILES: CCN1C(C(=O)Nc2cccc(C(F)F)n2)=CC([C@H]2CC[C@H](C(F)(F)F)CC2)=NS1(=O)=O] | 481.3 | 75 |

TABLE 7-continued

| Example | Structure | LC-MS (ESI) m/z (M + H)+ | Starting intermediate |
| --- | --- | --- | --- |
| 81 | 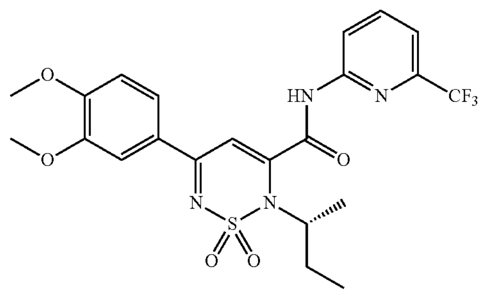 [SMILES: CC[C@@H](C)N1C(C(=O)Nc2cccc(C(F)(F)F)n2)=CC(c2ccc(OC)c(OC)c2)=NS1(=O)=O] | 513.1 | 84 |
| 82 | 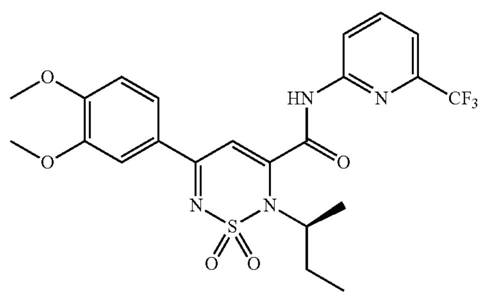 [SMILES: CC[C@H](C)N1C(C(=O)Nc2cccc(C(F)(F)F)n2)=CC(c2ccc(OC)c(OC)c2)=NS1(=O)=O] | 513.1 | 83 |
| 83 | 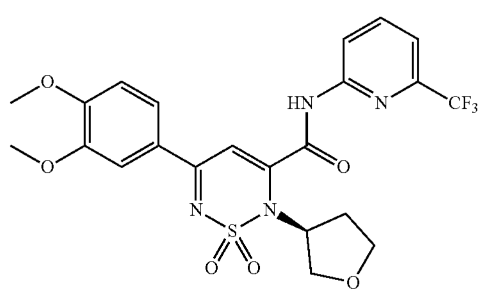 [SMILES: COc1ccc(C2=NS(=O)(=O)N([C@H]3CCOC3)C(C(=O)Nc3cccc(C(F)(F)F)n3)=C2)cc1OC] | 527.1 | 85 |
| 84 | 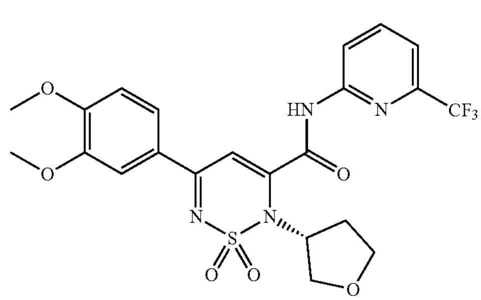 [SMILES: COc1ccc(C2=NS(=O)(=O)N([C@@H]3CCOC3)C(C(=O)Nc3cccc(C(F)(F)F)n3)=C2)cc1OC] | 527.1 | 86 |

*Triethylamine was applied (replacement of K₃PO₄) in dichloroethane, at 75° C.

Example 85

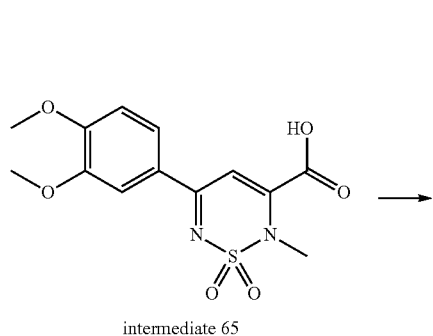

intermediate 65

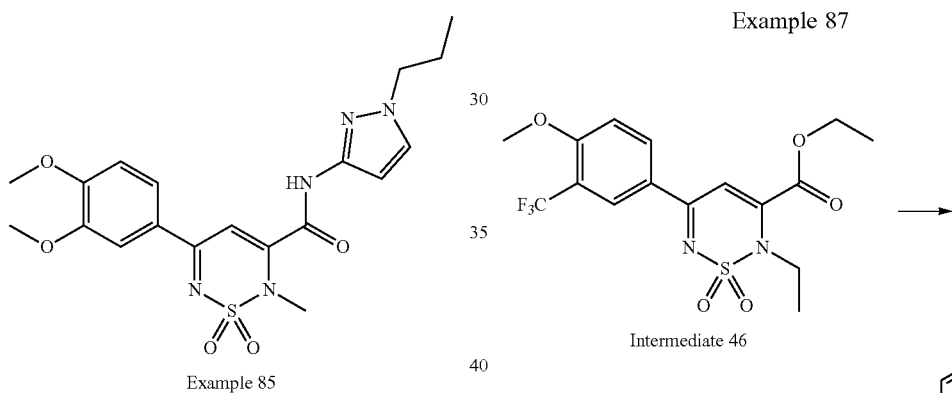

Example 85

5-(3,4-dimethoxyphenyl)-2-methyl-1,1-dioxo-N-(1-propyl-1H-pyrazol-3-yl)-2H-1λ⁶,2,6-thiadiazine-3-carboxamide Under an inert atmosphere, to a mixture of Intermediate 65 (5-(3,4-dimethoxyphenyl)-2-methyl-1,1-dioxo-2H-1λ⁶, 2,6-thiadiazine-3-carboxylic acid: 210 mg, 0.64 mmol) and N-(3-dimethylaminopropyl)-N'-ethylcarbodiimide hydrochloride (EDC, 248 mg, 1.29 mmol) in N,N-dimethylformamide (9 mL), 1-propyl-1H-pyrazol-3-amine (99 mg, 0.79 mmol) and 4-(dimethylamino)pyridine (209 mg, 1.71 mmol) was added, and the mixture was stirred at room temperature for 4 days. Another portion of 1-propyl-1H-pyrazol-3-amine (85 mg, 0.68 mmol) in N,N-dimethylformamide (2 mL) was added, and the mixture was stirred further for 2 days. 10% HCl solution was added, and the mixture was extracted with ethyl acetate. The combined organic layer was washed with water, dried over Na₂SO₄, and evaporated to dryness. The residue was purified by column chromatography on silica gel with a mixture of ethyl acetate and cyclohexane (1:1), as eluent. Yield: 5 mg (2%) yellow crystals, m/z (M+H)⁺: 434.1.

Example 86

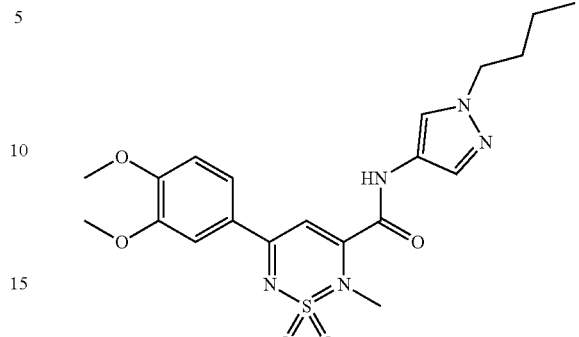

N-(1-butyl-1H-pyrazol-4-yl)-5-(3,4-dimethoxyphenyl)-2-methyl-1,1-dioxo-2H-1λ⁶,2,6-thiadiazine-3-carboxamide (Purchased Library Compound, Chemdiv (Catalog no.: E135-0831))

Step 6

Example 87

Intermediate 46

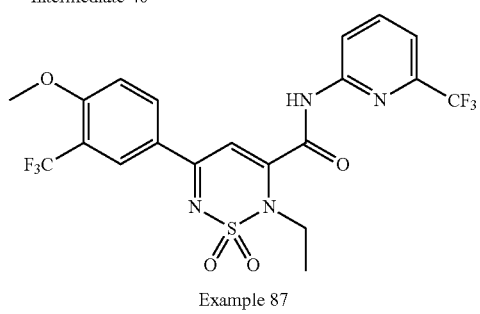

Example 87

2-ethyl-5-[4-methoxy-3-(trifluoromethyl)phenyl]-1,1-dioxo-N-[6-(trifluoromethyl)pyridin-2-yl]-2H-1λ⁶,2,6-thiadiazine-3-carboxamide To a solution of 2-amino-6-(trifluoromethyl)pyridine (389 mg, 2.4 mmol) in 1,2-dichloroethane (3 mL), a solution of triethyl aluminium (1.9M, 1.25 mL) in toluene was added dropwise at 20-25° C. during slight cooling under argon atmosphere, and the solution was stirred at room temperature for another hour. A solution of Intermediate 46 (ethyl 2-ethyl-5-[4-methoxy-3-(trifluoromethyl)phenyl]-1,1-dioxo-2H-1λ⁶,2,6-thiadiazine-3-carboxylate, 203 mg, 0.5 mmol) in 1,2-dichloroethane (3 mL) was added, and the mixture was heated at 65° C. overnight.

After cooling to room temperature, 1 M HCl solution (10 mL) was added dropwise, and the mixture was stirred at 35-40° C. for an hour. The phases were separated, and the aqueous phase was extracted with dichloromethane. The combined organic layer was washed with water, dried over Na₂SO₄, filtered, concentrated under reduced pressure and the residue was purified by flash column chromatography on silica gel, with a gradient of a mixture of diisopropyl ether and dichloromethane. Yield: 206 mg (79%), m/z (M+H)⁺: 523.1.

Example 88 was synthesized from Intermediate 50 according to the procedure described for Example 82.

Example 88

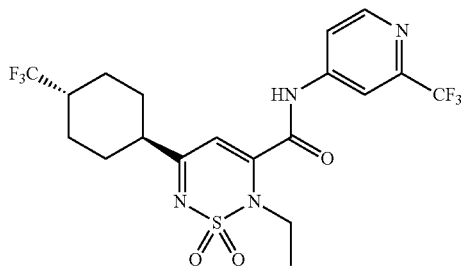 [SMILES: CCN1C(C(=O)Nc2ccnc(C(F)(F)F)c2)=CC([C@H]2CC[C@H](C(F)(F)F)CC2)=NS1(=O)=O]

2-ethyl-N-(2-methylpyridin-4-yl)-1,1-dioxo-5-[(1r,4r)-4-methylcyclohexyl]-2H-1λ⁶,2,6-thiadiazine-3-carboxamide, m/z (M+H)⁺: 499.1.

Step 7

Intermediate 87

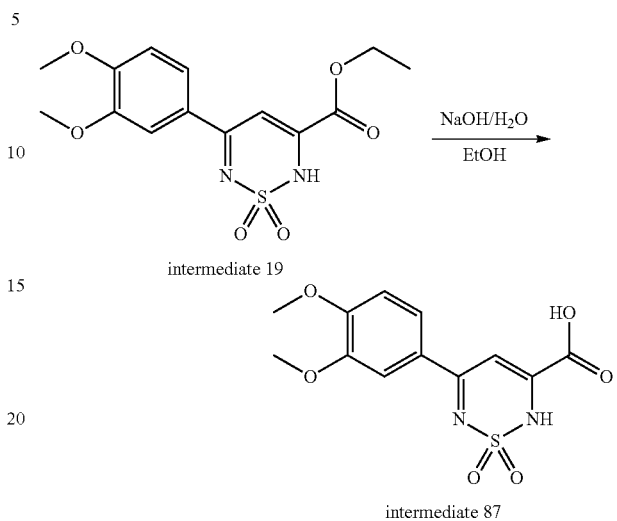

intermediate 19 intermediate 87

5-(3,4-dimethoxyphenyl)-1,1-dioxo-2H-1λ⁶,2,6-thiadiazin-3-carboxylic Acid

To a suspension of Intermediate 19 (ethyl 5-(3,4-dimethoxyphenyl)-1,1-dioxo-2H-1λ⁶,2,6-thiadiazine-3-carboxylate, 8.00 g, 23.5 mmol) in ethanol (400 mL), an aqueous 5 M NaOH solution (19 mL) was added, and the mixture was stirred at room temperature for 2.5 hours. The pH of the mixture was adjusted to 5-6 by the addition of 3 M HCl solution during cooling with ice. The solvent was removed in vacuo, and dried at 40° C. in a drying oven until permanent mass had been achieved. The obtained product (containing significant amount of NaCl) was used in the next step without further purification (m/z (M+H)⁺: 313.1).

The following intermediates in Table 8 were synthesized according to the procedure described for Intermediate 87.

TABLE 8

| Intermediate | Structure | Starting intermediate |
|---|---|---|
| 88 | 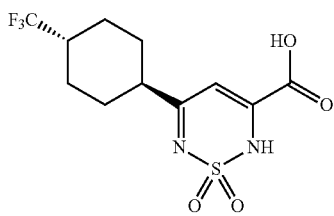 [SMILES: O=C(O)C1=CC([C@H]2CC[C@H](C(F)(F)F)CC2)=NS(=O)(=O)N1] | 29 |

TABLE 8-continued

| Intermediate | Structure | Starting intermediate |
|---|---|---|
| 89 | (4,4-difluorocyclohexyl-substituted thiadiazine carboxylic acid 1,1-dioxide) | 30 |
| 90* | (2-fluoro-4,5-dimethoxyphenyl-substituted thiadiazine carboxylic acid 1,1-dioxide) | 26 |
| 91 | (4-methoxy-3-trifluoromethylphenyl-substituted thiadiazine carboxylic acid 1,1-dioxide) | 24 |
| 92 | (4-methoxy-3-methylphenyl-substituted thiadiazine carboxylic acid 1,1-dioxide) | 22 |
| 93* | (3-chloro-4-methoxyphenyl-substituted thiadiazine carboxylic acid 1,1-dioxide) | 20 |

*2M conc. aqueous NaOH solution, 2-3 mol equivalents

Step 8

Intermediate 94

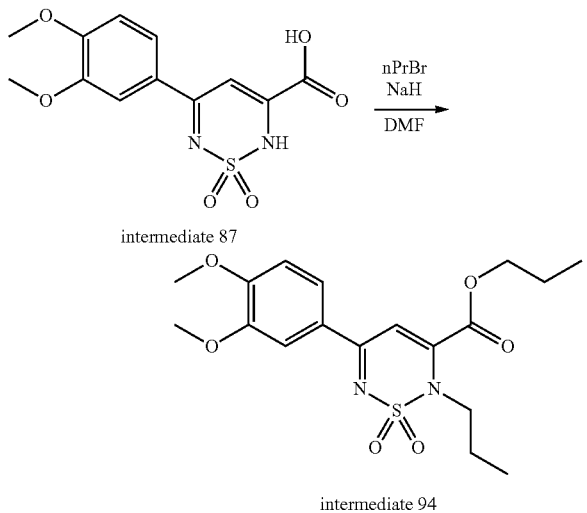

Propyl 5-(3,4-dimethoxyphenyl)-1,1-dioxo-2-propyl-2H-1λ⁶,2,6-thiadiazine-3-carboxylate To a suspension of Intermediate 87 (5-(3,4-dimethoxyphenyl)-1,1-dioxo-2H-1λ⁶,2,6-thiadiazine-3-carboxylic acid; 11.8 mmol) in N,N-dimethylformamide (80 mL), sodium hydride (1.88 g, 47.0 mmol, 60% in mineral oil) was added under an inert atmosphere. 1-bromopropane (21.3 mL, 235 mmol) was added, and the mixture was stirred at 80° C. overnight. The reaction mixture was allowed to cool to room temperature, water (20 mL) and 10% HCl solution (20 mL) was added, and it was extracted with ethyl acetate. The combined organic layer was washed with water, 1 M $Na_2S_2O_3$ solution and brine, dried over $Na_2SO_4$, filtered, and evaporated to dryness. The residue was purified by column chromatography on silica gel, using a mixture of dichloromethane and diisopropyl ether (60:1) as eluent. Yield: 3.14 g (67%) yellow crystals.

The following intermediates in Table 9 were synthesized according to the procedure described for Intermediate 94.

TABLE 9

| Intermediate | Structure | Starting intermediate |
|---|---|---|
| 95* | (structure) | 88 |
| 96* | (structure) | 89 |
| 97 | (structure) | 87 |

TABLE 9-continued

| Intermediate | Structure | Starting intermediate |
|---|---|---|
| 98 | 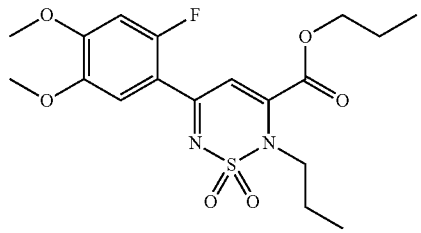 [SMILES: CCCOC(=O)C1=CC(c2cc(OC)c(OC)cc2F)=NS(=O)(=O)N1CCC] | 90 |
| 99 | 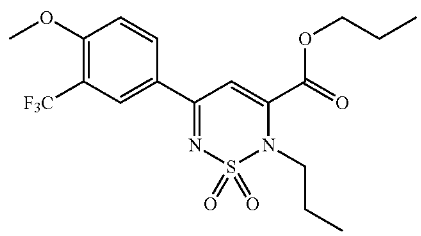 [SMILES: CCCOC(=O)C1=CC(c2ccc(OC)c(C(F)(F)F)c2)=NS(=O)(=O)N1CCC] | 91 |
| 100 | 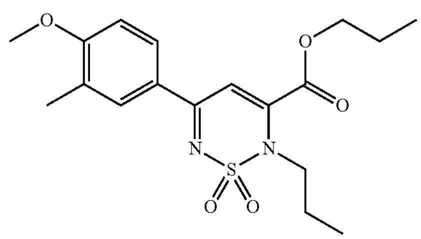 [SMILES: CCCOC(=O)C1=CC(c2ccc(OC)c(C)c2)=NS(=O)(=O)N1CCC] | 92 |
| 101 | 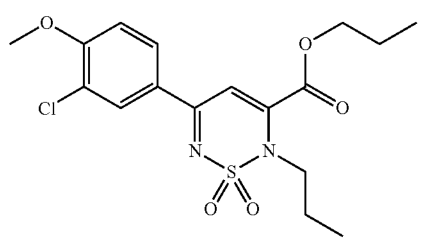 [SMILES: CCCOC(=O)C1=CC(c2ccc(OC)c(Cl)c2)=NS(=O)(=O)N1CCC] | 93 |
| 102 | 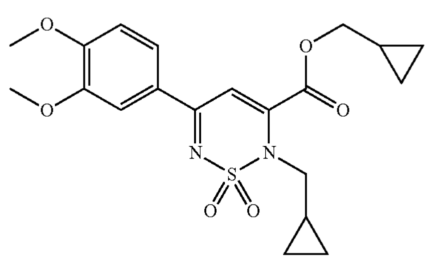 [SMILES: COc1ccc(C2=NS(=O)(=O)N(CC3CC3)C(C(=O)OCC3CC3)=C2)cc1OC] | 87 |
| 103 | 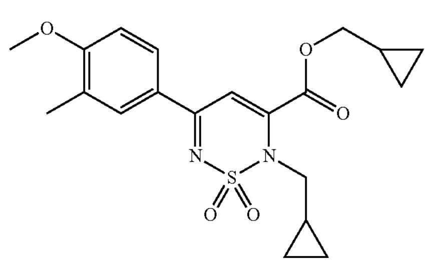 [SMILES: COc1ccc(C2=NS(=O)(=O)N(CC3CC3)C(C(=O)OCC3CC3)=C2)cc1C] | 92 |

TABLE 9-continued
| Intermediate | Structure | Starting intermediate |
|---|---|---|
| 104 | 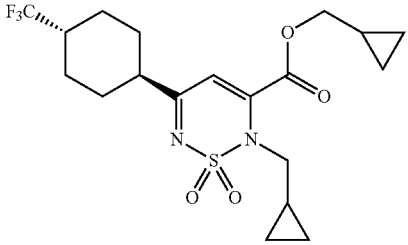 [SMILES: O=C(OCC1CC1)C1=CC([C@H]2CC[C@H](C(F)(F)F)CC2)=NS(=O)(=O)N1CC1CC1] | 88 |
| 105 | 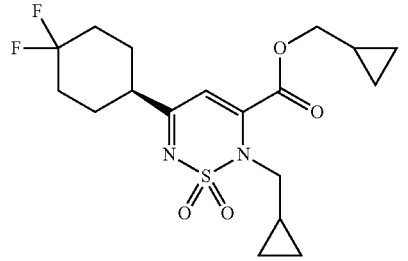 | 89 |
| 106 | 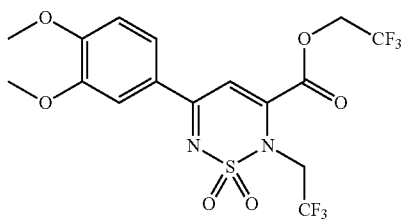 [SMILES: COc1ccc(C2=NS(=O)(=O)N(CC(F)(F)F)C(C(=O)OCC(F)(F)F)=C2)cc1OC] | 87 |
| 107 | 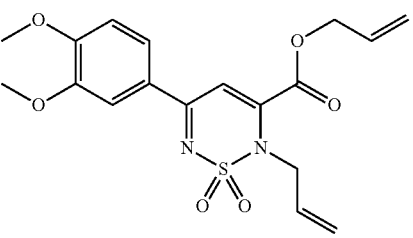 [SMILES: C=CCOC(=O)C1=CC(c2ccc(OC)c(OC)c2)=NS(=O)(=O)N1CC=C] | 87 |
| 108 | 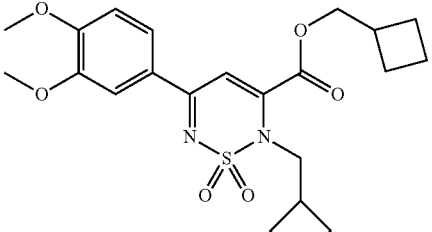 | 87 |
| 109 | 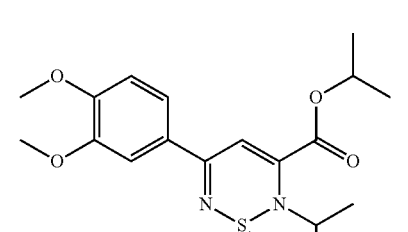 | 87 |

TABLE 9-continued

| Intermediate | Structure | Starting intermediate |
|---|---|---|
| 110 | [structure: F3C-cyclohexyl-substituted thiadiazine with isopropyl ester and N-isopropyl] | 88 |
| 111 | [structure: 4,4-difluorocyclohexyl-substituted thiadiazine with isopropyl ester and N-isopropyl] | 89 |

*DIPEA was applied as the replacement of NaH

Step 9

The following intermediates in Table 10 were synthesized according to the procedure described for Intermediate 62, except that 1.2-1.5 mol equivalent, 1-2 M NaOH or LiOH solution was used.

TABLE 10

| Intermediate | Structure | Starting intermediate |
|---|---|---|
| 112 | [structure: 3,4-dimethoxyphenyl-substituted thiadiazine carboxylic acid with N-isopropyl] | 109 |
| 113 | [structure: F3C-cyclohexyl-substituted thiadiazine carboxylic acid with N-isopropyl] | 110 |
| 114 | [structure: 4,4-difluorocyclohexyl-substituted thiadiazine carboxylic acid with N-isopropyl] | 111 |

TABLE 10-continued

| Intermediate | Structure | Starting intermediate |
|---|---|---|
| 115 | [structure: F3C-cyclohexyl-substituted thiadiazine carboxylic acid with N-methoxyethyl] | 95 |
| 116 | [structure: 4,4-difluorocyclohexyl-substituted thiadiazine carboxylic acid with N-methoxyethyl] | 96 |
| 117 | [structure: 3,4-dimethoxyphenyl-substituted thiadiazine carboxylic acid with N-butyl] | 97 |

TABLE 10-continued

| Intermediate | Structure | Starting intermediate |
|---|---|---|
| 118* | 4-(3,4-dimethoxyphenyl)-2-propyl-2H-1,2,6-thiadiazine-3-carboxylic acid 1,1-dioxide | 94 |
| 119** | 4-(4-methoxy-3-(trifluoromethyl)phenyl)-2-propyl-2H-1,2,6-thiadiazine-3-carboxylic acid 1,1-dioxide | 99 |
| 120 | 2-(cyclopropylmethyl)-4-(3,4-dimethoxyphenyl)-2H-1,2,6-thiadiazine-3-carboxylic acid 1,1-dioxide | 102 |
| 121 | 2-(cyclopropylmethyl)-4-(trans-4-(trifluoromethyl)cyclohexyl)-2H-1,2,6-thiadiazine-3-carboxylic acid 1,1-dioxide | 104 |
| 122 | 2-(cyclopropylmethyl)-4-(4,4-difluorocyclohexyl)-2H-1,2,6-thiadiazine-3-carboxylic acid 1,1-dioxide | 105 |
| 123* | 4-(3,4-dimethoxyphenyl)-2-(2,2,2-trifluoroethyl)-2H-1,2,6-thiadiazine-3-carboxylic acid 1,1-dioxide | 106 |
| 124* | 2-allyl-4-(3,4-dimethoxyphenyl)-2H-1,2,6-thiadiazine-3-carboxylic acid 1,1-dioxide | 107 |
| 125 | 2-(cyclobutylmethyl)-4-(3,4-dimethoxyphenyl)-2H-1,2,6-thiadiazine-3-carboxylic acid 1,1-dioxide | 108 |

LiOH, 1M conc., 1.3-2 mol equivalents, in THF
**NaOH, 5M conc., 4 mol equivalents Step 5

The following examples in Table 11 were synthesized according to the procedure (via ester amidation in the presence of AlEt$_3$) described for Example 87.

TABLE 11

| Example | Structure | LC-MS (ESI) m/z (M + H)+ | Starting intermediate |
|---|---|---|---|
| 89 | 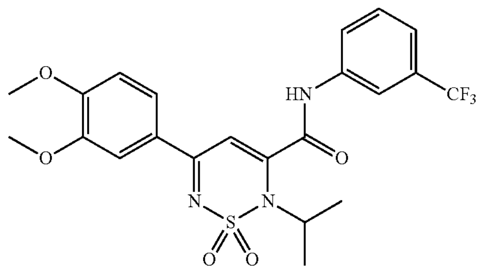 [SMILES: COc1ccc(C2=NS(=O)(=O)N(C(C)C)C(C(=O)Nc3cccc(C(F)(F)F)c3)=C2)cc1OC] | 498.1 | 109 |
| 90* | 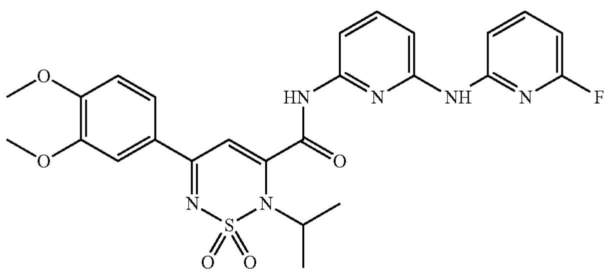 [SMILES: COc1ccc(C2=NS(=O)(=O)N(C(C)C)C(C(=O)Nc3cccc(Nc4cccc(F)n4)n3)=C2)cc1OC] | 541.2 | 109 |
| 91* | 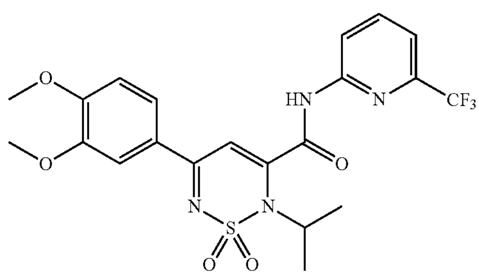 [SMILES: COc1ccc(C2=NS(=O)(=O)N(C(C)C)C(C(=O)Nc3cccc(C(F)(F)F)n3)=C2)cc1OC] | 499.1 | 109 |
| 92 | 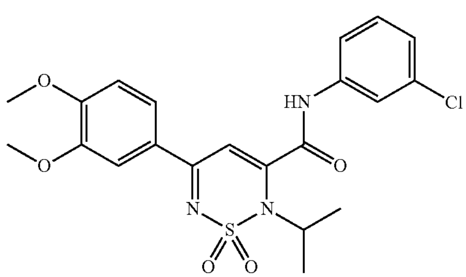 [SMILES: COc1ccc(C2=NS(=O)(=O)N(C(C)C)C(C(=O)Nc3cccc(Cl)c3)=C2)cc1OC] | 464.1 | 109 |
| 93* | 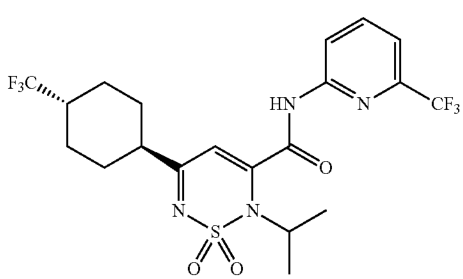 [SMILES: CC(C)N1C(C(=O)Nc2cccc(C(F)(F)F)n2)=CC([C@H]2CC[C@H](C(F)(F)F)CC2)=NS1(=O)=O] | 513.1 | 110 |

TABLE 11-continued

| Example | Structure | LC-MS (ESI) m/z (M + H)+ | Starting intermediate |
|---------|-----------|--------------------------|----------------------|
| 94 | 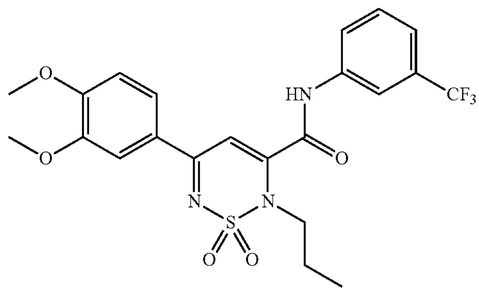 [SMILES: CCCN1C(C(=O)Nc2cccc(C(F)(F)F)c2)=CC(c2ccc(OC)c(OC)c2)=NS1(=O)=O] | 498.2 | 94 |
| 95 | 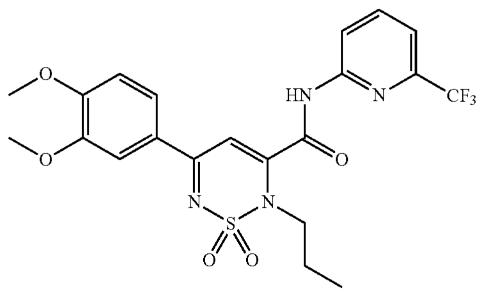 [SMILES: CCCN1C(C(=O)Nc2cccc(C(F)(F)F)n2)=CC(c2ccc(OC)c(OC)c2)=NS1(=O)=O] | 499.1 | 94 |
| 96 | 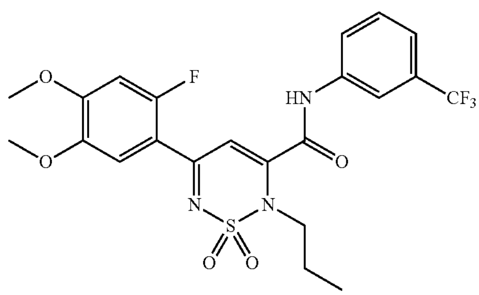 [SMILES: CCCN1C(C(=O)Nc2cccc(C(F)(F)F)c2)=CC(c2cc(OC)c(OC)cc2F)=NS1(=O)=O] | 516.1 | 98 |
| 97 | 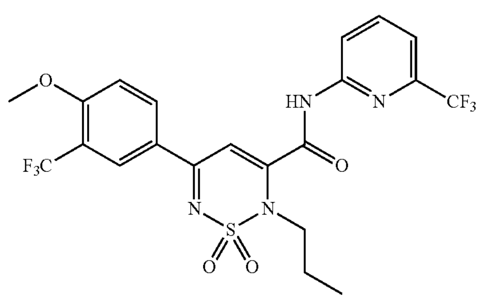 | 537.1 | 99 |
| 98 | 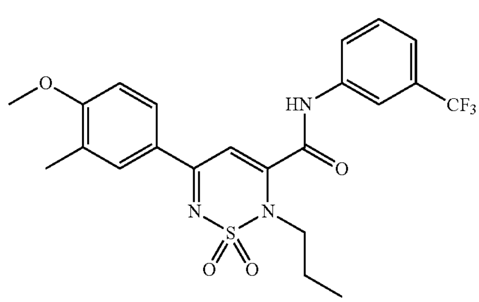 [SMILES: CCCN1C(C(=O)Nc2cccc(C(F)(F)F)c2)=CC(c2ccc(OC)c(C)c2)=NS1(=O)=O] | 482.1 | 100 |

TABLE 11-continued

| Example | Structure | LC-MS (ESI) m/z (M + H)+ | Starting intermediate |
|---|---|---|---|
| 99 | 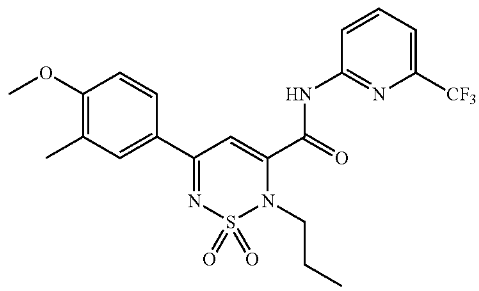 [SMILES: CCCN1C(C(=O)Nc2cccc(C(F)(F)F)n2)=CC(c2ccc(OC)c(C)c2)=NS1(=O)=O] | 483.1 | 100 |
| 100 | 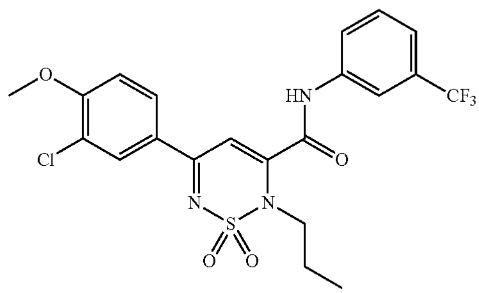 [SMILES: CCCN1C(C(=O)Nc2cccc(C(F)(F)F)c2)=CC(c2ccc(OC)c(Cl)c2)=NS1(=O)=O] | 502.1 | 101 |
| 101 | 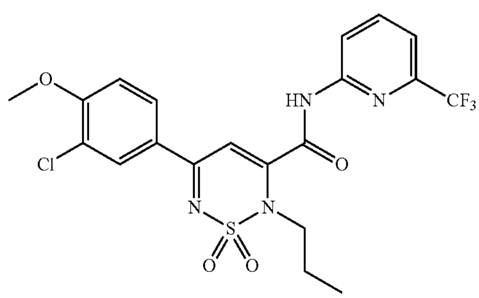 | 503.1 | 101 |
| 102* | 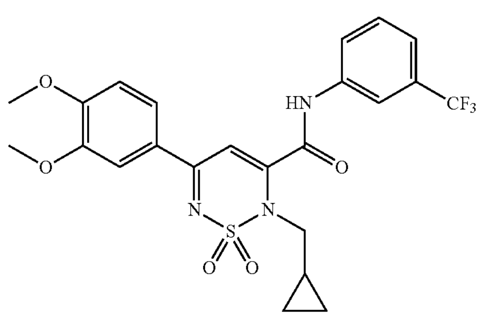 [SMILES: COc1ccc(C2=NS(=O)(=O)N(CC3CC3)C(C(=O)Nc3cccc(C(F)(F)F)c3)=C2)cc1OC] | 510.2 | 102 |
| 103 | 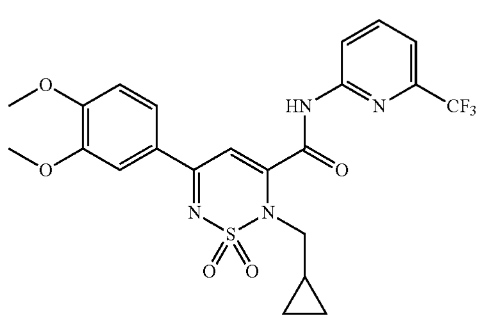 [SMILES: COc1ccc(C2=NS(=O)(=O)N(CC3CC3)C(C(=O)Nc3cccc(C(F)(F)F)n3)=C2)cc1OC] | 511.1 | 102 |

TABLE 11-continued

| Example | Structure | LC-MS (ESI) m/z (M + H)+ | Starting intermediate |
|---|---|---|---|
| 104 | 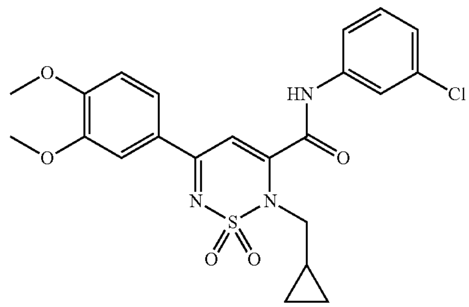 [SMILES: COc1ccc(C2=NS(=O)(=O)N(CC3CC3)C(C(=O)Nc3cccc(Cl)c3)=C2)cc1OC] | 476.1 | 102 |
| 105 | 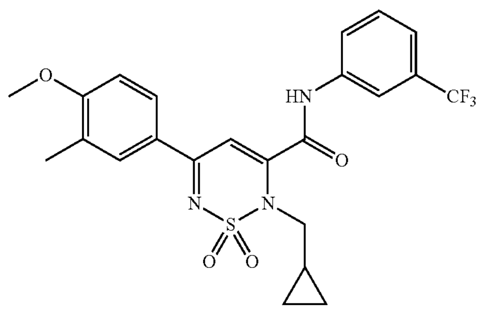 [SMILES: COc1ccc(C2=NS(=O)(=O)N(CC3CC3)C(C(=O)Nc3cccc(C(F)(F)F)c3)=C2)cc1C] | 494.1 | 103 |
| 106* | 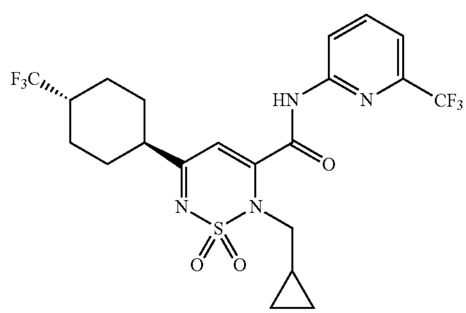 [SMILES: O=C(Nc1cccc(C(F)(F)F)n1)C1=CC([C@H]2CC[C@H](C(F)(F)F)CC2)=NS(=O)(=O)N1CC1CC1] | 525.1 | 104 |
| 107 | 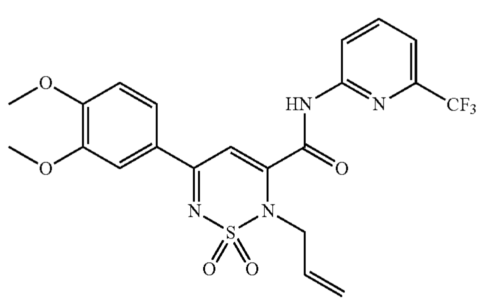 [SMILES: C=CCN1C(C(=O)Nc2cccc(C(F)(F)F)n2)=CC(c2ccc(OC)c(OC)c2)=NS1(=O)=O] | 497.1 | 107 |

*Toluene was applied as solvent at 80-110° C.

The following examples in Table 12 were synthesized according to the procedure described for Example 1 (amide coupling with HATU reagent).

TABLE 12

| Example | Structure | LC-MS (ESI) m/z (M + H)+ | Starting intermediate |
|---------|-----------|--------------------------|----------------------|
| 108 | 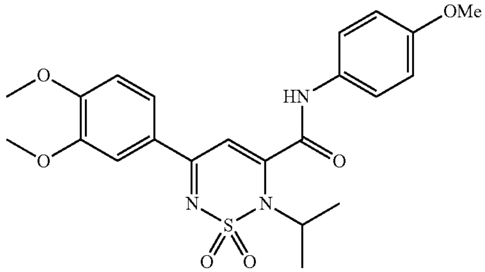 [SMILES: COc1ccc(NC(=O)C2=CC(c3ccc(OC)c(OC)c3)=NS(=O)(=O)N2C(C)C)cc1] | 460.2 | 112 |
| 109 | 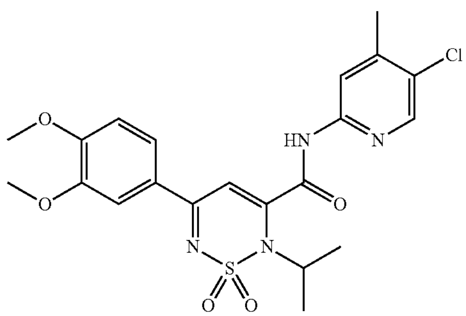 [SMILES: COc1ccc(C2=NS(=O)(=O)N(C(C)C)C(C(=O)Nc3cc(C)c(Cl)cn3)=C2)cc1OC] | 497.1 | 112 |
| 110 | 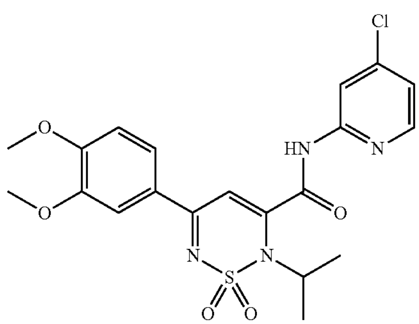 [SMILES: COc1ccc(C2=NS(=O)(=O)N(C(C)C)C(C(=O)Nc3cc(Cl)ccn3)=C2)cc1OC] | 465.2 | 112 |
| 111 | 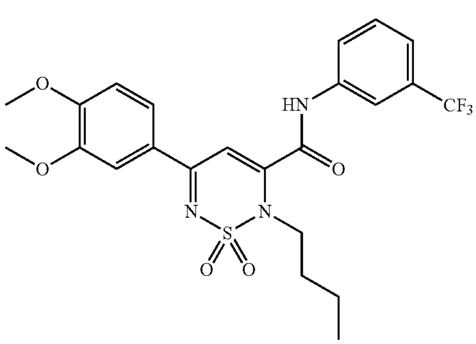 [SMILES: CCCCN1C(C(=O)Nc2cccc(C(F)(F)F)c2)=CC(c2ccc(OC)c(OC)c2)=NS1(=O)=O] | 512.1 | 117 |

TABLE 12-continued

| Example | Structure | LC-MS (ESI) m/z (M + H)+ | Starting intermediate |
|---|---|---|---|
| 112 | 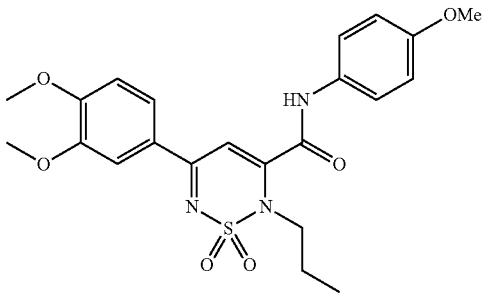 [SMILES: CCCN1C(C(=O)Nc2ccc(OC)cc2)=CC(c2ccc(OC)c(OC)c2)=NS1(=O)=O] | 460.1 | 118 |
| 113 | 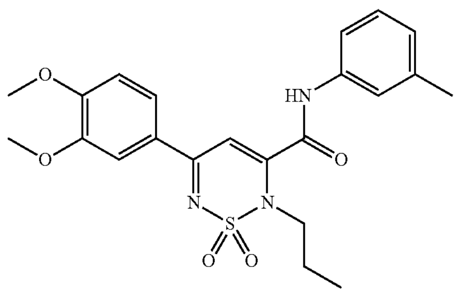 | 444.1 | 118 |
| 114 | 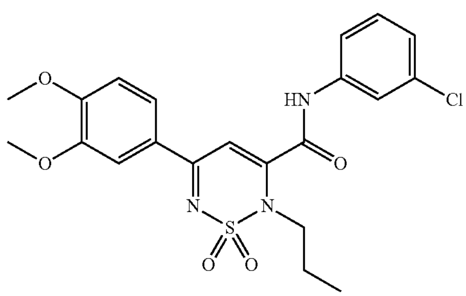 [SMILES: CCCN1C(C(=O)Nc2cccc(Cl)c2)=CC(c2ccc(OC)c(OC)c2)=NS1(=O)=O] | 464.2 | 118 |
| 115 | 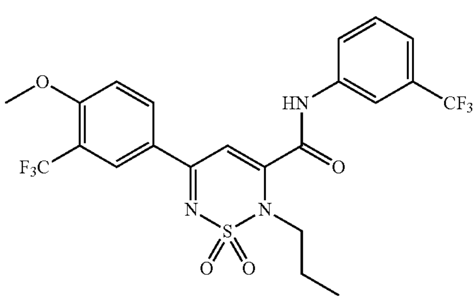 [SMILES: CCCN1C(C(=O)Nc2cccc(C(F)(F)F)c2)=CC(c2ccc(OC)c(C(F)(F)F)c2)=NS1(=O)=O] | 536.2 | 119 |
| 116 | 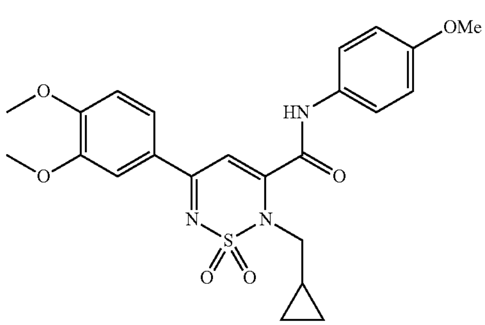 [SMILES: COc1ccc(NC(=O)C2=CC(c3ccc(OC)c(OC)c3)=NS(=O)(=O)N2CC2CC2)cc1] | 472.1 | 120 |

TABLE 12-continued

| Example | Structure | LC-MS (ESI) m/z (M + H)+ | Starting intermediate |
|---|---|---|---|
| 117 | 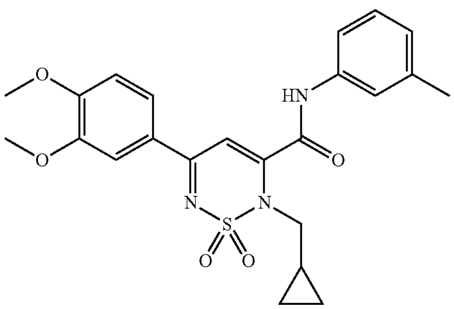 | 456.1 | 120 |
| 118 | 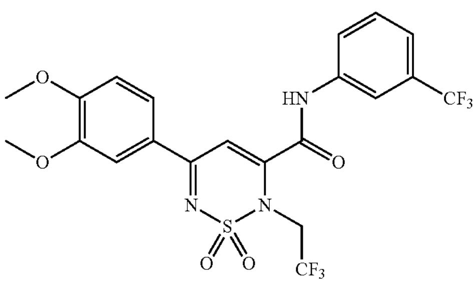 [SMILES: COc1ccc(C2=NS(=O)(=O)N(CC(F)(F)F)C(C(=O)Nc3cccc(C(F)(F)F)c3)=C2)cc1OC] | 538.0 | 123 |
| 119 | 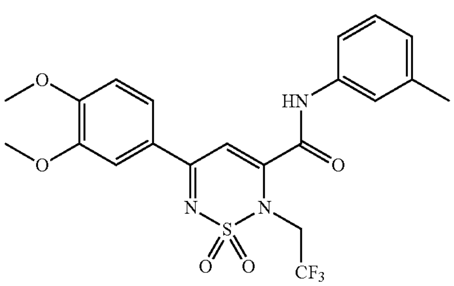 | 484.2 | 123 |
| 120 | 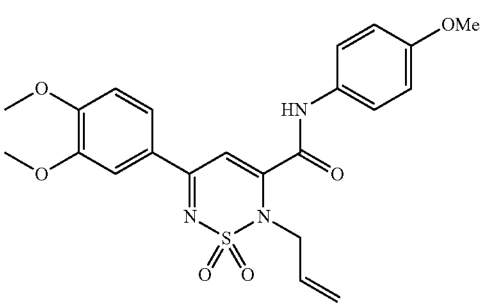 [SMILES: C=CCN1C(C(=O)Nc2ccc(OC)cc2)=CC(c2ccc(OC)c(OC)c2)=NS1(=O)=O] | 458.1 | 124 |
| 121 | 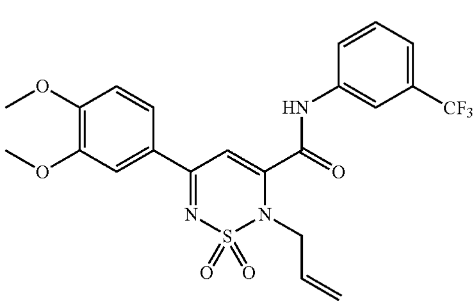 [SMILES: C=CCN1C(C(=O)Nc2cccc(C(F)(F)F)c2)=CC(c2ccc(OC)c(OC)c2)=NS1(=O)=O] | 496.2 | 124 |

TABLE 12-continued

| Example | Structure | LC-MS (ESI) m/z (M + H)⁺ | Starting intermediate |
|---|---|---|---|
| 122 | 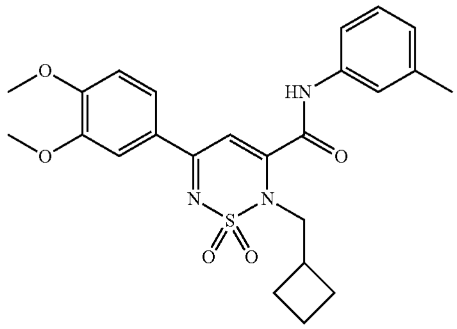 | 409.2 | 125 |

The following examples in Table 13 were synthesized according to the procedure described for Example 53 (amide formation via acid chloride derivatives).

TABLE 13

| Example | Structure | LC-MS (ESI) m/z (M + H)⁺ | Starting intermediate |
|---|---|---|---|
| 123 | 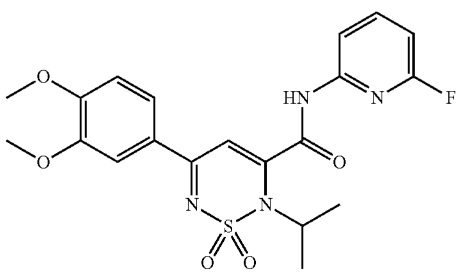 [SMILES: COc1ccc(C2=NS(=O)(=O)N(C(C)C)C(C(=O)Nc3cccc(F)n3)=C2)cc1OC] | 449.1 | 112 |
| 124* | 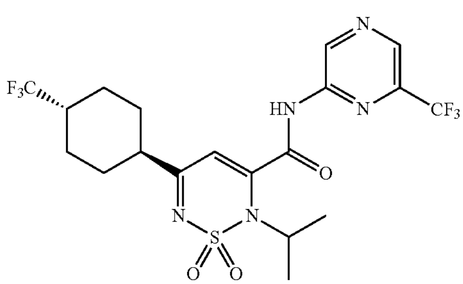 [SMILES: CC(C)N1C(C(=O)Nc2cncc(C(F)(F)F)n2)=CC([C@H]2CC[C@H](C(F)(F)F)CC2)=NS1(=O)=O] | 514.2 | 113 |
| 125 | 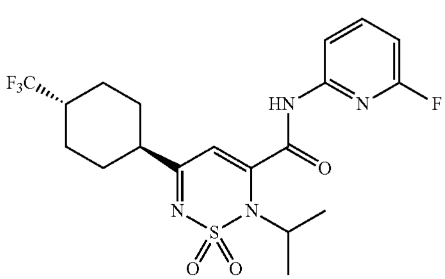 [SMILES: CC(C)N1C(C(=O)Nc2cccc(F)n2)=CC([C@H]2CC[C@H](C(F)(F)F)CC2)=NS1(=O)=O] | M + Na⁺ = 485.1 | 113 |

TABLE 13-continued

| Example | Structure | LC-MS (ESI) m/z (M + H)⁺ | Starting intermediate |
|---|---|---|---|
| 126 | 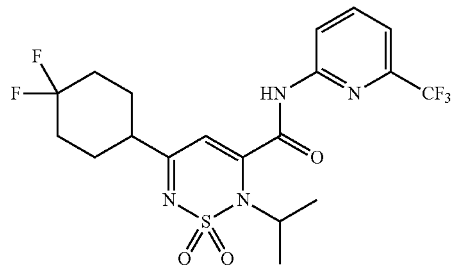 [SMILES: CC(C)N1C(C(=O)Nc2cccc(C(F)(F)F)n2)=CC(C2CCC(F)(F)CC2)=NS1(=O)=O] | 481.2 | 114 |
| 127 | 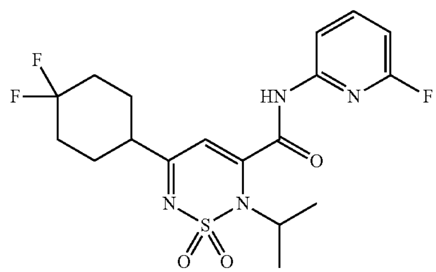 [SMILES: CC(C)N1C(C(=O)Nc2cccc(F)n2)=CC(C2CCC(F)(F)CC2)=NS1(=O)=O] | M + Na⁺ = 453.1 | 114 |
| 128 | 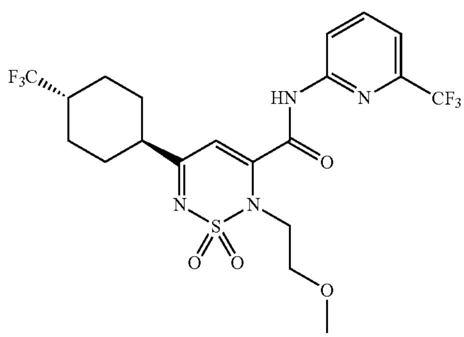 [SMILES: COCCN1C(C(=O)Nc2cccc(C(F)(F)F)n2)=CC([C@H]2CC[C@H](C(F)(F)F)CC2)=NS1(=O)=O] | 529.1 | 115 |
| 129 | 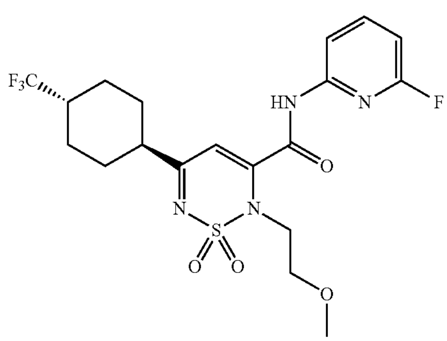 [SMILES: COCCN1C(C(=O)Nc2cccc(F)n2)=CC([C@H]2CC[C@H](C(F)(F)F)CC2)=NS1(=O)=O] | M + Na⁺ = 479.1 | 115 |
| 130 | 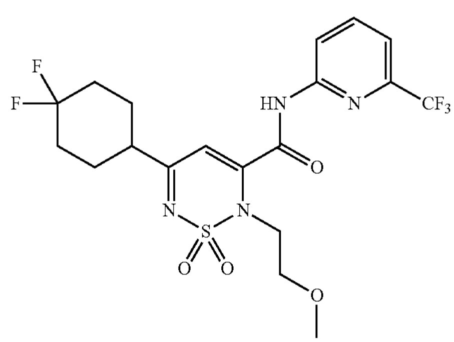 [SMILES: COCCN1C(C(=O)Nc2cccc(C(F)(F)F)n2)=CC(C2CCC(F)(F)CC2)=NS1(=O)=O] | 497.1 | 116 |

TABLE 13-continued

| Example | Structure | LC-MS (ESI) m/z (M + H)+ | Starting intermediate |
|---------|-----------|--------------------------|----------------------|
| 131 | 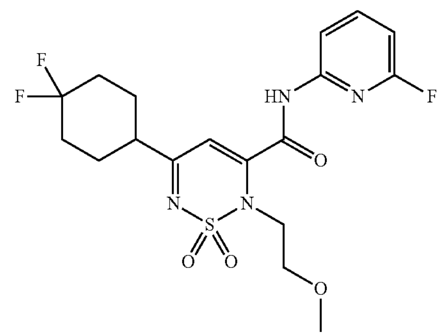 [SMILES: COCCN1C(C(=O)Nc2cccc(F)n2)=CC(C2CCC(F)(F)CC2)=NS1(=O)=O] | 447.1 | 116 |
| 132 | 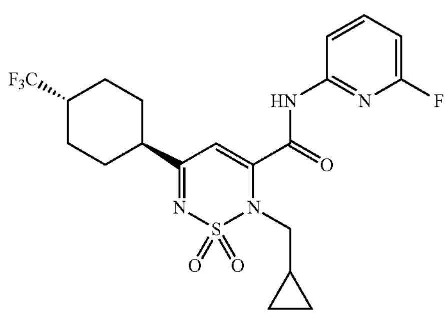 [SMILES: O=C(Nc1cccc(F)n1)C1=CC([C@H]2CC[C@H](C(F)(F)F)CC2)=NS(=O)(=O)N1CC1CC1] | M + Na+ = 497.2 | 121 |
| 133 | 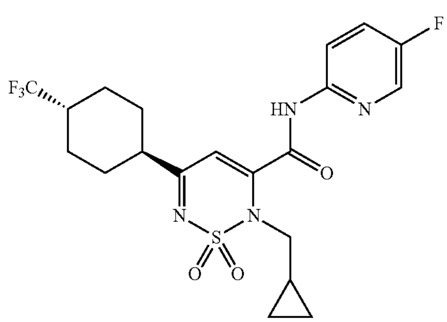 [SMILES: O=C(Nc1ccc(F)cn1)C1=CC([C@H]2CC[C@H](C(F)(F)F)CC2)=NS(=O)(=O)N1CC1CC1] | 475.1 | 121 |
| 134 | 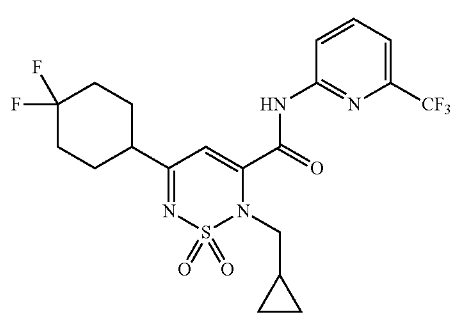 [SMILES: O=C(Nc1cccc(C(F)(F)F)n1)C1=CC(C2CCC(F)(F)CC2)=NS(=O)(=O)N1CC1CC1] | 493.2 | 122 |

TABLE 13-continued

| Example | Structure | LC-MS (ESI) m/z (M + H)+ | Starting intermediate |
|---|---|---|---|
| 135 | 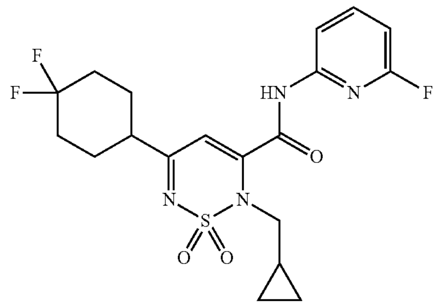 [SMILES: O=C(Nc1cccc(F)n1)C1=CC(C2CCC(F)(F)CC2)=NS(=O)(=O)N1CC1CC1] | M + Na+ = 465.1 | 122 |
| 136* | 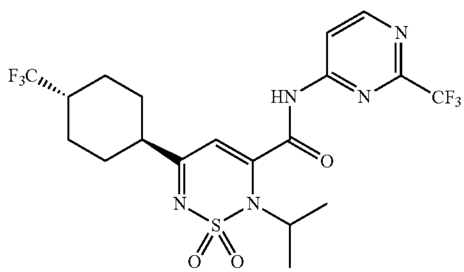 [SMILES: CC(C)N1C(C(=O)Nc2ccnc(C(F)(F)F)n2)=CC([C@H]2CC[C@H](C(F)(F)F)CC2)=NS1(=O)=O] | 514.3 | 113 |
| 137* | 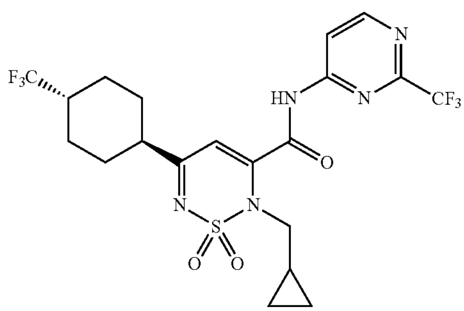 [SMILES: O=C(Nc1ccnc(C(F)(F)F)n1)C1=CC([C@H]2CC[C@H](C(F)(F)F)CC2)=NS(=O)(=O)N1CC1CC1] | 526.3 | 121 |
| 138* | 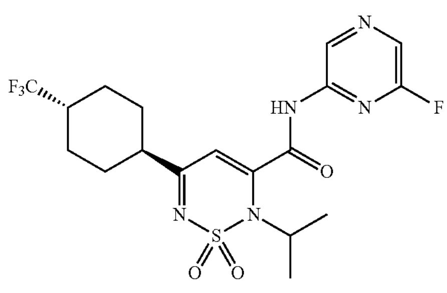 [SMILES: CC(C)N1C(C(=O)Nc2cncc(F)n2)=CC([C@H]2CC[C@H](C(F)(F)F)CC2)=NS1(=O)=O] | 464.3 | 113 |
| 139* | 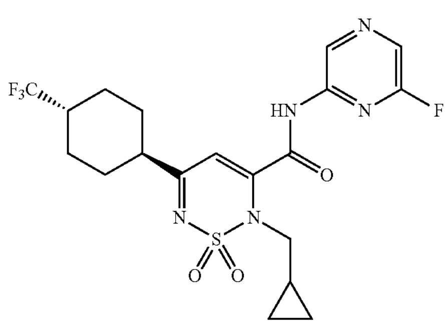 [SMILES: O=C(Nc1cncc(F)n1)C1=CC([C@H]2CC[C@H](C(F)(F)F)CC2)=NS(=O)(=O)N1CC1CC1] | 476.3 | 121 |

*Triethylamine was applied (replacement of K$_3$PO$_4$) in dichloroethane, at 75° C.

Preparation of Pharmaceutical Compositions

The following formulation examples illustrate representative pharmaceutical compositions of this invention. The present invention, however, is not limited to the following pharmaceutical compositions.

A) Solid Oral Dosage Forms

| I., Tablets | |
|---|---|
| Active ingredient(s) | 0.01-90% |
| Filler | 1-99.9% |
| Binder | 0-20% |
| Disintegrant | 0-20% |
| Lubricant | 0-10% |
| Other specific excipient(s) | 0-50% |
| II., Orodispersible films | |
| Active ingredient(s) | 0.01-90% |
| Film forming agent | 1-99.9% |
| Plasticizer | 0-40% |
| Other specific excipient(s) | 0-50% |

B) Liquid Oral Dosage Forms

| III., Oral suspensions | |
|---|---|
| Active ingredient(s) | 0.01-50% |
| Liquid vehicle | 10-99.9% |
| Wetting agent | 0-50% |
| Thickener | 0-50% |
| Buffering agent | quantum satis |
| Osmotic agent | 0-50% |
| Preservatives | quantum satis |
| IV., Syrups | |
| Active ingredient(s) | 0.01-50% |
| Solvent | 10-99.9% |
| Sugar component | 1-20% |
| Flavouring agents | 0-10% |

C) Parenteral Dosage Forms

| V., Intravenous injections | |
|---|---|
| Active ingredient(s) | 0.01-50% |
| Solvent | 10-99.9% |
| Co-solvent | 0-99.9% |
| Osmotic agent | 0-50% |
| Buffering agent | quantum satis |

D) Other Dosage Forms

| VI., Suppositories | |
|---|---|
| Active ingredient(s) | 0.01-50% |
| Suppository baes | 1-99.9% |
| Surface-active agents | 0-20% |
| Lubricants | 0-20% |
| Preservatives | quantum satis |
| VII., Nasal drops or nasal sprays | |
| Active ingredient(s) | 0.01-50% |
| Water | 0-99.9% |
| Solvent | 0-99.9% |
| Co-solvent | 0-99.9% |
| Osmotic agent | 0-20% |
| Viscosity enhancer | 0-20% |
| Buffering agent | quantum satis |
| Preservatives | quantum satis |

Biological Activity

Human α7 Nicotinic Acetylcholine Receptor $[Ca^{2+}]_i$ Assay

Cells: Flp-In 293 cells stably expressing human α7 nAchR and human RIC-3 (α7 cells, generated in house.)

Materials: 96-well plates coated with PDL (Falcon), culture medium, assay buffer, DMSO, FLIPR Calcium 5 kit (Molecular Devices), probenecid, agonist and PAM test compounds.

| Culture medium: | Assay buffer: |
|---|---|
| DMEM (Dulbecco's Modified Eagle Medium, Gibco) | 140 mM NaCl |
| 10% FBS (Fetal Bovine Serum, Gibco) | 5 mM KCl |
| 1% glutamine (Sigma G) | 10 mM HEPES |
| 50 µg/ml Hygromycin B | 2 mM $MgCl_2$ |
| 800 µg/ml G418 | 2 mM $CaCl_2$ |
| 1% penicillinstreptomycinantimycotic sol. (PSA, Sigma) | 10 mM glucose |
| | 2 mM probenecid, pH = 7.4 |

Brief Description of the Method ($Ca^{2+}$ Fluorometry)

α7 cells cells stably expressing human α7 nAchR were cultured in the medium detailed above, and were split twice a week. For the fluorometric measurements of cytosolic $Ca^{2+}$ ion concentration ($[Ca^{2+}]_i$) cells were seeded in 96-well microplates at a density of 60000 cells/well and maintained overnight in a tissue culture incubator at 37° C. under an atmosphere of 95% air/5% $CO_2$. The plating medium was identical with the culture medium. 50 µl of the growth medium was aspirated with a cell washer (BioTek Elx405UCVWS). Then 50 µl/well Calcium 5 kit diluted 2-fold in assay buffer was added manually using an 8-channel pipette. After an incubation period (20 minutes, 37° C.) 50 µl/well assay buffer containing vehicle (DMSO, 4% added) or reference α7 PAMs (4×of the final concentration) were added manually and the cells were incubated for an additional 10 minutes at 37° C. Baseline and agonist-evoked [Ca2+]i-changes were monitored with FlexStation II (Molecular Devices, Sunnyvale, Calif.), a plate reader fluorometer with integrated 8-channel fluid addition capability. Fluorescence measurements were carried out at 37° C. The dye was excited at 485 nm, emission was sampled at 525 nm at 1.4-s intervals. Baseline was recorded for 20 seconds followed by agonist stimulation. 50 µl 4× concentrated agonist solution was added to the cells using the pipettor of FlexStation II and fluorescence was monitored for an additional 40 seconds. Final DMSO concentration was 1% for all treatments. To achieve this, a series of DMSO stock solutions were prepared from all test compounds. These stocks were stored under 0° C. and were further diluted in assay buffer to obtain the desired final concentration immediately before the measurement. Agonist and PAM concentration-response studies were conducted in the presence of saturating concentrations of PAMs (mostly PNU-120596, 5 µM) and agonists (mostly PNU-282987, 1 µM), respectively. Results were expressed as ΔF/F values using SoftMax Pro software (Molecular Devices), where F was the resting fluorescence preceding agonist application and ΔF was the increase in fluorescence at a given time (ΔF=maximum fluorescence intensity values after stimulation minus average fluorescence intensity values before stimulation). In all experiments, all treatments were measured in multiple wells in parallel, and the mean ΔF/F values were used for analysis.

Table 14 shows the PAM $EC_{50}$ values in the $[Ca^{2+}]_i$ assay:

TABLE 14

| Example | $EC_{50}$ (nM) |
| --- | --- |
| 1 | 430 |
| 2 | 1400 |
| 3 | 690 |
| 4 | 980 |
| 5 | 210 |
| 6 | 1300 |
| 7 | 2000 |
| 8 | 1800 |
| 9 | 1600 |
| 10 | 670 |
| 11 | 440 |
| 12 | 230 |
| 13 | 340 |
| 14 | 1400 |
| 15 | 3000 |
| 16 | 1400 |
| 17 | 2800 |
| 18 | 2900 |
| 19 | 1600 |
| 20 | 940 |
| 21 | 230 |
| 22 | 370 |
| 23 | 400 |
| 24 | 210 |
| 25 | 1400 |
| 26 | 360 |
| 27 | 110 |
| 28 | 1200 |
| 29 | 340 |
| 30 | 440 |
| 31 | 440 |
| 32 | 720 |
| 33 | 50 |
| 34 | 130 |
| 35 | 150 |
| 36 | 310 |
| 37 | 45 |
| 38 | 45 |
| 39 | 150 |
| 40 | 60 |
| 41 | 100 |
| 42 | 120 |
| 43 | 110 |
| 44 | 360 |
| 45 | 210 |
| 46 | 170 |
| 47 | 500 |
| 48 | 330 |
| 49 | 490 |
| 50 | 1100 |
| 51 | 810 |
| 52 | 1600 |
| 53 | 90 |
| 54 | 480 |
| 55 | 470 |
| 56 | 2500 |
| 57 | 2000 |
| 58 | 1200 |
| 59 | 1300 |
| 60 | 300 |
| 61 | 100 |
| 62 | 2800 |
| 63 | 190 |
| 64 | 330 |
| 65 | 1100 |
| 66 | 430 |
| 67 | 220 |
| 68 | 140 |
| 69 | 1100 |
| 70 | 620 |
| 71 | 140 |
| 72 | 430 |
| 73 | 390 |
| 74 | 1100 |
| 75 | 960 |
| 76 | 85 |
| 77 | 1500 |
| 78 | 790 |
| 79 | 320 |
| 80 | 350 |
| 81 | 120 |
| 82 | 120 |
| 83 | 310 |
| 84 | 130 |
| 85 | 2000 |
| 86 | 2900 |
| 87 | 10 |
| 88 | 1400 |
| 89 | 290 |
| 90 | 1200 |
| 91 | 35 |
| 92 | 290 |
| 93 | 120 |
| 94 | 340 |
| 95 | 45 |
| 96 | 330 |
| 97 | 30 |
| 98 | 100 |
| 99 | 40 |
| 100 | 150 |
| 101 | 65 |
| 102 | 320 |
| 103 | 110 |
| 104 | 370 |
| 105 | 120 |
| 106 | 70 |
| 107 | 55 |
| 108 | 1300 |
| 109 | 240 |
| 110 | 640 |
| 111 | 200 |
| 112 | 75 |
| 113 | 80 |
| 114 | 380 |
| 115 | 85 |
| 116 | 100 |
| 117 | 110 |
| 118 | 530 |
| 119 | 380 |
| 120 | 120 |
| 121 | 220 |
| 122 | 320 |
| 123 | 55 |
| 124 | 110 |
| 125 | 45 |
| 126 | 220 |
| 127 | 580 |
| 128 | 310 |
| 129 | 190 |
| 130 | 960 |
| 131 | 1800 |
| 132 | 35 |
| 133 | 230 |
| 134 | 80 |
| 135 | 120 |
| 136 | 150 |
| 137 | 130 |
| 138 | 140 |
| 139 | 150 |

In Vivo Pharmacology (Place Recognition Test)

Animals: Male NMRI mice (Toxicoop, Hungary)

Substances: Scopolamine was dissolved in saline and administered at 1 mg/kg dose i.p. Test compounds were administered 30 minutes before the acquisition trial (T1) and scopolamine after the acquisition trial at a volume of 0.1 ml/10 g.

Procedure: The task was carried out in a transparent plexiglass Y-maze (each arm has a length of 40 cm, an inner width of 11 cm and a height of 30 cm). Numerous visual cues were placed around the arms and were kept constant during the experiment. The test consisted of two trials (T1 and T2) separated by an intertrial interval of 30 minutes. Mice were placed in the starting arm of the maze at the beginning of each trial. In T1, one of the symmetric arms of the maze was closed (it will be novel in T2) and the animals were allowed to explore the maze for 5 minutes (acquisition phase). In T2, mice had free access to all three arms for 2 minutes (retrieval phase). The time spent with exploration in the novel and familiar arms during T2 was measured. Differences between the exploration times spent in the familiar vs. novel arms of the maze for each group were evaluated by MANOVA, followed by Duncan post hoc test.

Table 15 shows the reversal of the scopolamine-induced amnesia in the place recognition assay in mice:

TABLE 15

|  | Dose (i.p.) | | |
| --- | --- | --- | --- |
|  | 1 mg/kg | 3 mg/kg | 10 mg/kg |
| Example 1 | ++ | +++ | +++ |
| Example 21 | ++ | +++ | ++ |
| Example 29 | +++ | ++ | +++ |
| Example 33 | +++ | ++ | ++ |
| Example 37 | +++ | ++ | +++ |
| Example 91 | +++ | + | +++ |
| Example 94 | +++ | +++ | +++ |

+p < 0.05 ; ++p < 0.01; +++p < 0.001

Significant differences ($^+p<0.05$; $^{++}p<0.01$; $^{+++}p<0.001$) were observed between the exploration times spent in the novel vs. familiar arms of the maze.

The invention claimed is:

1. A method for positive allosteric modulation of the α7 nicotinic acetylcholine receptor in a mammal suffering from a disease which requires positive allosteric modulation of the α7 nicotinic acetylcholine receptor comprising administering to a mammal in need thereof an effective amount of at least one compound of formula(I),

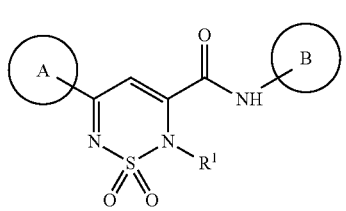

(I)

wherein
A is saturated, unsaturated or aromatic, monocyclic or bicyclic, fused or bridged carbocyclyl, or a saturated, unsaturated or aromatic monocyclic or bicyclic, fused or bridged heterocyclyl, optionally substituted by one or more halogen atoms, $C_{1-6}$alkyl, $C_{1-6}$alkoxy, or halo$C_{1-6}$alkyl;
B is saturated, unsaturated or aromatic, monocyclic or bicyclic, fused or bridged carbocyclyl, or a saturated, unsaturated or aromatic monocyclic or bicyclic, fused or bridged heterocyclyl, optionally substituted by one or more halogen atoms, $C_{1-6}$alkyl, $C_{1-6}$alkoxy, halo$C_{1-6}$alkyl, CN, C(O)$C_{1-6}$alkyl, or halo$C_{1-6}$alkoxy;
$R^1$ is $C_{1-6}$alkyl, $C_{1-6}$alkenyl, halo$C_{1-6}$alkyl, $C_{3-8}$cycloalkyl$C_{1-6}$alkyl, $C_{1-6}$alkoxy$C_{1-6}$alkyl, or $C_{4-6}$heterocyclyl;

or pharmaceutically acceptable salt, biologically active metabolites, pro-drugs, racemates, enantiomers, diastereomers, solvates or hydrate thereof.

2. The method according to claim 1, wherein
A is an optionally substituted saturated, unsaturated or aromatic, 4-9 membered monocyclic or bicyclic, fused or bridged carbocyclyl, or a saturated, unsaturated or aromatic 4-9 membered monocyclic or bicyclic, fused or bridged heterocyclyl containing 1-3 heteroatoms selected from the group consisting of nitrogen, and oxygen;
B is an optionally substituted saturated, unsaturated or aromatic, 4-9 membered monocyclic or bicyclic, fused or bridged carbocyclyl, or a saturated, unsaturated or aromatic 4-9 membered monocyclic or bicyclic, fused or bridged heterocyclyl containing 1-3 heteroatoms selected from the group consisting of nitrogen, and oxygen;
$R^1$ is $C_{1-6}$alkyl, $C_{1-6}$alkenyl, halo$C_{1-6}$alkyl, $C_{3-8}$cycloalkyl$C_{1-6}$alkyl, $C_{1-6}$alkoxy$C_{1-6}$alkyl, or $C_{4-6}$heterocyclyl.

3. The method according to claim 1, wherein
A is an optionally substituted cyclopentenyl, cyclohexyl, phenyl, cycloheptyl, bicyclo[3.1.0]hexanyl or indazolyl;
B is an optionally substituted phenyl, pyridinyl, pyrazolyl, pyrazinyl, pyrimidinyl, benzodioxolyl, 1,2,3,4-tetrahydro-isoquinolinyl, or pyrazolopyridinyl;
R1 is $CH_3$, $C_2H_5$, nPr, iPr, nBu, secBu, allyl, —$CH_2$—$CF_3$, —$CH_2$-cyclobutyl, —$CH_2$-cyclopropyl, —$C_2H_5$—O—$CH_3$, or tetrahydrofuryl.

4. The method according to claim 1, wherein the compound is selected from the group consisting of:
5-(3,4-dimethoxyphenyl)-2-methyl-N-(3-methylphenyl)-1,1-dioxo-2H-1λ$^6$,2,6-thiadiazine-3-carboxamide;
5-(1,3-dimethyl-1H-indazol-5-yl)-2-methyl-N-(3-methylphenyl)-1,1-dioxo-2H-1λ$^6$,2,6-thiadiazine-3-carboxamide;
5-(3,4-dimethoxyphenyl)-2-ethyl-N-(3-methylphenyl)-1,1-dioxo-2H-1λ$^6$,2,6-thiadiazine-3-carboxamide;
5-(3,4-dimethoxyphenyl)-2-ethyl-1,1-dioxo-N-[6-(trifluoromethyl)pyridin-2-yl]-2H-1λ$^6$,2,6-thiadiazine-3-carboxamide;
2-ethyl-5-[4-methoxy-3-(trifluoromethyl)phenyl]-N-(3-methoxyphenyl)-1,1-dioxo-2H-1λ$^6$,2,6-thiadiazine-3-carboxamide;
2-ethyl-5-[4-methoxy-3-(trifluoromethyl)phenyl]-N-(4-methoxyphenyl)-1,1-dioxo-2H-1λ$^6$,2,6-thiadiazine-3-carboxamide;
2-ethyl-1,1-dioxo-5-[(1r,4r)-4-(trifluoromethyl)cyclohexyl]-N-[6-(trifluoromethyl)pyridin-2-yl]-2H-1λ$^6$,2,6-thiadiazine-3-carboxamide;
N-(6-cyanopyridin-2-yl)-2-ethy]-1,1-dioxo-5-[(1r,4r)-4-(trifluoromethyl)cyclohexyl]-2H-1λ$^6$,2,6-thiadiazine-3-carboxamide;
5-(3,4-dimethoxyphenyl)-1,1-dioxo-2-(propan-2-yl)-N-[6-(trifluoromethyl)pyridin-2-yl]-2H1λ$^6$,2,6-thiadiazine-3-carboxamide;
5-(3,4-dimethoxyphenyl)-1,1-dioxo-2-propyl-N-[3-(trifluoromethyl)phenyl]-2H-1λ$^6$,2,6-thiadiazine-3-carboxamide;
5-(3,4-dimethoxyphenyl)-1,1-dioxo-2-propyl-N-[6-(trifluoromethyl)pyridin-2-yl]-2H-1λ$^6$,2,6-thiadiazine-3-carboxamide;
5-[4-methoxy-3-(trifluoromethyl)phenyl]-1,1-dioxo-2-propyl-N-[6-(trifluoromethyl)pyridin-2-yl]-2H-1λ$^6$,2,6-thiadiazine-3-carboxamide;

5-(4-methoxy-3-methylphenyl)-1,1-dioxo-2-propyl-N-[6-(trifluoromethyl)pyridin-2-yl]-2H-1λ⁶,2,6-thiadiazine-3-carboxamide;

5-(3-chloro-4-methoxyphenyl)-1,1-dioxo-2-propyl-N-[6-(trifluoromethyl)pyridin-2-yl]-2H-1λ⁶,2,6-thiadiazine-3-carboxamide;

2-(cyclopropylmethyl)-1,1-dioxo-5-[(1r,4r)-4-(trifluoromethyl)cyclohexyl]-N-[6-(trifluoromethyl)pyridin-2-yl]-2H1λ⁶,2,6-thiadiazine-3-carboxamide;

5-(3,4-dimethoxyphenyl)-1,1-dioxo-2-(prop-2-en-1-yl)-N-[6-(trifluoromethyl)pyridin-2-yl]-2H-1λ⁶,2,6-thiadiazine-3-carboxamide;

5-(3,4-dimethoxyphenyl)-N-(4-methoxyphenyl)-1,1-dioxo-2-propyl-2H-1λ⁶,2,6-thiadiazine-3-carboxamide;

5-(3,4-dimethoxyphenyl)-N-(3-methylphenyl)-1,1-dioxo-2-propyl-2H-1λ⁶,2,6-thiadiazine-3-carboxamide;

5-[4-methoxy-3-(trifluoromethyl)phenyl]-1,1-dioxo-2-propyl-N-[3-(trifluoromethyl)phenyl]-2H-1λ⁶,2,6-thiadiazine-3-carboxamide;

5-(3,4-dimethoxyphenyl)-N-(6-fluoropyridin-2-yl)-1,1-dioxo-2-(propan-2-yl)-2H-1λ⁶,2,6-thiadiazine-3-carboxamide;

N-(6-fluoropyridin-2-yl)-1,1-dioxo-2-(propan-2-yl)-5-[(1r,4r)-4-(trifluoromethyl)cyclohexyl]-2H1λ⁶,2,6-thiadiazine-3-carboxamide;

2-(cyclopropylmethyl)-N-(6-fluoropyrazin-2-yl)-1,1-dioxo-5-[(1r,4r)-4-(trifluoromethyl)cyclohexyl]-2H-1λ⁶,2,6-thiadiazine-3-carboxamide;

2-[(2R)-butan-2-yl]-5-(3,4-dimethoxyphenyl)-1,1-dioxo-N-[6-(trifluoromethyl)pyridin-2-yl]-2H-1λ⁶,2,6-thiadiazine-3-carboxamide;

2-ethyl-5-[4-methoxy-3-(trifluoromethyl)phenyl]-1,1-dioxo-N-[6-(trifluoromethyl)pyridin-2-yl]-2H-1λ⁶,2,6-thiadiazine-3-carboxamide;

1,1-dioxo-2-(propan-2-yl)-5-[(1r,4r)-4-(trifluoromethyl)cyclohexyl]-N-[6-(trifluoromethyl)pyrazin-2-yl]-2H-1λ⁶,2, 6-thiadiazine-3-carboxamide;

2-(cyclopropylmethyl)-5-(4,4-difluorocyclohexyl)-1,1-dioxo-N-[6-(trifluoromethyl)pyridin-2-yl]-2H-1λ⁶,2,6-thiadiazine-3-carboxamide;

2-(cyclopropylmethyl)-1,1-dioxo-5-[(1r,4r)-4-(trifluoromethyl)cyclohexyl]-N-[2-(trifluoromethyl)pyrimidin-4-yl]-2H-1λ⁶,2,6-thiadiazine-3-carboxamide;

or pharmaceutically acceptable salt, biologically active metabolites, pro-drugs, racemates, enantiomers, diastereomers, solvates or hydrate thereof.

5. The method according to claim 1, wherein the disease is selected from the group consisting of schizophrenia, schizophreniform disorder, schizoaffective disorder, delusional disorder, brief psychotic disorder, psychotic disorder due to a general medical condition, substance-induced psychotic disorder, cognitive impairment, net limited to, cognitive impairment as a result of stroke, Alzheimer's disease, Huntington's disease, Pick disease, HIV associated dementia, frontotemporal dementia, Lewy body dementia, vascular dementia, cerebrovascular disease, dementia associated to amyotrophic lateral sclerosis, delirium, traumatic brain injury, senile dementia, mild cognitive impairment, Down's syndrome, depression and cognitive deficit, Parkinson's disease, neuroleptic-induced parkinsonism, tardive dyskinesias, mood disorders, depressive disorders and episodes, bipolar disorders, cyclothymic disorder, substance-induced mood disorder, anxiety disorders, panic disorder and panic attacks, obsessive compulsive disorder, posttraumatic stress disorder, acute stress disorder, generalized anxiety disorder, anxiety disorder due to a general medical condition, substance-induced anxiety disorder, phobias, substance use or substance-induced disorders, narcolepsy, dyssomnias, primary hypersomnia, breathing-related sleep disorders, circadian rhythm sleep disorder, parasomnias, sleep terror disorder, sleepwalking disorder, sleep disorder due to a general medical condition and substance-induced sleep disorder, metabolic and eating disorders, anorexia nervosa, bulimia nervosa, obesity, compulsive eating disorder, binge eating disorder, diabetes mellitus, ulcerative colitis, Crohn's disease, irritable bowel syndrome, autism spectrum disorders, autistic disorder, Asperger's disorder, Rett's disorder, childhood disintegrative disorder, attention deficit hyperactivity disorder, disruptive behavior disorders, oppositional defiant disorder, tic disorders, Tourette's disorder, personality disorders, sexual dysfunctions, sexual desire disorders, sexual arousal disorders, orgasmic disorders, sexual pain disorder, paraphilias, gender identity disorders, infertility, premenstrual syndrome, disorders of the respiratory system, disorders of the cardiovascular system, cardiac failure, heart arrhythmia, hypertension, inflammation, inflammatory and neuropathic pain, rheumatoid arthritis, osteoarthritis, allergy, sarcoidosis, psoriasis, ataxia, dystonia, systemic lupus erythematosus, mania, restless legs syndrome, progressive supranuclear palsy, epilepsy, myoclonus, migraine, amnesia, chronic fatigue syndrome, cataplexy, brain ischemia, multiple sclerosis, encephalomyelitis, jetlag, cerebral amyloid angiopathy, and sepsis.

6. The method according to claim 5, wherein the disease is selected from the group consisting of cognitive impairment, schizophrenia, and autism.

7. A method for positive allosteric modulation of the α7 nicotinic acetylcholine receptor in a mammal suffering from a disease which requires positive allosteric modulation of the α7 nicotinic acetylcholine receptor comprising administering to a mammal in need thereof an effective amount of a combination of a compound of formula (I),

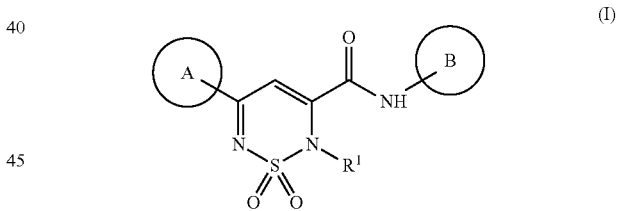

wherein

A is saturated, unsaturated or aromatic, monocyclic or bicyclic, fused or bridged carbocyclyl, or a saturated, unsaturated or aromatic monocyclic or bicyclic, fused or bridged heterocyclyl, optionally substituted by one or more halogen atoms, $C_{1-6}$alkyl, $C_{1-6}$alkoxy, or halo$C_{1-6}$alkyl;

B is saturated, unsaturated or aromatic, monocyclic or bicyclic, fused or bridged carbocyclyl, or a saturated, unsaturated or aromatic monocyclic or bicyclic, fused or bridged heterocyclyl, optionally substituted by one or more halogen atoms, $C_{1-6}$alkyl, $C_{1-6}$alkoxy, halo$C_{1-6}$alkyl, CN, C(O)$C_{1-6}$alkyl, or halo$C_{1-6}$alkoxy;

$R^1$ is $C_{1-6}$alkyl, $C_{1-6}$alkenyl, halo$C_{1-6}$alkyl, $C_{3-8}$cycloalkyl$C_{1-6}$alkyl, $C_{1-6}$alkoxy$C_{1-6}$alkyl, or $C_{4-6}$heterocyclyl;

or pharmaceutically acceptable salt, biologically active metabolites, pro-drugs, racemates, enantiomers, diastereomers, solvates or hydrate thereof, and at least one other active ingredient.

8. The method according to claim 7, wherein the other active ingredient(s) are selected from the group consisting of acetylcholinesterase inhibitors, NMDA receptor antagonists, beta-secretase inhibitors, antipsychotics, $GABA_A$ receptor alpha5 subunit NAMs or PAMs, histamine $H_3$ receptor antagonists, 5-$HT_6$ receptor antagonists, M1 or M4 mAChR agonists or PAMs, mGluR2 antagonists or NAMs or PAMs, and levodopa.

9. The method according to claim 1, wherein the compound is selected from the group consisting of:
- 5-(3,4-dimethoxyphenyl)-2-methyl-N-(3-methylphenyl)-1,1-dioxo-2H-1$\lambda^6$,2, 6-thiadiazine-3-carboxamide;
- 5-(1,3-dimethyl-1H-indazol-5-yl)-2-methyl-N-(3-methylphenyl)-1,1-dioxo-2H-1$\lambda^6$,2,6-thiadiazine-3-carboxamide;
- 5-(3,4-dimethoxyphenyl)-2-ethyl-N-(3-methylphenyl)-1,1-dioxo-2H-1$\lambda^6$,2,6-thiadiazine-3-carboxamide;
- 5-(3,4-dimethoxyphenyl)-2-ethyl-1,1-dioxo-N-[6-(trifluoromethyl)pyridin-2-yl]-2H-1$\lambda^6$,2,6-thiadiazine-3-carboxamide;
- or pharmaceutically acceptable salt, biologically active metabolites, pro-drugs, racemates, enantiomers, diastereomers, solvates or hydrate thereof.

10. The method according to claim 1, wherein the compound is selected from the group consisting of:
- 2-ethyl-5-[4-methoxy-3-(trifluoromethyl)phenyl]-N-(3-methoxyphenyl)-1,1-dioxo-2H-1$\lambda^6$,2,6-thiadiazine-3-carboxamide;
- 2-ethyl-5-[4-methoxy-3-(trifluoromethyl)phenyl]-N-(4-methoxyphenyl)-1,1-dioxo-2H-1$\lambda^6$,2,6-thiadiazine-3-carboxamide;
- 2-ethyl-1,1-dioxo-5-[(1r,4r)-4-(trifluoromethyl)cyclohexyl]-N-[6-(trifluoromethyl)pyridin-2-yl]-2H-1$\lambda^6$,2,6-thiadiazine-3-carboxamide;
- N-(6-cyanopyridin-2-yl)-2-ethy]-1,1-dioxo-5-[(1r,4r)-4-(trifluoromethyl)cyclohexyl]-2H-1$\lambda^6$,2,6-thiadiazine-3-carboxamide;
- or pharmaceutically acceptable salt, biologically active metabolites, pro-drugs, racemates, enantiomers, diastereomers, solvates or hydrate thereof.

11. The method according to claim 1, wherein the compound is selected from the group consisting of:
- 5-(3,4-dimethoxyphenyl)-1,1-dioxo-2-(propan-2-yl)-N-[6-(trifluoromethyl)pyridin-2-yl]-2H-1$\lambda^6$,2,6-thiadiazine-3-carboxamide;
- 5-(3,4-dimethoxyphenyl)-1,1-dioxo-2-propyl-N-[3-(trifluoromethyl)phenyl]-2H-1$\lambda^6$,2,6-thiadiazine-3-carboxamide;
- 5-(3,4-dimethoxyphenyl)-1,1-dioxo-2-propyl-N-[6-(trifluoromethyl)pyridin-2-yl]-2H-1$\lambda^6$,2,6-thiadiazine-3-carboxamide;
- 5-[4-methoxy-3-(trifluoromethyl)phenyl]-1,1-dioxo-2-propyl-N-[6-(trifluoromethyl)pyridin-2-yl]-2H-1$\lambda^6$,2,6-thiadiazine-3-carboxamide;
- or pharmaceutically acceptable salt, biologically active metabolites, pro-drugs, racemates, enantiomers, diastereomers, solvates or hydrate thereof.

12. The method according to claim 1, wherein the compound is selected from the group consisting of:
- 5-(4-methoxy-3-methylphenyl)-1,1-dioxo-2-propyl-N-[6-(trifluoromethyl)pyridin-2-yl]-2H-1$\lambda^6$,2,6-thiadiazine-3-carboxamide;
- 5-(3-chloro-4-methoxyphenyl)-1,1-dioxo-2-propyl-N-[6-(trifluoromethyl)pyridin-2-yl]-2H-1$\lambda^6$,2,6-thiadiazine-3-carboxamide;
- 2-(cyclopropylmethyl)-1,1-dioxo-5-[(1r,4r)-4-(trifluoromethyl)cyclohexyl]-N-[6-(trifluoromethyl)pyridin-2-yl]-2H-1$\lambda^6$,2,6-thiadiazine-3-carboxamide;
- 5-(3,4-dimethoxyphenyl)-1,1-dioxo-2-(prop-2-en-1-yl)-N-[6-(trifluoromethyl)pyridin-2-yl]-2H-1$\lambda^6$,2,6-thiadiazine-3-carboxamide;
- or pharmaceutically acceptable salt, biologically active metabolites, pro-drugs, racemates, enantiomers, diastereomers, solvates or hydrate thereof.

13. The method according to claim 1, wherein the compound is selected from the group consisting of:
- 5-(3,4-dimethoxyphenyl)-N-(4-methoxyphenyl)-1,1-dioxo-2-propyl-2H1$\lambda^6$,2,6-thiadiazine-3-carboxamide;
- 5-(3,4-dimethoxyphenyl)-N-(3-methylphenyl)-1,1-dioxo-2-propyl-2H1$\lambda^6$,2,6-thiadiazine-3-carboxamide;
- 5-[4-methoxy-3-(trifluoromethyl)phenyl]-1,1-dioxo-2-propyl-N-[3-(trifluoromethyl)phenyl]-2H1$\lambda^6$,2,6-thiadiazine-3-carboxamide;
- 5-(3,4-dimethoxyphenyl)-N-(6-fluoropyridin-2-yl)-1,1-dioxo-2-(propan-2-yl)-2H-1$\lambda^6$,2,6-thiadiazine-3-carboxamide;
- or pharmaceutically acceptable salt, biologically active metabolites, pro-drugs, racemates, enantiomers, diastereomers, solvates or hydrate thereof.

14. The method according to claim 1, wherein the compound is selected from the group consisting of:
- N-(6-fluoropyridin-2-yl)-1,1-dioxo-2-(propan-2-yl)-5-[(1r,4r)-4-(trifluoromethyl)cyclohexyl]-2H-1$\lambda^6$,2,6-thiadiazine-3-carboxamide;
- 2-(cyclopropylmethyl)-N-(6-fluoropyrazin-2-yl)-1,1-dioxo-5-[(1r,4r)-4-(trifluoromethyl)cyclohexyl]-2H-1$\lambda^6$,2,6-thiadiazine-3-carboxamide;
- 2-[(2R)-butan-2-yl]-5-(3,4-dimethoxyphenyl)-1,1-dioxo-N-[6-(trifluoromethyl)pyridin-2-yl]-2H-1$\lambda^6$,2,6-thiadiazine-3-carboxamide;
- 2-ethyl-5-[4-methoxy-3-(trifluoromethyl)phenyl]-1,1-dioxo-N-[6-(trifluoromethyl)pyridin-2-yl]-2H-1$\lambda^6$,2,6-thiadiazine-3-carboxamide;
- or pharmaceutically acceptable salt, biologically active metabolites, pro-drugs, racemates, enantiomers, diastereomers, solvates or hydrate thereof.

15. The method according to claim 1, wherein the compound is selected from the group consisting of:
- 1,1-dioxo-2-(propan-2-yl)-5-[(1r,4r)-4-(trifluoromethyl)cyclohexyl]-N-[6-(trifluoromethyl)pyrazin-2-yl]-2H-1$\lambda^6$,2,6-thiadiazine-3-carboxamide;
- 2-(cyclopropylmethyl)-5-(4,4-difluorocyclohexyl)-1,1-dioxo-N-[6-(trifluoromethyl)pyridin-2-yl]-2H-1$\lambda^6$,2,6-thiadiazine-3-carboxamide;
- 2-(cyclopropylmethyl)-1,1-dioxo-5-[(1r,4r)-4-(trifluoromethyl)cyclohexyl]-N-[2-(trifluoromethyl)pyrimidin-4-yl]-2H-1$\lambda^6$,2,6-thiadiazine-3-carboxamide;
- or pharmaceutically acceptable salt, biologically active metabolites, pro-drugs, racemates, enantiomers, diastereomers, solvates or hydrate thereof.

* * * * *